(12) United States Patent
Fanslow, III et al.

(10) Patent No.: US 7,074,408 B2
(45) Date of Patent: Jul. 11, 2006

(54) USE OF INTEGRIN ANTAGONISTS TO INHIBIT ANGIOGENESIS

(75) Inventors: William C. Fanslow, III, Seattle, WA (US); Douglas P. Cerretti, Seattle, WA (US); Kurt M. Poindexter, Seattle, WA (US); Roy A. Black, Seattle, WA (US)

(73) Assignee: Immunex Corporation, Seattle, WA (US)

( * ) Notice: Subject to any disclaimer, the term of this patent is extended or adjusted under 35 U.S.C. 154(b) by 0 days.

(21) Appl. No.: 09/792,200

(22) Filed: Feb. 23, 2001

(65) Prior Publication Data

US 2002/0042368 A1    Apr. 11, 2002

Related U.S. Application Data

(60) Provisional application No. 60/184,865, filed on Feb. 25, 2000.

(51) Int. Cl.
*A61K 35/00* (2006.01)
*A61K 38/00* (2006.01)

(52) U.S. Cl. .............................. 424/185.1; 424/192.1; 514/2; 514/8

(58) Field of Classification Search ................ 530/350; 514/2, 8, 12; 424/192.1, 93, 185.1
See application file for complete search history.

(56) References Cited

U.S. PATENT DOCUMENTS

| | | | |
|---|---|---|---|
| 5,731,288 | A | 3/1998 | Markland et al. |
| 5,814,609 | A | 9/1998 | Markland et al. |
| 5,830,742 | A | 11/1998 | Black et al. |
| 5,922,546 | A | 7/1999 | Mayer et al. |
| 5,935,578 | A | 8/1999 | Alves et al. |
| 5,935,792 | A | 8/1999 | Rubin et al. |
| 6,013,466 | A | 1/2000 | Black et al. |
| 6,140,098 | A | 10/2000 | Balasubramanian et al. |
| 6,177,475 | B1 | 1/2001 | Tatarintsev et al. |
| 6,190,876 | B1 | 2/2001 | Rubin et al. |
| 6,255,064 | B1 | 7/2001 | Tindal et al. |
| 6,265,199 | B1 | 7/2001 | Sheppard et al. |
| 2002/0001840 | A1 | 1/2002 | Lopez-Otin et al. |

FOREIGN PATENT DOCUMENTS

| | | |
|---|---|---|
| WO | WO9907856 A1 | 2/1999 |
| WO | WO 99/23228 | 5/1999 |
| WO | WO 99/36549 | 7/1999 |
| WO | WO 99/41388 | 8/1999 |
| WO | WO 00/43525 | 7/2000 |
| WO | WO0043493 A2 | 7/2000 |
| WO | WO0174857 A2 | 10/2001 |

OTHER PUBLICATIONS

Fogarty M, Learning from Angiogenesis Trial Failures. The Scientist 16(6):33, Mar. 2002.*
Attwood TK. Genomics. The Babel of bioinformatics. Science. 290(5491):471-473, 2000.*
Skolnick et al. From genes to protein structure and function: novel applications of computational approaches in the genomic era. Trends Biotechnol. 18(1):34-9, 2000.*
Ngo J.T, Marks J. Karplus M., Computational complexity, protein structure prediction, and the Levinthal paradox in The Protein Folding Problem, ch. 14, pp. 435-508, Birkhauser, 1994.*
Fan et al Controlling the vasculature: angiogenesis, anti-angiogenesis and vascular targeting of gene therapy. Trends Pharmacol Sci. 16(2):57-66, 1995.*
Wallace RW. Media hype and drug discovery. Durg Discovery Today 10:433-434, 1998.*
Zhou et al Molecular cloning and functional expression of contortrostatin, a homodimeric disintegrin from southern copperhead snake venom. Arch Biochem Biophys. Mar. 15, 2000;375(2):278-88.*
Lu et al Preferential antagonism of the interactions of the integrin alpha IIb beta 3 with immobilized glycoprotein ligands by snake-venom RGD (Arg-Gly-Asp) proteins. . . . Biochem J. Dec. 15, 1994;304 ( Pt 3):929-36.*
Juliano et al. Disintegrin interaction with alpha V beta 3 integrin on human umbilical vein endothelial cells: expression of ligand induced binding site on beta 3 subunit. Exp Cell Res. May 25, 1996;225(1):132-42.*
Kuntz ID. Structure-based strategies for drug design and discovery. Science. Aug. 21, 1992;257(5073):1078-82.*
Miller et al Ligand binding to proteins: the binding landscape model. Protein Sci. Oct. 1997;6(10):2166-79.*
Nath D et al. "Interaction of metargidin (ADAM-15) with $\alpha_v\beta_3$ and $\alpha_5\beta_1$ integrins on different haemopoietic cells," *J. Cell Science* 112:579-587, 1999.
Yeh CH et al. "Accutin, a new disintegrin, inhibits angiogenesis in vitro and in vivo by acting as integrin $\alpha_v\beta_3$ antagonist and inducing apoptosis," *Blood* 92(9):3268-3276, Nov. 1, 1998.

(Continued)

*Primary Examiner*—Christina Chan
*Assistant Examiner*—Maher Haddad
(74) *Attorney, Agent, or Firm*—Julie K. Smith; Suzanne A. Sprunger

(57) ABSTRACT

The present invention provides methods and compositions for inhibiting the biological activity of integrins, for inhibiting endothelial cell migration. and for inhibiting angiogenesis. In particular, the invention provides compositions comprising ADAM disintegrin domains and methods for using said compositions. In preferred embodiments the methods and compositions of the invention are used to inhibit angiogenesis and to treat diseases or conditions mediated by angiogenesis.

29 Claims, No Drawings

OTHER PUBLICATIONS

Zhang X-P et al. "Specific Interaction of the recombinant disintegrin-like domain of MDC-15 (metargidin, ADAM-15) with integrin $\alpha_v\beta_3$," *J. Biological Chem.* 273(13):7345-7350, Mar. 27, 1998.

Hooft van Huijsvuijen, "ADAM 20 and 21; two novel human testis-specific membrane metalloproteases with similarity to fertilin-α," *Gene* 206(2):273-282, 1998.

National Cancer Institute, Cancer Genome Anatomy Project (CGAP), GenBank Accession No. AA758110, Dec. 1998.

Schluesener HJ, "The disintegrin domain of ADAM 8 enhances protection against rata experimental autoimmune encephalomyelitis, neuritis and uveitis by a polyvalent autoantigen vaccine,". *Neuroimmunology* 87 (1-2):197-202, Jul. 1998.

Sheu J-R, et al., "Inhibition of angiogenesis in vitro and in vivo: comparison of the relative activities of triflavin, an Arg-Gly-Asp—containing peptide and anti-alphavbeta3 integrin monoclonal antibody," *BBA-General Subjects, Elsevier Science Publishers, NL*, 1336(3):445-454, Oct. 1997.

Tselepi VH, et al., "An RGD to LDV Motif Conversion within the Disintegrin Kistrin Generates an Integrin Antagonist That Retains Potency but Exhibits Altered Receptor Specificity," *J. Biological Chem* 272(34):21341-21348, Aug. 1997.

Westkamp G, et al., "MDC9, a Widely Expressed Cellular Disintegrin Containing Cytoplasmic SH3 Ligand Domains," *J. Cell Biol.* 132(4):717-726, Feb. 1996.

Wolfsberg TG, et al., "ADAM, a Novel Family of Membrane Proteins Containing *A D*isintegrin *A*nd Mettaloprotease Domain: Multipotential Functions in Cell—Cell and Cell-Matrix Interactions," *J. Cell Biol.* 131(2):275-278, Oct. 1995.

Xu R, et al., "Molecular Cloning and Mapping of a Novel ADAM Gene(*ADAM29*) to Human Chromosome 4," *Genomics*, 62:537-539, 1999.

* cited by examiner

USE OF INTEGRIN ANTAGONISTS TO INHIBIT ANGIOGENESIS

CROSS REFERENCE TO RELATED APPLICATIONS

This application claims the benefit of pending U.S. provisional application Ser. No. 60/184,865, filed Feb. 25, 2000, the contents of which are incorporated herein by reference.

FIELD OF THE INVENTION

This invention relates to methods and compositions that are useful for antagonizing the interaction between integrins and their ligands. In particular, the invention relates to the use of ADAM disintegrin domains for antagonizing the interaction between integrins and their ligands.

BACKGROUND OF THE INVENTION

A. Integrins and Disintegrins

Integrins are a family of cell surface proteins that mediate adhesion between cells (cell-cell adhesion) and between cells and extracellular matrix proteins (cell-ECM adhesion). Integrins are heterodimeric structures composed of noncovalently bound $\alpha$ and $\beta$ subunits. In humans, at least fifteen different $\alpha$ subunits and eight different $\beta$ subunits combine to form integrins with diverse biological activities and ligand specificities. Integrins play important roles in biological processes including embryonic development, platelet aggregation, immune reactions, tissue repair and remodeling, bone resorption, and tumor invasion and metastasis. Integrins are, therefore, important targets for therapeutic intervention in human disease.

The disintegrins are a family of low molecular weight, soluble, cysteine-rich peptides which have been isolated from snake venom (reviewed in Niewiarowski et al., Seminars in Hematology 31(4):289, 1994). The snake venom disintegrins typically contain an RGD (Arg-Gly-Asp, SEQ ID NO:19) motif. The RGD motif is recognized by many integrins, and is present in several integrin ligands including fibronectin, vitronectin, and von Willebrand factor. Disintegrins disrupt normal adhesion processes by inhibiting the binding of cell surface integrins to their ligands.

Disintegrin-like domains have been identified in cellular proteins from both invertebrates and vertebrates (see, e.g., Westcamp and Blobel, Proc. Natl. Acad. Sci. USA 91:2748, 1994; Wolfsberg et al., Dev. Biol. 169:378, 1995; Alfandari et al., Dev. Biol. 182:314, 1997), including the ADAM family of transmembrane proteins.

B. ADAMs

The ADAMs, which have also been called MDCs, are a family of type I transmembrane cysteine-rich glycoproteins (Weskamp et al., Proc. Natl. Acad. Sci. USA, 91:2748, 1994; Wolfsberg et al., Dev. Biol. 169:378, 1995). The multidomain structure of the ADAMs typically includes an amino-terminal metalloprotease domain, a disintegrin domain, a cysteine-rich region (the region between the disintegrin domain and the transmembrane domain), a transmembrane region, and a cytoplasmic domain. At least 30 ADAM family members have been identified, in a variety of animal species. The structure of the ADAMs suggests that they may be involved in a variety of biological processes, including cell adhesion, cell fusion, signal transduction, and proteolysis. Members of the ADAM family have, in fact, been shown to play roles in sperm-egg binding and fusion, myotube formation, neurogenesis, and proteolysis.

ADAM-15, also called MDC-15 or metargidin, is the only ADAM identified to date which contains an RGD motif within its disintegrin domain. Zhang et al. (J. Biol. Chem. 273(13):7345, 1998) have reported that the isolated disintegrin domain of ADAM-15, expressed in E. coli as a glutathione S-transferase fusion protein, specifically interacts with $\alpha_v\beta_3$ integrin and that the interaction is mediated by the RGD tripeptide sequence. The recombinant fusion protein did not interact with other integrins tested, including $\alpha_{IIb}\beta_3$ and $\alpha_5\beta_1$. Nath et al. (J. Cell Science 112:579, 1999) have reported that the entire ADAM-15 extracellular domain, expressed as an Fc fusion protein in COS cells, interacts with $\alpha_v\beta_3$ and $\alpha_5\beta_1$ integrins on hematopoietic cells and that the interaction is mediated by the RGD tripeptide sequence. Zhang et al. and Nath et al. commented that the RGD-dependent interaction between ADAM-15 and $\alpha_v\beta_3$ integrin suggests a role in processes such as malignancy and angiogenesis.

C. Angiogenesis

Angiogenesis, the generation of new blood vessels, is a spatially and temporally regulated process in which endothelial and smooth muscle cells proliferate, migrate, and assemble into tubes, in response to endogenous positive and negative regulatory molecules. Angiogenesis plays important roles in both normal and pathological physiology.

Under normal physiological conditions, angiogenesis is involved in fetal and embryonic development, wound healing, organ regeneration, and female reproductive remodeling processes including formation of the endometrium, corpus luteum, and placenta. Angiogenesis is stringently regulated under normal conditions, especially in adult animals, and perturbation of the regulatory controls can lead to pathological angiogenesis.

Pathological angiogenesis has been implicated in the manifestation and/or progression of inflammatory diseases, certain eye disorders, and cancer. In particular, several lines of evidence support the concept that angiogenesis is essential for the growth and persistence of solid tumors and their metastases (see, e.g., Folkman, N. Engl. J. Med. 285:1182, 1971; Folkman et al., Nature 339:58, 1989; Kim et al., Nature 362:841, 1993; Hori et al., Cancer Res., 51:6180, 1991; Zetter, Annu. Rev. Med. 49:407, 1998). The formation of new blood vessels provides a growing tumor with oxygen, nutrients, waste removal, and a conduit by which invasive cells can enter the circulatory system and establish distant metastases. Various classes of angiogenesis inhibitors are presently being developed and tested for the prevention (e.g., treatment of premalignant conditions), intervention (e.g., treatment of small tumors), and regression (e.g., treatment of large tumors) of cancers (see, e.g., Bergers et al., Science 284:808, 1999) and other forms of pathological angiogenesis. Because many steps in the angiogenic process, including endothelial cell migration, proliferation, and morphogenesis require vascular cell adhesion, certain integrin antagonists have been tested as anti-angiogenic agents.

Several integrins are expressed on the surface of cultured endothelial and smooth muscle cells, including $\alpha_v\beta_3$ integrin. The $\alpha_v\beta_3$ integrin is an endothelial cell receptor for von Willebrand factor, fibrin, fibrinogen, and fibronectin, and a marker of angiogenic vascular tissue. Brooks et al. have reported that monoclonal antibodies to $\alpha_v\beta_3$ integrin, as well as cyclic peptide inhibitors, disrupt angiogenesis and that $\alpha_v\beta_3$ antibodies promote tumor regression (Science 264:569, 1994; Cell 79:1157, 1994). These results suggest that $\alpha_v\beta_3$ integrin is a useful therapeutic target for diseases characterized by pathological angiogenesis.

There is great need for additional compositions and methods of antagonizing the interaction between integrins and their ligands. In particular, there is great need for additional compositions and methods of inhibiting angiogenesis for the prevention, abrogation, and mitigation of disease processes that are dependent upon pathological angiogenesis.

SUMMARY OF THE INVENTION

The present invention is based upon the discovery that ADAM disintegrin domains are useful for inhibiting the biological activity of integrins and for inhibiting endothelial cell migration and angiogenesis, including the unexpected discovery that these inhibitory activities reside in ADAM disintegrin domains that lack an RGD motif.

The invention is directed to methods of antagonizing the binding of an integrin to its ligands, and thereby inhibiting the biological activity of the integrin, comprising contacting the integrin with an effective amount of an ADAM disintegrin domain polypeptide. The invention is further directed to methods of inhibiting endothelial cell migration and methods of inhibiting angiogenesis comprising administering an effective amount of an ADAM disintegrin domain polypeptide. In some embodiments the ADAM disintegrin domain polypeptide is in the form of a multimer, preferably a leucine zipper multimer or Fc polypeptide. In some embodiments the ADAM disintegrin domain is from a human ADAM, and preferably from ADAM-8, ADAM-9, ADAM-10, ADAM-15, ADAM-17, ADAM-20, ADAM-21, ADAM-22, ADAM-23, or ADAM-29. The ADAM disintegrin domain is preferably produced in a recombinant cell, and is preferably present in a composition comprising a pharmaceutically acceptable carrier.

In some preferred embodiments the ADAM disintegrin domain polypeptide comprises an amino acid sequence selected from the group consisting of: amino acids 23–264 of SEQ ID NO:2, amino acids 23–303 of SEQ ID NO:4, amino acids 23–235 of SEQ ID NO:6, amino acids 23–292 of SEQ ID NO:8, amino acids 23–216 of SEQ ID NO:10, amino acids 23–305 of SEQ ID NO:12, amino acids 23–293 of SEQ ID NO:14, amino acids 23–312 of SEQ ID NO:16, amino acids 23–310 of SEQ ID NO:18, and amino acids 23–298 of SEQ ID NO:22. In some more preferred embodiments the ADAM disintegrin domain polypeptide comprises an amino acid sequence selected from the group consisting of: amino acids 34–91 of SEQ ID NO:2, amino acids 34–92 of SEQ ID NO:4, amino acids 34–99 of SEQ ID NO:6, amino acids 34–92 of SEQ ID NO:8, amino acids 34–93 of SEQ ID NO:10, amino acids 34–91 of SEQ ID NO:12, amino acids 34–91 of SEQ ID NO:14, amino acids 34–92 of SEQ ID NO:16, amino acids 34–91 of SEQ ID NO:18, and amino acids 34–91 of SEQ ID NO:22. In some most preferred embodiments the ADAM disintegrin domain polypeptide comprises an amino acid sequence selected from the group consisting of: amino acids 78–91 of SEQ ID NO:2, amino acids 79–92 of SEQ ID NO:4, amino acids 87–99 of SEQ ID NO:6, amino acids 79–92 of SEQ ID NO:8, amino acids 79–93 of SEQ ID NO:10, amino acids 78–91 of SEQ ID NO:12, amino acids 78–91 of SEQ ID NO:14, amino acids 79–92 of SEQ ID NO:16, amino acids 78–91 of SEQ ID NO:18, and amino acids 78–91 of SEQ ID NO:22.

In some embodiments a therapeutically effective amount of the ADAM disintegrin domain is administered to a mammal in need of such treatment. In preferred embodiments the mammal is afflicted with a condition mediated by angiogenesis, an ocular disorder, malignant or metastatic condition, inflammatory disease, osteoporosis and other conditions mediated by accelerated bone resorption, restenosis, inappropriate platelet activation, recruitment, or aggregation, thrombosis, or a condition requiring tissue repair or wound healing. The ADAM disintegrin domain is, in some embodiments, administered in combination with radiation therapy and/or in combination with one or more additional therapeutic agents.

The invention also encompasses methods for identifying compounds that modulate integrin biological activity, that modulate the interaction between an integrin and an ADAM disintegrin domain, that inhibit endothelial cell migration, or that inhibit angiogenesis, comprising combining a test compound with an integrin or with endothelial cells and with an ADAM disintegrin domain polypeptide that binds to the integrin or endothelial cells and determining whether the test compound alters the binding of the ADAM disintegrin domain polypeptide to the integrin or endothelial cells.

These and other aspects of the present invention will become evident upon reference to the following detailed description, examples, and claims.

DETAILED DESCRIPTION OF THE INVENTION

A. Abbreviations and Terminology Used in the Specification

"4-1BB" and "4-1BB ligand" (4-1BB-L) are polypeptides described, inter alia, in U.S. Pat. No. 5,674,704, including soluble forms thereof.

"ADAMs" are a family of transmembrane glycoproteins having disintegrin and metalloproteinase domains, also called MDC, metalloprotease/disintegrin/cysteine-rich proteins.

"Dis" is a disintegrin domain; "ADAMdis" is an ADAM disintegrin domain.

"CD40 ligand" (CD40L) is a polypeptide described. inter alia. in U.S. Pat. No. 5,716,805, including soluble forms thereof.

"CD148" is a protein tyrosine phosphatase, also called DEP-1, ECRTP, and PTPRJ. CD148 binding proteins are described in Daniel et al., PCT Publication No. WO 00/15258, 23 Mar. 2000.

"DMEM" is Dulbecco's Modified Eagle Medium.

"FACS" is fluorescence activated cell sorting.

"Flt3L" is Flt3 ligand, a polypeptide described, inter alia, in U.S. Pat. No. 5,554,512, including soluble forms thereof.

"HRMEC" are human renal microvascular endothelial cells.

"HMVEC-d" are human dermal microvascular endothelial cells.

"mAb" is a monoclonal antibody.

"MDC" is a family of cysteine-rich proteins having metalloprotease and disintegrin domains, also called ADAM.

"Nectin-3" is a cell adhesion molecule in the nectin family (which is described, inter alia, in Satoh-Horikawa et al., J. Biol. Chem. 275(14):10291, 2000). The GenBank accession numbers of human nectin-3 nucleic acid and polypeptide sequences are AF282874 and AAF97597 respectively (Reymond et al., 2000).

"PMA" is phorbol-12-myristate-13-acetate.

"Tek," which has also been called Tie2 and ork, is an receptor tyrosine kinase (RTK) that is predominantly expressed in vascular endothelium. The molecular cloning of human Tek (ork) has been described by Ziegler, U.S. Pat. No. 5,447,860. "Tek antagonists" are described, inter alia, in Cerretti et al., PCT Publication No. WO 00/75323, 14 Dec. 2000.

"TNF" is tumor necrosis factor. "TNFR" is a tumor necrosis factor receptor, including soluble forms thereof. "TNFR/Fc" is a tumor necrosis factor receptor-Fc fusion polypeptide.

"TRAIL" is TNF-related apoptosis-inducing ligand, a type II transmembrane polypeptide in the TNF family described, inter alia, in U.S. Pat. No. 5,763,223, including soluble forms thereof.

"TWEAK" is TNF-weak effector of apoptosis, a type II transmembrane polypeptide in the TNF family described, inter alia, in Chicheportiche et al., J. Biol. Chem. 272(51): 32401, 1997, including soluble forms thereof. "TWEAK-R" is the "TWEAK receptor," which is described, inter alia, in U.S. Ser. Nos. 60/172,878 and 60/203,347 and Feng et al., Am. J. Pathol. 156(4):1253, 2000, including soluble forms thereof. TWEAK-R/Fc is a TWEAK receptor-Fc fusion polypeptide.

"VEGF" is vascular endothelial growth factor, also known as VPF or vascular permeability factor.

B. ADAM Polypeptides and ADAM Disintegrin Domain Polypeptides

At least thirty ADAMs have been described. Table 1 provides reference information for selected human ADAMs.

ADAM disintegrin domains show sequence homology to the snake venom disintegrins, and are characterized by a framework of cysteines. For example, a typical disintegrin sequence comprises a framework such as:

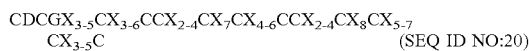

The sequences of several ADAM disintegrin domains are shown in Table 2 and in the Sequence Listing.

The present invention encompasses the use of various forms of ADAM disintegrin domains that retain at least one activity selected from the group consisting of integrin binding activity, inhibition of endothelial cell migration, and inhibition of angiogenesis. The term "ADAM disintegrin domain polypeptide" is intended to encompass polypeptides containing all or part of a native ADAM disintegrin domain, with or without other ADAM domains (such as the cysteine-rich region), as well as related forms including, but not limited to: (a) fragments, (b) variants, (c) derivatives, (d) fusion polypeptides, and (e) multimeric forms (multimers). The ability of these related forms to inhibit integrin binding endothelial cell migration, and/or inhibition of angiogenesis may be determined in vitro or in vivo by using methods such as those exemplified below or by using other assays known in the art.

TABLE 1

Selected Members of the ADAM Family

| ADAM | Other Names | GenBank Accession Number (Human) | Published Description |
|---|---|---|---|
| ADAM-8 | MS2, CD156 | D26579 | Genomics 41(I):56, 1997 |
| ADAM-9 | MDC9, meltrin gamma | U41766 | J. Cell. Biol. 132(4):717, 1996 |

TABLE 1-continued

Selected Members of the ADAM Family

| ADAM | Other Names | GenBank Accession Number (Human) | Published Description |
|---|---|---|---|
| ADAM-10 | MADM, kuzbanian, reprolysin | AF009615 | J. Biol. Chem. 272(39):24588, 1997 |
| ADAM-15 | Metargidin, MDC15 | U46005 | J. Biol. Chem. 271(9):4593, 1996 |
| ADAM-17 | TACE, cSVP | U86755 | WO 96/41624 |
| ADAM-20 | SVPH1–26 | AF029899 | WO 99/23228 |
| ADAM-21 | SVPH1–8 | AF029900 | WO 99/36549 |
| ADAM-22 | SVPH3–13, MDC2 | AB009671 | WO 99/41388 |
| ADAM-23 | SVPH3–17, MDC3 | AB009672 | WO 99/41388 |
| ADAM-29 | SVPH1 | AF171929 | Biochem. Biophys. Res. Commun. 263:810, 1999 |

The term "variant" includes polypeptides that are substantially homologous to native ADAM disintegrin domains, but which have an amino acid sequence different from that of a native ADAM disintegrin domain because of one or more deletions, insertions or substitutions. Particular embodiments include, but are not limited to, ADAM disintegrin domain polypeptides that comprise from one to ten deletions, insertions or substitutions of amino acid residues, when compared to a native ADAM disintegrin domain sequence. Included as variants of ADAM disintegrin domain polypeptides are those variants that are naturally occurring, such as allelic forms and alternatively spliced forms, as well as variants that have been constructed by modifying the amino acid sequence of a ADAM disintegrin domain polypeptide or the nucleotide sequence of a nucleic acid encoding a ADAM disintegrin domain polypeptide.

Generally, substitutions for one or more amino acids present in the native polypeptide should be made conservatively. Examples of conservative substitutions include substitution of amino acids outside of the active domain(s), and substitution of amino acids that do not alter the secondary and/or tertiary structure of the ADAM disintegrin domain. Additional examples include substituting one aliphatic residue for another, such as Ile, Val, Leu, or Ala for one another, or substitutions of one polar residue for another, such as between Lys and Arg; Glu and Asp; or Gln and Asn, or substitutions of one aromatic residue for another, such as Phe, Trp, or Tyr for one another. Other such conservative substitutions, for example, substitutions of entire regions having similar hydrophobicity characteristics, are known in the art.

In some preferred embodiments the ADAM disintegrin domain variant is at least about 70% identical in amino acid sequence to the amino acid sequence of a native ADAM disintegrin domain; in some preferred embodiments the ADAM disintegrin domain variant is at least about 80% identical in amino acid sequence to the amino acid sequence of a native ADAM disintegrin domain. In some more preferred embodiments the ADAM disintegrin domain variant is at least about 90% identical in amino acid sequence to the amino acid sequence of a native ADAM disintegrin domain; in some more preferred embodiments the ADAM disintegrin domain variant is at least about 95% identical in amino acid sequence to the amino acid sequence of a native ADAM disintegrin domain. In some most preferred embodiments the ADAM disintegrin domain variant is at least about 98% identical in amino acid sequence to the amino acid sequence of a native ADAM disintegrin domain; in some most preferred embodiments the ADAM disintegrin domain variant is at least about 99% identical in amino acid sequence to the amino acid sequence of a native ADAM disintegrin domain.

Percent identity, in the case of both polypeptides and nucleic acids, may be determined by visual inspection. Percent identity may be determined using the alignment method of Needleman and Wunsch (J. Mol. Biol. 48:443, 1970) as revised by Smith and Waterman (Adv. Appl. Math 2:482, 1981. Preferably, percent identity is determined by using a computer program, for example, the GAP computer program version 10.× available from the Genetics Computer Group (GCG; Madison, Wis., see also Devereux et al., Nucl. Acids Res. 12:387, 1984). The preferred default parameters for the GAP program include: (1) a unary comparison matrix (containing a value of 1 for identities and 0 for non-identities) for nucleotides, and the weighted comparison matrix of Gribskov and Burgess, Nucl. Acids Res. 14:6745, 1986, as described by Schwartz and Dayhoff, eds., Atlas of Protein Sequence and Structure, National Biomedical Research Foundation, pp. 353–358, 1979 for amino acids; (2) a penalty of 30 (amino acids) or 50 (nucleotides) for each gap and an additional 1 (amino acids) or 3 (nucleotides) penalty for each symbol in each gap; (3) no penalty for end gaps; and (4) no maximum penalty for long gaps. Other programs used by one skilled in the art of sequence comparison may also be used. For fragments of ADAM disintegrin domains, the percent identity is calculated based on that portion of ADAM disintegrin domain that is present in the fragment.

When a deletion or insertion strategy is adopted, the potential effect of the deletion or insertion on biological activity (such as integrin binding activity, inhibition of endothelial cell migration, or inhibition of angiogenesis) must be considered. Subunits of the inventive polypeptides may be constructed by deleting terminal or internal residues or sequences. Additional guidance as to the types of mutations that can be made is provided by a comparison of the sequence of ADAM disintegrin domain polypeptides to polypeptides that have similar structures, as well as by performing structural analysis of the inventive polypeptides.

The term "variant" also includes ADAM disintegrin domain polypeptides that are encoded by nucleic acids capable of hybridizing under moderately stringent conditions (e.g., prewashing solution of 5×SSC, 0.5% SDS, 1.0 mM EDTA (pH 8.0) and hybridization conditions of 50° C., 5×SSC, overnight) or higher stringency conditions to DNA sequences encoding ADAM disintegrin domain polypeptides, and which encode polypeptides that retain at least one activity selected from the group consisting of integrin binding activity, inhibition of endothelial cell migration, and inhibition of angiogenesis. The skilled artisan can determine additional combinations of salt and temperature that constitute moderate hybridization stringency. Conditions of higher stringency include higher temperatures for hybridization and post-hybridization washes, and/or lower salt concentration.

Mutations can be introduced into nucleic acids by synthesizing oligonucleotides containing a mutant sequence, flanked by restriction sites enabling ligation to fragments of the native sequence. Following ligation, the resulting reconstructed sequence encodes a variant having the desired amino acid insertion, substitution, or deletion. Alternatively, oligonucleotide-directed site-specific mutagenesis procedures can be employed to provide an altered gene having particular codons altered according to the substitution, deletion, or insertion required. The well known polymerase chain reaction (PCR) procedure also may be employed to generate and amplify a DNA sequence encoding a desired polypeptide or fragment thereof. Oligonucleotides that define the desired termini of the DNA fragment are employed as 5' and 3' primers. The oligonucleotides may additionally contain recognition sites for restriction endonucleases to facilitate insertion of the amplified DNA fragment into an expression vector.

The present invention further encompasses the use of ADAM disintegrin domain polypeptides with or without associated native-pattern glycosylation. ADAM disintegrin domain expressed in yeast or mammalian expression systems (e.g., COS-1 or COS-7 cells) may be similar to or significantly different from a native ADAM disintegrin domain polypeptide in molecular weight and glycosylation pattern, depending upon the choice of expression system. Expression of ADAM disintegrin domain polypeptides in bacterial expression systems, such as E. coli, provides non-glycosylated molecules. Different host cells may also process polypeptides differentially, resulting in heterogeneous mixtures of polypeptides with variable N- or C-termini.

The primary amino acid structure of ADAM disintegrin domain polypeptides may be modified to create derivatives by forming covalent or aggregative conjugates with other chemical moieties, such as glycosyl groups, lipids, phosphate, acetyl groups and the like. Covalent derivatives of ADAM disintegrin domain polypeptides may be prepared by linking particular functional groups to ADAM disintegrin domain amino acid side chains or at the N-terminus or C-terminus of a ADAM disintegrin domain polypeptide.

Fusion polypeptides of ADAM disintegrin domains that are useful in practicing the invention include covalent or aggregative conjugates of ADAMdis or its fragments with other polypeptides, such as by synthesis in recombinant culture as N-terminal or C-terminal fusions. One class of fusion polypeptides are discussed below in connection with ADAM disintegrin oligomers. As another example, a fusion polypeptide may comprise a signal peptide (which is also variously referred to as a signal sequence, signal, leader peptide, leader sequence, or leader) at the N-terminal region or C-terminal region of an ADAM disintegrin domain polypeptide which co-translationally or post-translationally directs transfer of the polypeptide from its site of synthesis to a site inside or outside of the cell membrane or cell wall. It is particularly advantageous to fuse a signal peptide that promotes extracellular secretion to the N-terminus of a soluble ADAMdis polypeptide. In this case, the signal peptide is typically cleaved upon secretion of the soluble polypeptide from the cell.

Secreted soluble polypeptides may be identified (and distinguished from its non-soluble membrane-bound counterparts) by separating intact cells which express the desired polypeptide from the culture medium, e.g., by centrifugation, and assaying the medium (supernatant) for the presence of the desired polypeptide. The presence of the desired polypeptide in the medium indicates that the polypeptide was secreted from the cells and thus is a soluble form of the polypeptide. Soluble polypeptides may be prepared by any of a number of conventional techniques. A DNA sequence encoding a desired soluble polypeptide may be subcloned into an expression vector for production of the polypeptide, or the desired encoding DNA fragment may be chemically synthesized.

Soluble ADAM disintegrin domain polypeptides comprise all or part of the ADAM disintegrin domain, with or without additional segments from the extracellular portion of the ADAM (such as the cysteine-rich region) but generally lack a transmembrane domain that would cause retention of the polypeptide at the cell surface. Soluble polypeptides may include part of the transmembrane domain or all or part of the cytoplasmic domain as long as the polypeptide is secreted from the cell in which it is produced. Examples of soluble ADAM disintegrin domain polypeptides are provided in the examples. In some preferred embodiments of the present invention, a multimeric form of a soluble ADAM disintegrin domain polypeptide is used to inhibit integrin binding to ligands and, hence, integrin biological activity. In some most preferred embodiments the soluble ADAM disintegrin domain polypeptide is used to inhibit endothelial cell migration and/or inhibit angiogenesis. These inhibitory activities may include both integrin-mediated and integrin-independent mechanisms.

ADAM disintegrin domain multimers are covalently-linked or non-covalently-linked multimers, including dimers, trimers, and higher multimers. Oligomers may be linked by disulfide bonds formed between cysteine residues on different ADAM disintegrin domain polypeptides. One embodiment of the invention is directed to multimers comprising multiple ADAM disintegrin domain polypeptides joined via covalent or non-covalent interactions between peptide moieties fused to the ADAM disintegrin domain polypeptides. Such peptides may be peptide linkers (spacers), or peptides that have the property of promoting multimerization. Leucine zippers and certain polypeptides derived from antibodies are among the peptides that can promote multimerization of ADAM disintegrin domain polypeptides attached thereto, as described in more detail below. In particular embodiments, the multimers comprise from two to four ADAM disintegrin domain polypeptides.

In some embodiments, a ADAM disintegrin domain multimer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al. (Proc. Natl. Acad. Sci. USA 88:10535, 1991); Byrn et al. (Nature 344:677, 1990); and Hollenbaugh and Aruffo ("Construction of Immunoglobulin Fusion Proteins", in *Current Protocols in Immunology*, Suppl. 4, pages 10.19.1–10.19.11, 1992).

A preferred embodiment of the present invention is directed to an ADAM disintegrin domain (ADAMdis) dimer comprising two fusion polypeptides created by fusing an ADAM disintegrin domain to an Fc polypeptide. A gene fusion encoding the ADAMdis-Fc fusion polypeptide is inserted into an appropriate expression vector. ADAMdis-Fc fusion polypeptides are expressed in host cells transformed with the recombinant expression vector, and allowed to assemble much like antibody molecules, whereupon interchain disulfide bonds form between the Fc moieties to yield divalent soluble ADAMdis polypeptides. The term "Fc polypeptide" as used herein includes native and mutein forms of polypeptides derived from the Fc region of an antibody. Truncated forms of such polypeptides containing the hinge region that promotes dimerization are also included.

One suitable Fc polypeptide, described in PCT application WO 93/10151, is a single chain polypeptide extending from the N-terminal hinge region to the native C-terminus of the Fc region of a human IgG 1 antibody. Another useful Fc polypeptide is the Fc mutein described in U.S. Pat. No. 5,457,035 and by Baum et al., EMBO J. 13:3992, 1994. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors. Fusion polypeptides comprising Fc moieties, and multimers formed therefrom, offer an advantage of facile purification by affinity chromatography over Protein A or Protein G columns, and Fc fusion polypeptides may provide a longer in vivo half life, which is useful in therapeutic applications, than unmodified polypeptides.

In other embodiments, a soluble ADAM disintegrin domain polypeptide may be substituted for the variable portion of an antibody heavy or light chain. If fusion proteins are made with both heavy and light chains of an antibody, it is possible to form an ADAM disintegrin domain multimer with as many as four soluble ADAM disintegrin domain polypeptides.

Alternatively, the ADAM disintegrin domain multimer is a fusion polypeptide comprising multiple ADAM disintegrin domain polypeptides, with or without peptide linkers (spacers), or peptides that have the property of promoting multimerization. Among the suitable peptide linkers are those described in U.S. Pat. Nos. 4,751,180 and 4,935,233. A DNA sequence encoding a desired peptide linker may be inserted between, and in the same reading frame as, the DNA sequences encoding ADAMdis, using conventional techniques known in the art. For example, a chemically synthesized oligonucleotide encoding the linker may be ligated between sequences encoding ADAMdis. In particular embodiments, a fusion protein comprises from two to four ADAM disintegrin domain polypeptides, separated by peptide linkers.

Another method for preparing ADAM disintegrin domain multimers involves use of a leucine zipper domain. Leucine zipper domains are peptides that promote multimerization of the proteins in which they are found. Leucine zippers were originally identified in several DNA-binding proteins (Landschulz et al., Science 240:1759, 1988), and have since been found in a variety of different proteins. Among the known leucine zippers are naturally occurring peptides and derivatives thereof that dimerize or trimerize. Examples of leucine zipper domains suitable for producing soluble oligomeric proteins are described in PCT application WO 94/10308, and the leucine zipper derived from lung surfactant protein D (SPD) described in Hoppe et al. FEBS Lett. 344:191, 1994. The use of a modified leucine zipper that allows for stable trimerization of a heterologous protein fused thereto is described in Fanslow et al., Semin. Immunol. 6:267, 1994. Recombinant fusion polypeptides comprising an ADAM disintegrin domain polypeptide fused to a leucine zipper peptide are expressed in suitable host cells, and the ADAM disintegrin domain multimer that forms is recovered from the culture supernatant.

C. Recombinant Production of ADAM Disintegrin Domain Polypeptides

The ADAM disintegrin domain polypeptides used in the present invention may be prepared using a recombinant expression system. Host cells transformed with a recombinant expression vector encoding the ADAM disintegrin domain polypeptide are cultured under conditions that promote expression of ADAM disintegrin domain and the ADAM disintegrin domain is recovered. ADAM disintegrin domain polypeptides can also be produced in transgenic plants or animals.

Any suitable expression system may be employed. Recombinant expression vectors include DNA encoding an ADAM disintegrin domain polypeptide operably linked to suitable transcriptional and translational regulatory nucleotide sequences, such as those derived from a mammalian, microbial, viral, or insect gene. Nucleotide sequences are operably linked when the regulatory sequence functionally relates to the ADAM disintegrin domain DNA sequence. Thus, a promoter nucleotide sequence is operably linked to an ADAM disintegrin domain DNA sequence if the promoter nucleotide sequence controls the transcription of the ADAM disintegrin domain DNA sequence. Examples of regulatory sequences include transcriptional promoters, operators, or enhancers, an mRNA ribosomal binding site, and appropriate sequences which control transcription and translation initiation and termination. A sequence encoding an appropriate signal peptide (native or heterologous) can be incorporated into expression vectors. A DNA sequence for a signal peptide (secretory leader) may be fused in frame to the ADAM disintegrin domain sequence so that the ADAM disintegrin domain polypeptide is initially translated as a fusion protein comprising the signal peptide. A signal peptide that is functional in the intended host cells promotes extracellular secretion of the ADAM disintegrin domain polypeptide. The signal peptide is cleaved from the ADAM disintegrin domain polypeptide upon secretion from the cell. Suitable host cells for expression of ADAM disintegrin domain polypeptides include prokaryotes, yeast and higher eukaryotic cells, including insect and mammalian cells. Appropriate cloning and expression vectors for use with bacterial, fungal, yeast, insect, and mammalian cellular hosts are known in the art.

Using the techniques of recombinant DNA including mutagenesis and the polymerase chain reaction (PCR), the skilled artisan can produce DNA sequences that encode ADAM disintegrin domain polypeptides comprising various additions or substitutions of amino acid residues or sequences, or deletions of terminal or internal residues or sequences, including ADAM disintegrin domain fragments, variants, derivatives, multimers, and fusion polypeptides.

The procedures for purifying expressed ADAM disintegrin domain polypeptides will vary according to the host system employed, and whether or not the recombinant polypeptide is secreted. ADAM disintegrin domain polypeptides may be purified using methods known in the art, including one or more concentration, salting-out, ion exchange, hydrophobic interaction, affinity purification, HPLC, or size exclusion chromatography steps. Fusion polypeptides comprising Fc moieties (and multimers formed therefrom) offer the advantage of facile purification by affinity chromatography over Protein A or Protein G columns.

D. Therapeutic Methods

The disclosed methods may be used to inhibit integrin binding and integrin biological activity, and to inhibit endothelial cell migration, and/or angiogenesis in a mammal in need of such treatment. The treatment is advantageously administered in order to prevent the onset or the recurrence of a disease or condition mediated by an integrin, or to treat a mammal that has a disease or condition mediated by an integrin.

Examples of the therapeutic uses of ADAM disintegrin domain polypeptides and compositions thereof include the treatment of individuals afflicted with conditions mediated by angiogenesis such as ocular disorders, dermatological disorders, and malignant or metastatic conditions, inflammatory diseases, osteoporosis and other conditions mediated by accelerated bone resorption, restenosis, inappropriate platelet activation, recruitment, or aggregation, thrombosis, or a condition requiring tissue repair or wound healing.

Among the ocular disorders that can be treated according to the present invention are eye diseases characterized by ocular neovascularization including, but not limited to, diabetic retinopathy (a major complication of diabetes), retinopathy of prematurity (this devastating eye condition, that frequently leads to chronic vision problems and carries a high risk of blindness, is a severe complication during the care of premature infants), neovascular glaucoma, retinoblastoma, retrolental fibroplasia, rubeosis, uveitis, macular degeneration, and corneal graft neovascularization. Other eye inflammatory diseases, ocular tumors, and diseases associated with choroidal or iris neovascularization can also be treated according to the present invention.

The present invention can also be used to treat malignant and metastatic conditions such as solid tumors. Solid tumors include both primary and metastatic sarcomas and carcinomas.

The present invention can also be used to treat inflammatory diseases including, but not limited to, arthritis, rheumatism, inflammatory bowel disease, and psoriasis.

Among the conditions mediated by inappropriate platelet activation, recruitment, aggregation, or thrombosis that can be treated according to the present invention are coronary artery disease or injury, myocardial infarction or injury following myocardial infarction, stroke, unstable angina, atherosclerosis, arteriosclerosis, preeclampsia, embolism, platelet-associated ischemic disorders including lung ischemia, coronary ischemia, and cerebral ischemia, restenosis following percutaneous coronary intervention including angioplasty, atherectomy, stent placement, and bypass surgery, thrombotic disorders including coronary artery thrombosis, cerebral artery thrombosis, intracardiac thrombosis, peripheral artery thrombosis, venous thrombosis, thrombosis and coagulopathies associated with exposure to a foreign or injured tissue surface, and reocclusion following thrombosis, deep venous thrombosis (DVT), pulmonary embolism (PE), transient ischemic attacks (TIAs), and another conditions where vascular occlusion is a common underlying feature. In some embodiments the methods according to the invention are used in individuals at high risk for thrombus formation or reformation, advanced coronary artery disease, or for occlusion, reocclusion, stenosis and/or restenosis of blood vessels, or stroke. In some embodiments the methods according to the invention are used in combination with angioplasty procedures, such as balloon angioplasty, laser angioplasty, coronary atherectomy or similar techniques, carotid endarterectomy, anastomosis of vascular grafts, surgery having a high risk of thrombus formation (i.e., coronary bypass surgery, insertion of a prosthetic valve or vessel and the like), atherectomy, stent placement, placement of a chronic cardiovascular device such as an in-dwelling catheter or prosthetic valve or vessel, organ transplantation, or bypass surgery.

Other diseases and conditions that can be treated according to the present invention include benign tumors and preneoplastic conditions, myocardial angiogenesis, hemophilic joints, scleroderma, vascular adhesions, asthma and allergy, eczema and dermatitis, graft versus host disease, sepsis, adult respirator distress syndrome, telangiectasia, and wound granulation.

The methods according to the present invention can be tested in in vivo animal models for the desired prophylactic or therapeutic activity, as well as to determine the optimal therapeutic dosage, prior to administration to humans.

The amount of a particular ADAM disintegrin domain polypeptide that will be effective in a particular method of treatment depends upon age, type and severity of the condition to be treated, body weight, desired duration of treatment, method of administration, and other parameters. Effective dosages are determined by a physician or other qualified medical professional. Typical effective dosages are about 0.01 mg/kg to about 100 mg/kg body weight. In some preferred embodiments the dosage is about 0.1–50 mg/kg; in some preferred embodiments the dosage is about 0.5–10 mg/kg. The dosage for local administration is typically lower than for systemic administration. In some embodiments a single administration is sufficient; in some embodiments the ADAM disintegrin domain is administered as multiple doses over one or more days.

The ADAM disintegrin domain polypeptides are typically administered in the form of a pharmaceutical composition comprising one or more pharmacologically acceptable carriers. Pharmaceutically acceptable carriers include diluents, fillers, adjuvants, excipients, and vehicles which are pharmaceutically acceptable for the route of administration, and may be aqueous or oleaginous suspensions formulated using suitable dispersing, wetting, and suspending agents.

Pharmaceutically acceptable carriers are generally sterile and free of pyrogenic agents, and may include water, oils, solvents, salts, sugars and other carbohydrates, emulsifying agents, buffering agents, antimicrobial agents, and chelating agents. The particular pharmaceutically acceptable carrier and the ratio of active compound to carrier are determined by the solubility and chemical properties of the composition, the mode of administration, and standard pharmaceutical practice.

The ADAM disintegrin domain polypeptides are administered to the patient in a manner appropriate to the indication. Thus, for example, ADAM disintegrin domain polypeptides, or pharmaceutical compositions thereof, may be administered by intravenous, transdermal, intradermal, intraperitoneal, intramuscular, intranasal, epidural, oral, topical, subcutaneous, intracavity, sustained release from implants, peristaltic routes, or by any other suitable technique. Parenteral administration is preferred.

In certain embodiments of the claimed invention, the treatment further comprises treating the mammal with one or more additional therapeutic agents. The additional therapeutic agent(s) may be administered prior to, concurrently with, or following the administration of the ADAM disintegrin domain polypeptide. The use of more than one therapeutic agent is particularly advantageous when the mammal that is being treated has a solid tumor. In some embodiments of the claimed invention, the treatment further comprises treating the mammal with radiation. Radiation, including brachytherapy and teletherapy, may be administered prior to, concurrently with, or following the administration of the ADAM disintegrin domain polypeptide and/or additional therapeutic agent(s).

In some preferred embodiments the method includes the administration of, in addition to an ADAM disintegrin domain polypeptide, one or more therapeutics selected from the group consisting of alkylating agents, antimetabolites, vinca alkaloids and other plant-derived chemotherapeutics, antitumor antibiotics, antitumor enzymes, topoisomerase inhibitors, platinum analogs, adrenocortical suppressants, hormones and antihormones, antibodies, immunotherapeutics, radiotherapeutics, and biological response modifiers.

In some preferred embodiments the method includes administration of, in addition to an ADAM disintegrin domain polypeptide, one or more therapeutics selected from the group consisting of cisplatin, cyclophosphamide, mechloretamine, melphalan, bleomycin, carboplatin, fluorouracil, 5-fluorodeoxyuridine, methotrexate, taxol, asparaginase, vincristine, and vinblastine, lymphokines and cytokines such as interleukins, interferons (alpha., beta. or delta.) and TNF, chlorambucil, busulfan, carmustine, lomustine, semustine, streptozocin, dacarbazine, cytarabine, mercaptopurine, thioguanine, vindesine, etoposide, teniposide, dactinomycin, daunorubicin, doxorubicin, bleomycin, plicamycin, mitomycin, L-asparaginase, hydroxyurea, methylhydrazine, mitotane, tamoxifen, fluoxymesterone, IL-8 inhibitors, angiostatin, endostatin, kringle 5, angiopoietin-2 or other antagonists of angiopoietin-1, antagonists of platelet-activating factor, antagonists of basic fibroblast growth factor, and COX-2 inhibitors.

In some preferred embodiments the method includes administration of, in addition to an ADAM disintegrin domain polypeptide, one or more therapeutic polypeptides, including soluble forms thereof, selected from the group consisting of Flt3 ligand, CD40 ligand, interleukin-2, interleukin-12, 4-1BB ligand, anti-4-1BB antibodies, TRAIL, TNF antagonists and TNF receptor antagonists including TNFR/Fc, Tek antagonists, TWEAK antagonists and TWEAK-R antagonists including TWEAK-R/Fc, VEGF antagonists including anti-VEGF antibodies, VEGF receptor (including VEGF-R1 and VEGF-R2, also known as Flt1 and Flk1 or KDR) antagonists. CD148 (also referred to as DEP-1, ECRTP, and PTPRJ, see Takahashi et al., J. Am. Soc. Nephrol. 10:2135–45, 1999; and PCT Publication No. WO 00/15258, 23 Mar. 2000) binding proteins, and nectin-3 antagonists.

In some preferred embodiments the ADAM disintegrin domain polypeptides of the invention are used as a component of, or in combination with, "metronomic therapy," such as that described by Browder et al. and Klement et al. (Cancer Research 60:1878, 2000; J. Clin. Invest. 105(8): R15, 2000; see also Baringa, Science 289:245, 2000).

As used herein, the terms "therapy," "therapeutic," "treat," and "treatment" generally include prophylaxis, i.e. prevention, in addition to therapy or treatment for an extant disease or condition. The methods of the present invention may be used as a first line treatment, for the treatment of residual disease following primary therapy, or as an adjunct to other therapies. Methods of measuring biological effectiveness are known in the art and are illustrated in the Examples below.

EXAMPLES

The following examples are intended to illustrate particular embodiments and not to limit the scope of the invention.

Example 1

ADAM Disintegrin Domain Polypeptides

This example describes one method for the recombinant production of ADAM disintegrin domain polypeptides.

Expression cassettes encoding an IgKappa leader sequence, ADAM disintegrin domain, and C-terminal Fc region were constructed in bacterial plasmids then transferred into eukaryotic expression vectors (pDC409, EMBO J. 10:2821, 1991, or another mammalian expression vector). The coding regions of the various constructs are summarized in Table 2. In addition to the disintegrin domain, these constructs encode additional portions of the extracellular portion of the ADAM (e.g. cysteine-rich region and EGF-like domain).

The expression vectors were transfected into COS-1, CV-1/EBNA, or 293/EBNA cells. Two days after transfection the cells were $^{35}$S labeled for four hours. Supernatants and total cell lysates were prepared and aliquots were immunoprecipitated using protein A-sepharose beads to capture the Fc tagged polypeptides. $^{35}$S labeled ADAM disintegrin-Fc polypeptides were run on 8–16% reducing gels and detected via autoradiography.

The cell type that produced the most soluble protein in the supernatant was used in a large scale (T-175 format, 20 flasks) transient transfection, and approximately one liter of supernatant was harvested after one week. ADAM disintegrin-Fc polypeptides were purified from the supernatants using affinity chromatography (protein A column). The polypeptides were characterized by determining the N-terminal amino acid sequence, amino acid composition, and protein integrity (SDS-PAGE under reducing and non-reducing conditions) before the polypeptides were used in FACS, immunoprecipitations, and biological assays such as those described below.

TABLE 2

ADAM Disintegrin Domain Polypeptide Constructs

| Construct | SEQ ID NOs: DNA/ polypeptide | IgK Lender[1,2] | ADAM disintegrin[1,3] (dis Framework)[1,4] | Fc Region[1] |
|---|---|---|---|---|
| ADAM-8dis-Fc | 1/2 | 1–20 | 23–264 (34–91) | 267–494 |
| ADAM-9dis-Fc | 3/4 | 1–20 | 23–303 (34–92) | 306–533 |
| ADAM-10dis-Fc | 5/6 | 1–20 | 23–235 (34–99) | 238–465 |
| ADAM-15dis-Fc | 7/8 | 1–20 | 23–292 (34–92) | 295–522 |
| ADAM-17dis-Fc | 9/10 | 1–20 | 23–216 (34–93) | 219–446 |
| ADAM-20dis-Fc | 11/12 | 1–20 | 23–305 (34–91) | 308–535 |
| ADAM-21dis-Fc | 13/14 | 1–20 | 23–293 (34–91) | 296–523 |
| ADAM-22dis-Fc | 15/16 | 1–20 | 23–312 (34–92) | 315–542 |
| ADAM-23dis-Fc | 17/18 | 1–20 | 23–310 (34–91) | 313–540 |
| ADAM-29dis-Fc | 21/22 | 1–20 | 23–298 (34–91) | 301–528 |

[1]residues in the polypeptide sequence
[2]the predicted cleavage site is after residue 20
[3]segment of the construct that includes ADAMdis, but may also contain additional ADAM sequences
[4]disintegrin framework, e.g., SEQ ID NO:20

Example 2

Binding of ADAM Disintegrin Domain Polypeptides to Cells

A. Binding to Endothelial Cells

This example describes a flow cytometric integrin mAb based binding inhibition assay, which is used to show binding of ADAM disintegrin-Fc polypeptides to integrins expressed on the surface of endothelial cells. Human endothelial cells express $\alpha_v\beta_3$, $\alpha_v\beta_5$, $\beta_1$, $\beta_4$, $\alpha_1$, $\alpha_2$, $\alpha_3$, $\alpha_4$, $\alpha_5$, and $\alpha_6$ integrins.

Primary human dermal microvascular endothelial cells (HMVEC-d) were maintained in supplemented endothelial growth medium (Clonetics Corporation, Walkersville, Md.). The ADAM disintegrin-Fc polypeptides produced in Example 1 were shown to bind specifically to HMVEC-d. Monoclonal antibodies specific for human integrins $\alpha_v\beta_3$ (LM609, anti CD51/61, Chemicon, Temecula, Calif. Brooks et al., Science 264:569, 1994), $\alpha_2\beta_1$ (BHA2.1 anti CD49b, Chemicon, Wang et al., Mol. Biol. of the Cell 9:865, 1998), $\alpha_5\beta_1$ (SAM-1 anti CD49e, Biodesign, A. te Velde et al., J. Immunol. 140:1548, 1988), $\alpha_3\beta_1$ (ASC-6 anti-CD49c, Chemicon, Pattaramalai et al., Exp. Cell. Res. 222: 281, 1996), $\alpha_4\beta_1$ (HP2/1 anti CD49d, Immunotech, Marseilles, France. Workshop of the 4th International Conference on Human Leukocyte Differentiation Antigens, Vienna Austria, 1989, workshop number p091), $\alpha_6\beta_1$ (GoH3 anti CD49f, Immunotech, Workshop 4th International Conference on Human Leukocyte Differentiation Antigens, workshop number p055), $\alpha_6\beta_4$ (439-9B anti CD104, Pharmingen, San Diego, Calif., Schlossman et al., 1995 Leukocyte Typing V: White Cell Differentiation Antigens. Oxford University Press, New York), and $\alpha_v\beta_5$ (MAB 1961, Chemicon International. monoclonal anti-human integrin $\alpha_v\beta_5$ mAb, IgG1 isotype, inhibits $\alpha_v\beta_5$ mediated binding/adhesion to vitronectin/fibronectin; Weinaker, et al., J. Biol. Chem. 269: 6940, 1994) were also shown to bind specifically to HMVEC-d. Each of these antibodies is known to specifically block binding of the indicated integrin to its ligands (e.g., fibronectin, vitronectin, fibrinogen). The ability of integrin mAbs to inhibit the binding of ADAM disintegrin-Fc polypeptides reveals which integrins the disintegrin domains bind and, indirectly, which integrin binding activities the disintegrin domains are able to antagonize. The ability of the antibodies to inhibit binding of the ADAM disintegrin-Fc polypeptides to endothelial cells was tested as described below.

Prior to performing binding studies, HMVEC-d were removed from culture vessels using trypsin-EDTA. The cells were washed in media containing serum and resuspended in binding medium which consisted of PBS containing 1 mM Ca2+, 1 mM Mg2+ and 0.5 mM Mn2+, 0.1% sodium azide, 10% Normal goat serum, 2% rabbit serum and 2% fetal bovine serum. Under these binding conditions, ADAM-8, -9, -10, -15, -17, -20, -21 -22, -23, and -29dis-Fc all bind to human endothelial cells.

One hundred microliters of cell suspension, containing 200,000 to 500,000 HMVEC-d, were added to 12×75 mm plastic test tubes. Monoclonal antibodies specific for one of the integrins, or a control monoclonal antibody (CD29 or M15), were added to the cell suspensions at a concentration of 100 μg/ml (5–8 fold mass excess) 15 minutes prior to addition of disintegrin-Fc fusion proteins. ADAM disintegrin-Fc polypeptides and control Fc fusion polypeptides (P7.5II.Fc) were added, at various concentrations from 12.5 to 20 μg/ml, to the cell suspensions and incubated for 1 hour at 30° C. Unbound Fc polypeptides were washed away by centrifugation of cells in 2 mls of binding media. The washed cell pellets were resuspended in binding medium and then incubated at 30° C. for 30 minutes with goat anti-human Fc-specific biotinylated antibody at a concentration of 2.5 μg/ml for 30 minutes. After centrifugation and washing of the cell pellets, the cells were resuspended in binding medium and bound anti-human Fc-biotin was detected by adding streptavidin-phycoerythrin conjugate to the cell suspension at a 1:1000 dilution (1 μg/ml) and incubating at 30° C. for 30 minutes. The unbound streptavidin-phycoerythrin was washed away and the cells were resuspended in binding medium containing propidium iodide. The level of fluorescent binding (disintegrin-Fc binding) was determined by flow cytometry.

The level of binding of each ADAM disintegrin-Fc polypeptide was determined in the presence of anti-integrin specific mAb and in the presence of control mAb. Both the intensity of binding (MFI) and the percentage of cells binding were determined. Percent inhibition was calculated using the formula [1-(MFI control-MFI integrin mAb)/MFI control. The results of these studies are summarized in Table 3.

ADAM-15, -17, -20 and -22 disintegrin domain polypeptides bound to $\alpha_v\beta_3$; ADAM 23 disintegrin domain polypeptide bound to $\alpha_2\beta_1$; ADAM-15, -21, -22 and -23 disintegrin domain polypeptides bound to $\alpha_5\beta_1$; ADAM-10, -17, -22 and -23 disintegrin domain polypeptides bound to the $\alpha_6$ integrins; ADAM-10 and -15 disintegrin domain polypeptides bound to $\alpha_v\beta_5$. An excess of a non blocking $\alpha_v\beta_5$ antibody did significantly affect the binding of ADAM-10, -22, and -23 disintegrin polypeptides to endothelial cells, suggesting that these ADAMdis polypeptides interact with integrin sites other than or in addition to the ligand (e.g., fibronectin, vitronectin) binding site. Based upon results from a different type of assay, Cal et al. have reported that the ADAM-23 disintegrin domain interacts with the $\alpha_v\beta_3$ integrin through an RGD-independent mechanism (Molec. Biol. of the Cell 11:1457, 2000).

Binding experiments are repeated using other ADAM disintegrin domains and other monoclonal antibodies. ADAM disintegrin-Fc polypeptides that bind to selected integrins are further tested for the ability to disrupt integrin-ligand interactions and to modulate endothelial cell function, angiogenesis, and other biological activities in vitro and in vivo.

B. Binding to Primary Human T-Cells

Primary human T-cells were purified from whole blood. These cells were used in FACS experiments to assess cell surface binding of purified ADAMdis-Fc polypeptides. ADAMdis-Fc binding was assessed with and without Con A (5 µg/ml) or immobilized OTK3 antibody (1 mg/ml, immobilized for 1 hour, 37° C.) stimulation. ADAMdis-Fc polypeptides (20 µg/ml) were bound at either 4° C. or 30° C. in the presence of cations (Ca++, Mg++, Mn++, 0.5 mM each). Cell surface integrin expression was assessed using a panel of murine and rat anti-human integrin antibodies. $\alpha_v\beta_5$, $\alpha_1$, $\alpha_3$, $\alpha_4$, $\alpha_6$, $\beta_1$, and $\beta_7$ integrins were detected on the surface of these cells. ADAMdis-Fc polypeptides did not bind to primary human T-cells at 4° C. ADAM-8-, ADAM-9-, ADAM-15-, ADAM-20-, ADAM-21-, ADAM-22-, and ADAM-23-dis-Fc polypeptides did bind primary T-cells at 30° C. with Con A stimulation. ADAMdis-Fc binding was not inhibited by a three-fold molar excess of antibodies to the integrins listed above.

C. Binding to Resting Platelets

Binding of ADAMdis-Fc polypeptides to citrated washed resting platelets was performed at 4° C. or 30° C. Binding was analyzed by flow cytometry using a biotinylated-anti-human Fc specific antibody and streptavidin-PE. Resting platelets express the integrins CD41/CD61 and CD49e. ADAM-9dis-Fc and ADAM-8dis-Fc bound resting platelets at 30° C. but not at 4° C. ADAM-9dis-Fc binding to resting platelets at 30° C. was not inhibited by a ten-fold excess of CD41a mAb.

Example 3

Activity of ADAM Disintegrin Domain Polypeptides in a Wound Closure Assay

A planar endothelial cell migration (wound closure) assay was used to quantitate the inhibition of angiogenesis by ADAM disintegrin-Fc polypeptides in vitro. In this assay, endothelial cell migration is measured as the rate of closure of a circular wound in a cultured cell monolayer. The rate of wound closure is linear, and is dynamically regulated by agents that stimulate and inhibit angiogenesis in vivo.

Primary human renal microvascular endothelial cells, HRMEC, were isolated, cultured, and used at the third passage after thawing, as described in Martin et al., In Vitro Cell Dev Biol 33:261, 1997. Replicate circular lesions, "wounds," (600–800 micron diameter) were generated in confluent HRMEC monolayers using a silicon-tipped drill press. At the time of wounding the medium (DMEM +1% BSA) was supplemented with 20 ng/ml PMA (phorbol-12-myristate-13-acetate), a range of concentrations of ADAM disintegrin-Fc polypeptide, or combinations of PMA and ADAM disintegrin-Fc polypeptide. The residual wound area was measured as a function of time (0–12 hours) using a microscope and image analysis software (Bioquant, Nashville, Tenn.). The relative migration rate was calculated for each agent and combination of agents by linear regression of

TABLE 3

Binding of ADAM Disintegrin-Fc Polypeptides to Integrins Expressed on Human Endothelial Cells

| ADAM | Integrin Binding[1] (+ or − or ND, not done) and Percent (%) Binding[2] | | | | | | |
|---|---|---|---|---|---|---|---|
| | $\alpha_v\beta_3$ | $\alpha_2\beta_1$ | $\alpha_3\beta_1$ | $\alpha_4\beta_1$ | $\alpha_5\beta_1$ | $\alpha_6\beta_1, \alpha_6\beta_4$ | $\alpha_v\beta_5$ |
| ADAM-8 | ND | ND | −(<10) | −(<10) | ND | ND | −(<20) |
| ADAM-9 | −(<10) | −(<10) | −(<10) | −(<20) | −(<10) | −(<10) | −(<10) |
| ADAM-10 | −(<10) | −(<10) | −(<10) | −(<20) | −(<10) | +(48) | +(25) |
| ADAM-15 | +(60) | −(<10) | −(<10) | −(<20) | +(30) | −(<10) | +(25) |
| ADAM-17 | +(50) | −(<10) | −(<10) | −(<10) | −(<10) | +(69) | −(<10) |
| ADAM-20 | +(58) | −(<10) | −(<10) | −(<10) | −(<20) | −(<10) | −(<10) |
| ADAM-21 | −(<10) | −(<10) | −(<10) | −(<10) | +(54) | −(<10) | −(<10) |
| ADAM-22 | +(42) | −(<10) | −(<10) | −(<10) | +(36) | +(32) | −(<10) |
| ADAM-23 | −(<10) | +(22) | −(<10) | −(<10) | +(49) | +(31) | −(<10) |

[1]positive binding defined as >20% binding inhibition; normal background variation 5–10%, baseline positive approx. 2X over background
[2]percent inhibition of binding by ADAM-dis-Fc in the presence of 5–8 fold excess integrin mAb as compared to control mAb residual wound area plotted over time. The inhibition of PMA-induced endothelial migration by ADAM disintegrin-Fc polypeptides is shown in Table 4.

The effect of ADAM-dis-Fc polypeptides on EGF-induced migration was also determined. For these experiments ECIF (epidermal growth factor, 40 ng/ml) was added to the medium, instead of PMA, at the time of wounding. The results are shown in Table 5.

micropockets created in the corneal epithelium of anesthetized mice. Vascularization is measured as the appearance, density, and extent of vessel ingrowth from the vascularized corneal limbus into the normally avascular cornea.

Hydron pellets, as described in Kenyon et al., Invest Opthamol. & Visual Science 37:1625, 1996, incorporate sucralfate with bFGF (90 ng/pellet), bFGF and IgG (11 μg/pellet, control), or bFGF and a range of concentrations of

TABLE 4

Effect of ADAM-15, -17, -20, and -23dis-Fc Polypeptides in PMA-Induced Endothelial Cell Wound Closure Migration Assay

| Expt. ID | No Addition | PMA 20 ng/ml | PMA + IgG | PMA + ADAM-15dis-Fc | PMA + ADAM-17dis-Fc | PMA + ADAM-20dis-Fc | PMA + ADAM-23dis-Fc |
|---|---|---|---|---|---|---|---|
| HL-H-142 15 μg/ml dis-Fc | 0.0436[1] (0.0016)[2] | 0.0655 (0.0004) | | | | 0.0499 (0.0009) 72%[3] | |
| HL-H-147 15 μg/ml dis-Fc | 0.0244 (0.0023) | 0.0424 (0.0002) | 0.0449 (0.0012) 0% | 0.0357 (0.0007) 37% | | | 0.0225 (0.0022) 100% |
| HL-H-153 15 μg/ml dis-Fc | 0.0253 0.00013 | 0.0460 (0.0022) | 0.0491 (0.006) 0% | | 0.0392 (0.0016) 33% | 0.0388 (0.005) 36% | 0.0317 (0.005) 70% |
| HL-H-154 15 μg/ml dis-Fc | 0.0119 (0.0012) | 0.0312 (0.0016) | | | 0.0283 (0.0008) 15% | 0.0160 (0.0017) 79% | |

[1]Slopes to average triplicate Y values and treat as a single data point in order to test whether the slopes are significantly different
[2]Data in parentheses is the +/− standard error of slopes
[3]Percent inhibition compared to migration rate observed in the presence of PMA

TABLE 5

Effect of ADAM-17, -20, and -23dis-Fc Polypeptides in EGF-Induced Endothelial Cell Wound Closure Migration Assay

| Expt. ID | No Addition | EGF 40 ng/ml | EGF + IgG | EGF + ADAM-17dis-Fc | EGF + ADAM-20dis-Fc | EGF + ADAM-23dis-Fc |
|---|---|---|---|---|---|---|
| HL-H-154 15 μg/ml dis-Fc | 0.0119 (0.0012) | 0.0378 (0.0061) | | 0.0242 (0.0029) 53% | 0.0172 (0.0031) 80% | 0.0310 (0.0036) 26% |
| HL-H-155 9 μg/ml dis-Fc | 0.0164 (0.0010) | 0.0468 (0.0059) | 0.0454 (0.0052) 5% | 0.0412 (0.0107) 18% | 0.0227 (0.0035) 79% | 0.0207 (0.0016) 86% |

[1]Slopes to average triplicate Y values and treat as a single data point in order to test whether the slopes are significantly different
[2]Data in parentheses is the +/− standard error of slopes
[3]Percent inhibition compared to migration rate observed in the presence of EGF alone ADAM-20 and -23dis-Fc polypeptides showed the greatest inhibition of both EGF- and PMA-induced endothelial migration at 15 μg/ml. ADAM-15 and -17dis-Fc polypeptides were less effective at inhibiting endothelial cell migration at 15 μg/ml. Hu IgG did not inhibit EGF- or PMA-induced endothelial cell migration in any of the experiments performed where it was included as a control Fc protein.

Example 4

Activity of ADAM Disintegrin Domain Polypeptides in a Corneal Pocket Assay

A mouse corneal pocket assay is used to quantitate the inhibition of angiogenesis by ADAM disintegrin-Fc polypeptides in vivo. In this assay, agents to be tested for angiogenic or anti-angiogenic activity are immobilized in a slow release form in a hydron pellet, which is implanted into ADAM disintegrin-Fc polypeptide. The pellets are surgically implanted into corneal stromal micropockets created by micro-dissection 1 mm medial to the lateral corneal limbus of 6–8 week old male C57BL mice. After five days, at the peak of neovascular response to bFGF, the corneas are photographed, using a Zeiss slit lamp, at an incipient angle of 35–50° from the polar axis in the meridian containing the pellet. Images are digitized and processed by subtractive color filters (Adobe Photoshop 4.0) to delineate established microvessels by hemoglobin content. Image analysis software (Bioquant, Nashville, Tenn.) is used to calculate the fraction of the corneal image that is vascularized, the vessel density within the vascularized area, and the vessel density within the total cornea. The inhibition of bFGF-induced corneal angiogenesis, as a function of the dose of ADAM disintegrin-Fc polypeptide, is determined.

Example 5

Inhibition of Neovascularization by ADAM Disintegrin Domain Polypeptides in a Murine Transplant Model Survival of heterotopically transplanted cardiac tissue from one mouse donor to the ear skin of another genetically similar mouse requires adequate neovascularization by the transplanted heart and the surrounding tissue, to promote survival and energy for cardiac muscle function. Inadequate vasculature at the site of transplant causes excessive ischemia to the heart, tissue damage, and failure of the tissue to engraft. Agents that antagonize factors involved in endothelial cell migration and vessel formation can decrease angiogenesis at the site of transplant, thereby limiting graft tissue function and ultimately engraftment itself. A murine heterotopic cardiac isograft model is used to demonstrate the antagonistic effects of ADAM disintegrin-Fc polypeptides on neovascularization. Female BALB/c (≈12 weeks of age) recipients are given neonatal heart grafts from donor mice of the same strain. The donor heart tissue is grafted into the left ear pinnae of the recipient on day 0 and the mice are divided into two groups. The control group receives human IgG (Hu IgG) while the other group receives ADAM disintegrin-Fc polypeptide, both intraperitoneally. The treatments are continued for five consecutive days. The functionality of the grafts is determined by monitoring visible pulsatile activity on days 7 and 14 post-engraftment. The inhibition of functional engraftment, as a function of the dose of ADAM disintegrin-Fc polypeptide, is determined. The histology of the transplanted hearts is examined is order to visualize the effects of ADAM disintegrin-Fc polypeptides on edema at the site of transplant and host and donor tissue vasculature (using, e.g., Factor VIII staining).

Example 6

Treatment of Tumors with ADAM Disintegrin Domain Polypeptides

ADAM disintegrin-Fc polypeptides are tested in animal models of solid tumors. The effect of the ADAM disintegrin-Fc polypeptides is determined by measuring tumor frequency and tumor growth.

The biological activity of ADAM disintegrin-Fc polypeptides is also demonstrated in other in vitro, ex vivo, and in vivo assays known to the skilled artisan, such as calcium mobilization assays and assays to measure platelet activation, recruitment, or aggregation.

The relevant disclosures of publications cited herein are specifically incorporated by reference. The examples presented above are not intended to be exhaustive or to limit the scope of the invention. The skilled artisan will understand that variations and modifications and variations are possible in light of the above teachings, and such modifications and variations are intended to be within the scope of the invention.

We claim:

1. A method of inhibiting angiogenesis in a mammal in need of such treatment, comprising administering to the mammal an inhibition-effective amount of an ADAM-20 disintegrin domain polypeptide, wherein the ADAM-20 disintegrin domain polypeptide comprises an amino acid sequence selected from the group consisting of:
   (a) amino acids 34–91 of SEQ ID NO:12; and
   (b) amino acids 23–305 of SEQ ID NO:12, wherein the ADAM-20 disintegrin polypeptide retains inhibition of angiogenesis activity.

2. The method of claim 1, wherein the mammal is afflicted with a malignant condition.

3. The method of claim 1, wherein the ADAM-20 disintegrin domain is in the form of a multimer.

4. The method of claim 3, wherein the multimer is a dimer or trimer.

5. The method of claim 3, wherein the multimer comprises an Fc polypeptide or a leucine zipper.

6. The method of claim 1, wherein the ADAM-20 disintegrin domain is from a human ADAM-20.

7. The method of claim 1, wherein the ADAM-20 disintegrin domain polypeptide has been produced by culturing a recombinant cell which comprises a nucleic acid that encodes the ADAM-20 disintegrin domain polypeptide under conditions permitting expression of the ADAM-20 disintegrin domain polypeptide, and recovering the ADAM-20 disintegrin domain polypeptide.

8. The method of claim 1, wherein the ADAM-20 disintegrin domain polypeptide is present in a composition comprising a pharmaceutically acceptable carrier.

9. The method of claim 1, wherein the mammal has a disease or condition mediated by angiogenesis, wherein the disease or condition is a solid tumor.

10. The method of claim 1, wherein the method further comprises treating the mammal with radiation.

11. The method of claim 1, wherein the method further comprises treating the mammal with a second therapeutic agent.

12. The method of claim 11, wherein the second therapeutic agent is selected from the group consisting of alkylating agents, antimetabolites, vinca alkaloids and other plant-derived chemotherapeutics, antitumor antibiotics, antitumor enzymes, topoisomerase inhibitors, platinum analogs, adrenocortical suppressants, hormones and antihormones, antibodies, immunotherapeutics, radiotherapeutics, and biological response modifiers.

13. The method of claim 11, wherein the second therapeutic agent is selected from the group consisting of cisplatin, cyclophosphamide, bleomycin, carboplatin, fluorouracil, 5-fluorouracil, 5-fluorodeoxyuridine, methotrexate, taxol, asparaginase, vincristine, vinblastine, mechloretamine, melphalan, 5-fluorodeoxyuridine, lymphokines and cytokines interleukins, interferons, TNF, chlorambucil, busulfan, carmustine, lomustine, semustine, streptozocin, dacarbazine, cytarabine, mercaptopurine, thioguanine, vindesine, etoposide, teniposide, dactinomycin, daunorubicin, doxorubicin, bleomycin, plicamycin, mitomycin, L-asparaginase, hydroxyurea, methylhydrazine, mitotane, tamoxifen, fluoxymesterone, and COX-2 inhibitors.

14. The method of claim 11, wherein the second therapeutic agent is a polypeptide, including soluble forms thereof, selected from the group consisting of Flt3 ligand, CD40 ligand, interleukin-2, interleukin-12, 4-1BB ligand, anti-4-1BB antibodies, TRAIL, TNF antagonists and TNF receptor antagonists including TNFR/Fc, Tek antagonists, TWEAK antagonists and TWEAK-R antagonists including TWEAK-R/Fc, VEGF antagonists including anti-VEGF antibodies, VEGF receptor antagonists, CD148 binding proteins, and nectin-3 antagonists.

15. The method of claim 1, wherein the ADAM-20 disintegrin domain is administered parenterally.

16. The method of claim 1, wherein the mammal is afflicted with retinoblastoma.

17. The method of claim 16, wherein the retinoblastoma is characterized by ocular neovascularization.

18. The method of claim 7, wherein the recombinant cell is a prokaryotic cell.

19. The method of claim 18, wherein the prokaryotic cell is an *E. coli* cell.

20. The method of claim 7, wherein the recombinant cell is a plant cell.

21. The method of claim 7, wherein the recombinant cell is a fungal cell.

22. The method of claim 7, wherein the recombinant cell is a yeast cell.

23. The method of claim 7, wherein the recombinant cell is an animal cell.

24. The method of claim 23, wherein the animal cell is an insect cell.

25. The method of claim 23, wherein the animal cell is a mammalian cell.

26. The method of claim 25, wherein the mammalian cell is selected from the group consisting of COS-1 cells and COS-7 cells.

27. The method of claim 9, wherein the solid tumor is selected from the group consisting of sarcomas and carcinomas.

28. A method of inhibiting angiogenesis in a mammal in need of such treatment, comprising administering to the mammal an inhibition-effective amount of a fusion polypeptide comprising the ADAM-20 disintegrin domain polypeptide of claim 1, wherein said fusion polypeptide retains inhibition of angiogenesis activity.

29. The method of claim 28, wherein said fusion polypeptide consists of the amino acid sequence of SEQ ID NO:12.

* * * * *

SEQUENCE LISTING

```
<160> NUMBER OF SEQ ID NOS: 22

<210> SEQ ID NO 1
<211> LENGTH: 1700
<212> TYPE: DNA
<213> ORGANISM: Artificial Sequence
<220> FEATURE:
<223> OTHER INFORMATION: Fusion Construct
<221> NAME/KEY: CDS
<222> LOCATION: (118)..(1602)
<223> OTHER INFORMATION:

<400> SEQUENCE: 1 gggtttccc  agtcacgacg  ttgtaaaacg  acggccagtg  aattgtaata  cgactcacta      60
tagggcgaat  tgggtaccgg  gccccccctc  gaggtcgacc  caagctggct  agccacc       117 atg gag aca gac aca ctc ctg cta tgg gta ctg ctc tgg gtt cca              165
Met Glu Thr Asp Thr Leu Leu Leu Trp Val Leu Leu Trp Val Pro
1               5                   10                  15 ggt tcc act ggt act agt tgt ggg aac ctg ttt gtg gag cgt ggg gag          213
Gly Ser Thr Gly Thr Ser Cys Gly Asn Leu Phe Val Glu Arg Gly Glu
                20                  25                  30 cag tgc gac tgc ggc ccc ccc gag gac tgc cgg aac cgc tgc tgc aac          261
Gln Cys Asp Cys Gly Pro Pro Glu Asp Cys Arg Asn Arg Cys Cys Asn
            35                  40                  45 tct acc acc tgc cag ctg gct gag ggg gcc cag tgt gcg cac ggt acc          309
Ser Thr Thr Cys Gln Leu Ala Glu Gly Ala Gln Cys Ala His Gly Thr
        50                  55                  60 tgc tgc cag gag tgc aag gtg aag ccg gct ggt gag ctg tgc cgt ccc          357
Cys Cys Gln Glu Cys Lys Val Lys Pro Ala Gly Glu Leu Cys Arg Pro
65                  70                  75                  80 aag aag gac atg tgt gac ctc gag gag ttc tgt gac ggc cgg cac cct          405
```

-continued

```
Lys Lys Asp Met Cys Asp Leu Glu Glu Phe Cys Asp Gly Arg His Pro
             85                  90                  95 gag tgc ccg gaa gac gcc ttc cag gag aac ggc acg ccc tgc tcc ggg         453
Glu Cys Pro Glu Asp Ala Phe Gln Glu Asn Gly Thr Pro Cys Ser Gly
            100                 105                 110 ggc tac tgc tac aac ggg gcc tgt ccc aca ctg gcc cag cag tgc cag         501
Gly Tyr Cys Tyr Asn Gly Ala Cys Pro Thr Leu Ala Gln Gln Cys Gln
            115                 120                 125 gcc ttc tgg ggg cca ggt ggg cag gct gcc gag gag tcc tgc ttc tcc         549
Ala Phe Trp Gly Pro Gly Gly Gln Ala Ala Glu Glu Ser Cys Phe Ser
        130                 135                 140 tat gac atc cta cca ggc tgc aag gcc agc cgg tac agg gct gac atg         597
Tyr Asp Ile Leu Pro Gly Cys Lys Ala Ser Arg Tyr Arg Ala Asp Met
145                 150                 155                 160 tgt ggc gtt ctg caa tgt aaa ggt ggt caa caa cct tta ggt aga gct         645
Cys Gly Val Leu Gln Cys Lys Gly Gly Gln Gln Pro Leu Gly Arg Ala
                165                 170                 175 ata tgt att gtc gac gtg tgc cac gcg ctc acc aca gag gat ggc act         693
Ile Cys Ile Val Asp Val Cys His Ala Leu Thr Thr Glu Asp Gly Thr
                180                 185                 190 gcg tat gaa cca gtg ccc gag ggc acc cgg tgt gga cca gag aag gtt         741
Ala Tyr Glu Pro Val Pro Glu Gly Thr Arg Cys Gly Pro Glu Lys Val
            195                 200                 205 tgc tgg aaa gga cgt tgc cag gac tta cac gtt tac aga tcc agc aac         789
Cys Trp Lys Gly Arg Cys Gln Asp Leu His Val Tyr Arg Ser Ser Asn
        210                 215                 220 tgc tct gcc cag tgc cac aac cat ggg gtg tgc aac cac aag cag gag         837
Cys Ser Ala Gln Cys His Asn His Gly Val Cys Asn His Lys Gln Glu
225                 230                 235                 240 tgc cac tgc cac gcg ggc tgg gcc ccg ccc cac tgc gcg aag ctg ctg         885
Cys His Cys His Ala Gly Trp Ala Pro Pro His Cys Ala Lys Leu Leu
                245                 250                 255 act gag gtg cac gca gcg tcc ggg aga tct tgt gac aaa act cac aca         933
Thr Glu Val His Ala Ala Ser Gly Arg Ser Cys Asp Lys Thr His Thr
                260                 265                 270 tgc cca ccg tgc cca gca cct gaa gcc gag ggc gcg ccg tca gtc ttc         981
Cys Pro Pro Cys Pro Ala Pro Glu Ala Glu Gly Ala Pro Ser Val Phe
            275                 280                 285 ctc ttc ccc cca aaa ccc aag gac acc ctc atg atc tcc cgg acc cct        1029
Leu Phe Pro Pro Lys Pro Lys Asp Thr Leu Met Ile Ser Arg Thr Pro
        290                 295                 300 gag gtc aca tgc gtg gtg gtg gac gtg agc cac gaa gac cct gag gtc        1077
Glu Val Thr Cys Val Val Val Asp Val Ser His Glu Asp Pro Glu Val
305                 310                 315                 320 aag ttc aac tgg tac gtg gac ggc gtg gag gtg cat aat gcc aag aca        1125
Lys Phe Asn Trp Tyr Val Asp Gly Val Glu Val His Asn Ala Lys Thr
                325                 330                 335 aag ccg cgg gag gag cag tac aac agc acg tac cgt gtg gtc agc gtc        1173
Lys Pro Arg Glu Glu Gln Tyr Asn Ser Thr Tyr Arg Val Val Ser Val
                340                 345                 350 ctc acc gtc ctg cac cag gac tgg ctg aat ggc aag gag tac aag tgc        1221
Leu Thr Val Leu His Gln Asp Trp Leu Asn Gly Lys Glu Tyr Lys Cys
            355                 360                 365 aag gtc tcc aac aaa gcc ctc cca gcc ccc atc gag aaa acc atc tcc        1269
Lys Val Ser Asn Lys Ala Leu Pro Ala Pro Ile Glu Lys Thr Ile Ser
        370                 375                 380 aaa gcc aaa ggg cag ccc cga gaa cca cag gtg tac acc ctg ccc cca        1317
Lys Ala Lys Gly Gln Pro Arg Glu Pro Gln Val Tyr Thr Leu Pro Pro
385                 390                 395                 400
```

```
tcc cgg gag gag atg acc aag aac cag gtc agc ctg acc tgc ctg gtc       1365
Ser Arg Glu Glu Met Thr Lys Asn Gln Val Ser Leu Thr Cys Leu Val
                    405                 410                 415 aaa ggc ttc tat ccc agc gac atc gcc gtg gag tgg gag agc aat ggg       1413
Lys Gly Phe Tyr Pro Ser Asp Ile Ala Val Glu Trp Glu Ser Asn Gly
                420                 425                 430 cag ccg gag aac aac tac aag acc acg cct ccc gtg ctg gac tcc gac       1461
Gln Pro Glu Asn Asn Tyr Lys Thr Thr Pro Pro Val Leu Asp Ser Asp
            435                 440                 445 ggc tcc ttc ttc ctc tat agc aag ctc acc gtg gac aag agc agg tgg       1509
Gly Ser Phe Phe Leu Tyr Ser Lys Leu Thr Val Asp Lys Ser Arg Trp
        450                 455                 460 cag cag ggg aac gtc ttc tca tgc tcc gtg atg cat gag gct ctg cac       1557
Gln Gln Gly Asn Val Phe Ser Cys Ser Val Met His Glu Ala Leu His
465                 470                 475                 480 aac cac tac acg cag aag agc ctc tcc ctg tct ccg ggt aaa tga           1602
Asn His Tyr Thr Gln Lys Ser Leu Ser Leu Ser Pro Gly Lys
                485                 490 actagagcgg ccgccaccgc ggtggagctc cagcttttgt tccctttagt gagggttaat    1662
ttcgagcttg gcgtaatcat ggtcatagct gtttcctg                            1700

<210> SEQ ID NO 2
<211> LENGTH: 494
<212> TYPE: PRT
<213> ORGANISM: Artificial Sequence
<220> FEATURE:
<223> OTHER INFORMATION: Fusion Construct

<400> SEQUENCE: 2

Met Glu Thr Asp Thr Leu Leu Leu Trp Val Leu Leu Leu Trp Val Pro
1               5                   10                  15

Gly Ser Thr Gly Thr Ser Cys Gly Asn Leu Phe Val Glu Arg Gly Glu
            20                  25                  30

Gln Cys Asp Cys Gly Pro Pro Glu Asp Cys Arg Asn Arg Cys Cys Asn
        35                  40                  45

Ser Thr Thr Cys Gln Leu Ala Glu Gly Ala Gln Cys Ala His Gly Thr
    50                  55                  60

Cys Cys Gln Glu Cys Lys Val Lys Pro Ala Gly Glu Leu Cys Arg Pro
65                  70                  75                  80

Lys Lys Asp Met Cys Asp Leu Glu Glu Phe Cys Asp Gly Arg His Pro
                85                  90                  95

Glu Cys Pro Glu Asp Ala Phe Gln Glu Asn Gly Thr Pro Cys Ser Gly
            100                 105                 110

Gly Tyr Cys Tyr Asn Gly Ala Cys Pro Thr Leu Ala Gln Gln Cys Gln
        115                 120                 125

Ala Phe Trp Gly Pro Gly Gly Gln Ala Ala Glu Ser Cys Phe Ser
    130                 135                 140

Tyr Asp Ile Leu Pro Gly Cys Lys Ala Ser Arg Tyr Arg Ala Asp Met
145                 150                 155                 160

Cys Gly Val Leu Gln Cys Lys Gly Gly Gln Pro Leu Gly Arg Ala
                165                 170                 175

Ile Cys Ile Val Asp Val Cys His Ala Leu Thr Thr Glu Asp Gly Thr
            180                 185                 190

Ala Tyr Glu Pro Val Pro Glu Gly Thr Arg Cys Gly Pro Glu Lys Val
        195                 200                 205

Cys Trp Lys Gly Arg Cys Gln Asp Leu His Val Tyr Arg Ser Ser Asn
    210                 215                 220
```

```
Cys Ser Ala Gln Cys His Asn His Gly Val Cys Asn His Lys Gln Glu
225                 230                 235                 240

Cys His Cys His Ala Gly Trp Ala Pro Pro His Cys Ala Lys Leu Leu
            245                 250                 255

Thr Glu Val His Ala Ala Ser Gly Arg Ser Cys Asp Lys Thr His Thr
        260                 265                 270

Cys Pro Pro Cys Pro Ala Pro Glu Ala Glu Gly Ala Pro Ser Val Phe
    275                 280                 285

Leu Phe Pro Pro Lys Pro Lys Asp Thr Leu Met Ile Ser Arg Thr Pro
290                 295                 300

Glu Val Thr Cys Val Val Val Asp Val Ser His Glu Asp Pro Glu Val
305                 310                 315                 320

Lys Phe Asn Trp Tyr Val Asp Gly Val Glu Val His Asn Ala Lys Thr
                325                 330                 335

Lys Pro Arg Glu Glu Gln Tyr Asn Ser Thr Tyr Arg Val Val Ser Val
            340                 345                 350

Leu Thr Val Leu His Gln Asp Trp Leu Asn Gly Lys Glu Tyr Lys Cys
        355                 360                 365

Lys Val Ser Asn Lys Ala Leu Pro Ala Pro Ile Glu Lys Thr Ile Ser
    370                 375                 380

Lys Ala Lys Gly Gln Pro Arg Glu Pro Gln Val Tyr Thr Leu Pro Pro
385                 390                 395                 400

Ser Arg Glu Glu Met Thr Lys Asn Gln Val Ser Leu Thr Cys Leu Val
                405                 410                 415

Lys Gly Phe Tyr Pro Ser Asp Ile Ala Val Glu Trp Glu Ser Asn Gly
            420                 425                 430

Gln Pro Glu Asn Asn Tyr Lys Thr Thr Pro Pro Val Leu Asp Ser Asp
        435                 440                 445

Gly Ser Phe Phe Leu Tyr Ser Lys Leu Thr Val Asp Lys Ser Arg Trp
    450                 455                 460

Gln Gln Gly Asn Val Phe Ser Cys Ser Val Met His Glu Ala Leu His
465                 470                 475                 480

Asn His Tyr Thr Gln Lys Ser Leu Ser Leu Ser Pro Gly Lys
                485                 490

<210> SEQ ID NO 3
<211> LENGTH: 1668
<212> TYPE: DNA
<213> ORGANISM: Artificial Sequence
<220> FEATURE:
<223> OTHER INFORMATION: Fusion Construct
<221> NAME/KEY: CDS
<222> LOCATION: (46)..(1647)
<223> OTHER INFORMATION:

<400> SEQUENCE: 3
ggtaccgggc cccccctcga ggtcgaccca agctggctag ccacc atg gag aca gac          57
                                                Met Glu Thr Asp
                                                1 aca ctc ctg cta tgg gta ctg ctg ctc tgg gtt cca ggt tcc act ggt          105
Thr Leu Leu Leu Trp Val Leu Leu Leu Trp Val Pro Gly Ser Thr Gly
5                   10                  15                  20 act agt tgt ggt aat aag ttg gtg gac gct ggg gaa gag tgt gac tgt          153
Thr Ser Cys Gly Asn Lys Leu Val Asp Ala Gly Glu Glu Cys Asp Cys
                25                  30                  35 ggt act cca aag gaa tgt gaa ttg gac cct tgc tgc gaa gga agt acc          201
Gly Thr Pro Lys Glu Cys Glu Leu Asp Pro Cys Cys Glu Gly Ser Thr
```

-continued

```
                40                      45                      50
tgt aag ctt aaa tca ttt gct gag tgt gca tat ggt gac tgt tgt aaa    249
Cys Lys Leu Lys Ser Phe Ala Glu Cys Ala Tyr Gly Asp Cys Cys Lys
         55                      60                      65 gac tgt cgg ttc ctt cca gga ggt act tta tgc cga gga aaa acc agt    297
Asp Cys Arg Phe Leu Pro Gly Gly Thr Leu Cys Arg Gly Lys Thr Ser
 70                      75                      80 gag tgt gat gtt cca gag tac tgc aat ggt tct tct cag ttc tgt cag    345
Glu Cys Asp Val Pro Glu Tyr Cys Asn Gly Ser Ser Gln Phe Cys Gln
 85                      90                      95                     100 cca gat gtt ttt att cag aat gga tat cct tgc cag aat aac aaa gcc    393
Pro Asp Val Phe Ile Gln Asn Gly Tyr Pro Cys Gln Asn Asn Lys Ala
                     105                     110                     115 tat tgc tac aac ggc atg tgc cag tat tat gat gct caa tgt caa gtc    441
Tyr Cys Tyr Asn Gly Met Cys Gln Tyr Tyr Asp Ala Gln Cys Gln Val
                 120                     125                     130 atc ttt ggc tca aaa gcc aag gct gcc ccc aaa gat tgt ttc att gaa    489
Ile Phe Gly Ser Lys Ala Lys Ala Ala Pro Lys Asp Cys Phe Ile Glu
             135                     140                     145 gtg aat tct aaa ggt gac aga ttt ggc aat tgt ggt ttc tct ggc aat    537
Val Asn Ser Lys Gly Asp Arg Phe Gly Asn Cys Gly Phe Ser Gly Asn
         150                     155                     160 gaa tac aag aag tgt gcc act ggg aat gct ttg tgt gga aag ctt cag    585
Glu Tyr Lys Lys Cys Ala Thr Gly Asn Ala Leu Cys Gly Lys Leu Gln
165                     170                     175                     180 tgt gag aat gta caa gag ata cct gta ttt gga att gtg cct gct att    633
Cys Glu Asn Val Gln Glu Ile Pro Val Phe Gly Ile Val Pro Ala Ile
                     185                     190                     195 att caa acg cct agt cga ggc acc aaa tgt tgg ggt gtg gat ttc cag    681
Ile Gln Thr Pro Ser Arg Gly Thr Lys Cys Trp Gly Val Asp Phe Gln
                 200                     205                     210 cta gga tca gat gtt cca gat cct ggg atg gtt aac gaa ggc aca aaa    729
Leu Gly Ser Asp Val Pro Asp Pro Gly Met Val Asn Glu Gly Thr Lys
             215                     220                     225 tgt ggt gct gga aag atc tgt aga aac ttc cag tgt gta gat gct tct    777
Cys Gly Ala Gly Lys Ile Cys Arg Asn Phe Gln Cys Val Asp Ala Ser
         230                     235                     240 gtt ctg aat tat gac tgt gat gtt cag aaa aag tgt cat gga cat ggg    825
Val Leu Asn Tyr Asp Cys Asp Val Gln Lys Lys Cys His Gly His Gly
245                     250                     255                     260 gta tgt aat agc aat aag aat tgt cac tgt gaa aat ggc tgg gct ccc    873
Val Cys Asn Ser Asn Lys Asn Cys His Cys Glu Asn Gly Trp Ala Pro
                     265                     270                     275 cca aat tgt gag act aaa gga tac gga gga agt gtg gac agt gga cct    921
Pro Asn Cys Glu Thr Lys Gly Tyr Gly Gly Ser Val Asp Ser Gly Pro
                 280                     285                     290 aca tac aat gaa atg aat act gca ttg agg gac gga tct tgt gac aaa    969
Thr Tyr Asn Glu Met Asn Thr Ala Leu Arg Asp Gly Ser Cys Asp Lys
             295                     300                     305 act cac aca tgc cca ccg tgc cca gca cct gaa gcc gag ggc gcg ccg   1017
Thr His Thr Cys Pro Pro Cys Pro Ala Pro Glu Ala Glu Gly Ala Pro
         310                     315                     320 tca gtc ttc ctc ttc ccc cca aaa ccc aag gac acc ctc atg atc tcc   1065
Ser Val Phe Leu Phe Pro Pro Lys Pro Lys Asp Thr Leu Met Ile Ser
325                     330                     335                     340 cgg acc cct gag gtc aca tgc gtg gtg gtg gac gtg agc cac gaa gac   1113
Arg Thr Pro Glu Val Thr Cys Val Val Val Asp Val Ser His Glu Asp
                     345                     350                     355 cct gag gtc aag ttc aac tgg tac gtg gac ggc gtg gag gtg cat aat   1161
```

| | | |
|---|---|---|
| gcc aag aca aag ccg cgg gag gag cag tac aac agc acg tac cgg gtg<br>Ala Lys Thr Lys Pro Arg Glu Glu Gln Tyr Asn Ser Thr Tyr Arg Val<br>375 380 385 | | 1209 |
| gtc agc gtc ctc acc gtc ctg cac cag gac tgg ctg aat ggc aag gag<br>Val Ser Val Leu Thr Val Leu His Gln Asp Trp Leu Asn Gly Lys Glu<br>390 395 400 | | 1257 |
| tac aag tgc aag gtc tcc aac aaa gcc ctc cca gcc ccc atc gag aaa<br>Tyr Lys Cys Lys Val Ser Asn Lys Ala Leu Pro Ala Pro Ile Glu Lys<br>405 410 415 420 | | 1305 |
| acc atc tcc aaa gcc aaa ggg cag ccc cga gaa cca cag gtg tac acc<br>Thr Ile Ser Lys Ala Lys Gly Gln Pro Arg Glu Pro Gln Val Tyr Thr<br>425 430 435 | | 1353 |
| ctg ccc cca tcc cgg gat gag ctg acc aag aac cag gtc agc ctg acc<br>Leu Pro Pro Ser Arg Asp Glu Leu Thr Lys Asn Gln Val Ser Leu Thr<br>440 445 450 | | 1401 |
| tgc ctg gtc aaa ggc ttc tat ccc agc gac atc gcc gtg gag tgg gag<br>Cys Leu Val Lys Gly Phe Tyr Pro Ser Asp Ile Ala Val Glu Trp Glu<br>455 460 465 | | 1449 |
| agc aat ggg cag ccg gag aac aac tac aag acc acg cct ccc gtg ctg<br>Ser Asn Gly Gln Pro Glu Asn Asn Tyr Lys Thr Thr Pro Pro Val Leu<br>470 475 480 | | 1497 |
| gac tcc gac ggc tcc ttc ttc ctc tac agc aag ctc acc gtg gac aag<br>Asp Ser Asp Gly Ser Phe Phe Leu Tyr Ser Lys Leu Thr Val Asp Lys<br>485 490 495 500 | | 1545 |
| agc agg tgg cag cag ggg aac gtc ttc tca tgc tcc gtg atg cat gag<br>Ser Arg Trp Gln Gln Gly Asn Val Phe Ser Cys Ser Val Met His Glu<br>505 510 515 | | 1593 |
| gct ctg cac aac cac tac acg cag aag agc ctc tcc ctg tct ccg ggt<br>Ala Leu His Asn His Tyr Thr Gln Lys Ser Leu Ser Leu Ser Pro Gly<br>520 525 530 | | 1641 |
| aaa tga actagagcgg ccgctacaga t<br>Lys | | 1668 |

<210> SEQ ID NO 4
<211> LENGTH: 533
<212> TYPE: PRT
<213> ORGANISM: Artificial Sequence
<220> FEATURE:
<223> OTHER INFORMATION: Fusion Construct

<400> SEQUENCE: 4

Met Glu Thr Asp Thr Leu Leu Leu Trp Val Leu Leu Leu Trp Val Pro
1               5                   10                  15

Gly Ser Thr Gly Thr Ser Cys Gly Asn Lys Leu Val Asp Ala Gly Glu
            20                  25                  30

Glu Cys Asp Cys Gly Thr Pro Lys Glu Cys Glu Leu Asp Pro Cys Cys
        35                  40                  45

Glu Gly Ser Thr Cys Lys Leu Lys Ser Phe Ala Glu Cys Ala Tyr Gly
    50                  55                  60

Asp Cys Cys Lys Asp Cys Arg Phe Leu Pro Gly Gly Thr Leu Cys Arg
65                  70                  75                  80

Gly Lys Thr Ser Glu Cys Asp Val Pro Glu Tyr Cys Asn Gly Ser Ser
                85                  90                  95

Gln Phe Cys Gln Pro Asp Val Phe Ile Gln Asn Gly Tyr Pro Cys Gln
            100                 105                 110

Asn Asn Lys Ala Tyr Cys Tyr Asn Gly Met Cys Gln Tyr Tyr Asp Ala
        115                 120                 125

```
Gln Cys Gln Val Ile Phe Gly Ser Lys Ala Lys Ala Pro Lys Asp
    130                 135                 140
Cys Phe Ile Glu Val Asn Ser Lys Gly Asp Arg Phe Gly Asn Cys Gly
145                 150                 155                 160
Phe Ser Gly Asn Glu Tyr Lys Lys Cys Ala Thr Gly Asn Ala Leu Cys
                165                 170                 175
Gly Lys Leu Gln Cys Glu Asn Val Gln Glu Ile Pro Val Phe Gly Ile
            180                 185                 190
Val Pro Ala Ile Ile Gln Thr Pro Ser Arg Gly Thr Lys Cys Trp Gly
        195                 200                 205
Val Asp Phe Gln Leu Gly Ser Asp Val Pro Asp Pro Gly Met Val Asn
    210                 215                 220
Glu Gly Thr Lys Cys Gly Ala Gly Lys Ile Cys Arg Asn Phe Gln Cys
225                 230                 235                 240
Val Asp Ala Ser Val Leu Asn Tyr Asp Cys Asp Val Gln Lys Lys Cys
                245                 250                 255
His Gly His Gly Val Cys Asn Ser Asn Lys Asn Cys His Cys Glu Asn
            260                 265                 270
Gly Trp Ala Pro Pro Asn Cys Glu Thr Lys Gly Tyr Gly Gly Ser Val
        275                 280                 285
Asp Ser Gly Pro Thr Tyr Asn Glu Met Asn Thr Ala Leu Arg Asp Gly
    290                 295                 300
Ser Cys Asp Lys Thr His Thr Cys Pro Pro Cys Pro Ala Pro Glu Ala
305                 310                 315                 320
Glu Gly Ala Pro Ser Val Phe Leu Phe Pro Pro Lys Pro Lys Asp Thr
                325                 330                 335
Leu Met Ile Ser Arg Thr Pro Glu Val Thr Cys Val Val Val Asp Val
            340                 345                 350
Ser His Glu Asp Pro Glu Val Lys Phe Asn Trp Tyr Val Asp Gly Val
        355                 360                 365
Glu Val His Asn Ala Lys Thr Lys Pro Arg Glu Glu Gln Tyr Asn Ser
    370                 375                 380
Thr Tyr Arg Val Val Ser Val Leu Thr Val Leu His Gln Asp Trp Leu
385                 390                 395                 400
Asn Gly Lys Glu Tyr Lys Cys Lys Val Ser Asn Lys Ala Leu Pro Ala
                405                 410                 415
Pro Ile Glu Lys Thr Ile Ser Lys Ala Lys Gly Gln Pro Arg Glu Pro
            420                 425                 430
Gln Val Tyr Thr Leu Pro Pro Ser Arg Asp Glu Leu Thr Lys Asn Gln
        435                 440                 445
Val Ser Leu Thr Cys Leu Val Lys Gly Phe Tyr Pro Ser Asp Ile Ala
    450                 455                 460
Val Glu Trp Glu Ser Asn Gly Gln Pro Glu Asn Asn Tyr Lys Thr Thr
465                 470                 475                 480
Pro Pro Val Leu Asp Ser Asp Gly Ser Phe Phe Leu Tyr Ser Lys Leu
                485                 490                 495
Thr Val Asp Lys Ser Arg Trp Gln Gln Gly Asn Val Phe Ser Cys Ser
            500                 505                 510
Val Met His Glu Ala Leu His Asn His Tyr Thr Gln Lys Ser Leu Ser
        515                 520                 525
Leu Ser Pro Gly Lys
    530
```

-continued

```
<210> SEQ ID NO 5
<211> LENGTH: 1443
<212> TYPE: DNA
<213> ORGANISM: Artificial Sequence
<220> FEATURE:
<223> OTHER INFORMATION: Fusion Construct
<221> NAME/KEY: CDS
<222> LOCATION: (25)..(1422)
<223> OTHER INFORMATION:

<400> SEQUENCE: 5
gtcgacccaa gctggctagc cacc atg gag aca gac aca ctc ctg cta tgg          51
                           Met Glu Thr Asp Thr Leu Leu Leu Trp
                            1               5 gta ctg ctg ctc tgg gtt cca ggt tcc act ggt act agt tgt gga aat         99
Val Leu Leu Leu Trp Val Pro Gly Ser Thr Gly Thr Ser Cys Gly Asn
 10              15                  20                  25 gga atg gta gaa caa ggt gaa gaa tgt gat tgt ggc tat agt gac cag        147
Gly Met Val Glu Gln Gly Glu Glu Cys Asp Cys Gly Tyr Ser Asp Gln
                 30                  35                  40 tgt aaa gat gaa tgc tgc ttc gat gca aat caa cca gag gga aga aaa        195
Cys Lys Asp Glu Cys Cys Phe Asp Ala Asn Gln Pro Glu Gly Arg Lys
             45                  50                  55 tgc aaa ctg aaa cct ggg aaa cag tgc agt cca agt caa ggt cct tgt        243
Cys Lys Leu Lys Pro Gly Lys Gln Cys Ser Pro Ser Gln Gly Pro Cys
         60                  65                  70 tgt aca gca cag tgt gca ttc aag tca aag tct gag aag tgt cgg gat        291
Cys Thr Ala Gln Cys Ala Phe Lys Ser Lys Ser Glu Lys Cys Arg Asp
     75                  80                  85 gat tca gac tgt gca agg gaa gga ata tgt aat ggc ttc aca gct ctc        339
Asp Ser Asp Cys Ala Arg Glu Gly Ile Cys Asn Gly Phe Thr Ala Leu
 90                  95                 100                 105 tgc cca gca tct gac cct aaa cca aac ttc aca gac tgt aat agg cat        387
Cys Pro Ala Ser Asp Pro Lys Pro Asn Phe Thr Asp Cys Asn Arg His
                110                 115                 120 aca caa gtg tgc att aat ggg caa tgt gca ggt tct atc tgt gag aaa        435
Thr Gln Val Cys Ile Asn Gly Gln Cys Ala Gly Ser Ile Cys Glu Lys
            125                 130                 135 tat ggc tta gag gag tgt acg tgt gcc agt tct gat ggc aaa gat gat        483
Tyr Gly Leu Glu Glu Cys Thr Cys Ala Ser Ser Asp Gly Lys Asp Asp
        140                 145                 150 aaa gaa tta tgc cat gta tgc tgt atg aag aaa atg gac cca tca act        531
Lys Glu Leu Cys His Val Cys Cys Met Lys Lys Met Asp Pro Ser Thr
    155                 160                 165 tgt gcc agt aca ggg tct gtg cag tgg agt agg cac ttc agt ggt cga        579
Cys Ala Ser Thr Gly Ser Val Gln Trp Ser Arg His Phe Ser Gly Arg
170                 175                 180                 185 acc atc acc ctg caa cct gga tcc cct tgc aac gat ttt aga ggt tac        627
Thr Ile Thr Leu Gln Pro Gly Ser Pro Cys Asn Asp Phe Arg Gly Tyr
                190                 195                 200 tgt gat gtt ttc atg cgg tgc aga tta gta gat gct gat ggt cct cta        675
Cys Asp Val Phe Met Arg Cys Arg Leu Val Asp Ala Asp Gly Pro Leu
            205                 210                 215 gct agg ctt aaa aaa gca att ttt agt cca gag ctc tat gaa aac att        723
Ala Arg Leu Lys Lys Ala Ile Phe Ser Pro Glu Leu Tyr Glu Asn Ile
        220                 225                 230 gct gaa aga tct tgt gac aaa act cac aca tgc cca ccg tgc cca gca        771
Ala Glu Arg Ser Cys Asp Lys Thr His Thr Cys Pro Pro Cys Pro Ala
    235                 240                 245 cct gaa gcc gag ggc gcg ccg tca gtc ttc ctc ttc ccc cca aaa ccc        819
Pro Glu Ala Glu Gly Ala Pro Ser Val Phe Leu Phe Pro Pro Lys Pro
```

-continued

| | | | |
|---|---|---|---|
| aag gac acc ctc atg atc tcc cgg acc cct gag gtc aca tgc gtg gtg<br>Lys Asp Thr Leu Met Ile Ser Arg Thr Pro Glu Val Thr Cys Val Val<br>250　　　　　　255　　　　　　260　　　　　　265<br>　　　　　　　　　　　　　　　　270　　　　　　　　　275　　　　　　　　280 | 867 |
| gtg gac gtg agc cac gaa gac cct gag gtc aag ttc aac tgg tac gtg<br>Val Asp Val Ser His Glu Asp Pro Glu Val Lys Phe Asn Trp Tyr Val<br>　　　　　　　　285　　　　　　　　　290　　　　　　　　　295 | 915 |
| gac ggc gtg gag gtg cat aat gcc aag aca aag ccg cgg gag gag cag<br>Asp Gly Val Glu Val His Asn Ala Lys Thr Lys Pro Arg Glu Glu Gln<br>300　　　　　　　　　305　　　　　　　　　310 | 963 |
| tac aac agc acg tac cgg gtg gtc agc gtc ctc acc gtc ctg cac cag<br>Tyr Asn Ser Thr Tyr Arg Val Val Ser Val Leu Thr Val Leu His Gln<br>　　　315　　　　　　　　　320　　　　　　　　　325 | 1011 |
| gac tgg ctg aat ggc aag gag tac aag tgc aag gtc tcc aac aaa gcc<br>Asp Trp Leu Asn Gly Lys Glu Tyr Lys Cys Lys Val Ser Asn Lys Ala<br>330　　　　　　　　　335　　　　　　　　　340　　　　　　　　　345 | 1059 |
| ctc cca gcc ccc atc gag aaa acc atc tcc aaa gcc aaa ggg cag ccc<br>Leu Pro Ala Pro Ile Glu Lys Thr Ile Ser Lys Ala Lys Gly Gln Pro<br>　　　　　　　　　350　　　　　　　　　355　　　　　　　　　360 | 1107 |
| cga gaa cca cag gtg tac acc ctg ccc cca tcc cgg gat gag ctg acc<br>Arg Glu Pro Gln Val Tyr Thr Leu Pro Pro Ser Arg Asp Glu Leu Thr<br>　　　365　　　　　　　　　370　　　　　　　　　375 | 1155 |
| aag aac cag gtc agc ctg acc tgc ctg gtc aaa ggc ttc tat ccc agc<br>Lys Asn Gln Val Ser Leu Thr Cys Leu Val Lys Gly Phe Tyr Pro Ser<br>380　　　　　　　　　385　　　　　　　　　390 | 1203 |
| gac atc gcc gtg gag tgg gag agc aat ggg cag ccg gag aac aac tac<br>Asp Ile Ala Val Glu Trp Glu Ser Asn Gly Gln Pro Glu Asn Asn Tyr<br>395　　　　　　　　　400　　　　　　　　　405 | 1251 |
| aag acc acg cct ccc gtg ctg gac tcc gac ggc tcc ttc ttc ctc tac<br>Lys Thr Thr Pro Pro Val Leu Asp Ser Asp Gly Ser Phe Phe Leu Tyr<br>410　　　　　　　　　415　　　　　　　　　420　　　　　　　　　425 | 1299 |
| agc aag ctc acc gtg gac aag agc agg tgg cag cag ggg aac gtc ttc<br>Ser Lys Leu Thr Val Asp Lys Ser Arg Trp Gln Gln Gly Asn Val Phe<br>　　　　　　　　　430　　　　　　　　　435　　　　　　　　　440 | 1347 |
| tca tgc tcc gtg atg cat gag gct ctg cac aac cac tac acg cag aag<br>Ser Cys Ser Val Met His Glu Ala Leu His Asn His Tyr Thr Gln Lys<br>　　　　　　　　　445　　　　　　　　　450　　　　　　　　　455 | 1395 |
| agc ctc tcc ctg tct ccg ggt aaa tga actagagcgg ccgctacaga t<br>Ser Leu Ser Leu Ser Pro Gly Lys<br>　　　460　　　　　　　　　465 | 1443 |

<210> SEQ ID NO 6
<211> LENGTH: 465
<212> TYPE: PRT
<213> ORGANISM: Artificial Sequence
<220> FEATURE:
<223> OTHER INFORMATION: Fusion Construct

<400> SEQUENCE: 6

Met Glu Thr Asp Thr Leu Leu Leu Trp Val Leu Leu Leu Trp Val Pro
1               5                   10                  15

Gly Ser Thr Gly Thr Ser Cys Gly Asn Gly Met Val Glu Gln Gly Glu
            20                  25                  30

Glu Cys Asp Cys Gly Tyr Ser Asp Gln Cys Lys Asp Glu Cys Cys Phe
        35                  40                  45

Asp Ala Asn Gln Pro Glu Gly Arg Lys Cys Lys Leu Lys Pro Gly Lys
    50                  55                  60

Gln Cys Ser Pro Ser Gln Gly Pro Cys Cys Thr Ala Gln Cys Ala Phe
65                  70                  75                  80

-continued

```
Lys Ser Lys Ser Glu Lys Cys Arg Asp Asp Ser Asp Cys Ala Arg Glu
                85                  90                  95
Gly Ile Cys Asn Gly Phe Thr Ala Leu Cys Pro Ala Ser Asp Pro Lys
            100                 105                 110
Pro Asn Phe Thr Asp Cys Asn Arg His Thr Gln Val Cys Ile Asn Gly
        115                 120                 125
Gln Cys Ala Gly Ser Ile Cys Glu Lys Tyr Gly Leu Glu Glu Cys Thr
    130                 135                 140
Cys Ala Ser Ser Asp Gly Lys Asp Lys Glu Leu Cys His Val Cys
145                 150                 155                 160
Cys Met Lys Lys Met Asp Pro Ser Thr Cys Ala Ser Thr Gly Ser Val
                165                 170                 175
Gln Trp Ser Arg His Phe Ser Gly Arg Thr Ile Thr Leu Gln Pro Gly
            180                 185                 190
Ser Pro Cys Asn Asp Phe Arg Gly Tyr Cys Asp Val Phe Met Arg Cys
        195                 200                 205
Arg Leu Val Asp Ala Asp Gly Pro Leu Ala Arg Leu Lys Lys Ala Ile
    210                 215                 220
Phe Ser Pro Glu Leu Tyr Glu Asn Ile Ala Glu Arg Ser Cys Asp Lys
225                 230                 235                 240
Thr His Thr Cys Pro Pro Cys Pro Ala Pro Glu Ala Glu Gly Ala Pro
                245                 250                 255
Ser Val Phe Leu Phe Pro Pro Lys Pro Lys Asp Thr Leu Met Ile Ser
            260                 265                 270
Arg Thr Pro Glu Val Thr Cys Val Val Val Asp Val Ser His Glu Asp
        275                 280                 285
Pro Glu Val Lys Phe Asn Trp Tyr Val Asp Gly Val Glu Val His Asn
    290                 295                 300
Ala Lys Thr Lys Pro Arg Glu Glu Gln Tyr Asn Ser Thr Tyr Arg Val
305                 310                 315                 320
Val Ser Val Leu Thr Val Leu His Gln Asp Trp Leu Asn Gly Lys Glu
                325                 330                 335
Tyr Lys Cys Lys Val Ser Asn Lys Ala Leu Pro Ala Pro Ile Glu Lys
            340                 345                 350
Thr Ile Ser Lys Ala Lys Gly Gln Pro Arg Glu Pro Gln Val Tyr Thr
        355                 360                 365
Leu Pro Pro Ser Arg Asp Glu Leu Thr Lys Asn Gln Val Ser Leu Thr
    370                 375                 380
Cys Leu Val Lys Gly Phe Tyr Pro Ser Asp Ile Ala Val Glu Trp Glu
385                 390                 395                 400
Ser Asn Gly Gln Pro Glu Asn Asn Tyr Lys Thr Thr Pro Pro Val Leu
                405                 410                 415
Asp Ser Asp Gly Ser Phe Phe Leu Tyr Ser Lys Leu Thr Val Asp Lys
            420                 425                 430
Ser Arg Trp Gln Gln Gly Asn Val Phe Ser Cys Ser Val Met His Glu
        435                 440                 445
Ala Leu His Asn His Tyr Thr Gln Lys Ser Leu Ser Leu Ser Pro Gly
    450                 455                 460
Lys
465

<210> SEQ ID NO 7
<211> LENGTH: 1638
<212> TYPE: DNA
```

<213> ORGANISM: Artificial Sequence
<220> FEATURE:
<223> OTHER INFORMATION: Fusion Construct
<221> NAME/KEY: CDS
<222> LOCATION: (41)..(1609)
<223> OTHER INFORMATION:

<400> SEQUENCE: 7

| | | | | | | | | | | | |
|---|---|---|---|---|---|---|---|---|---|---|---|
| cgggccccc ctcgaggtcg acccaagctg gctagccacc | atg<br>Met<br>1 | gag<br>Glu | aca<br>Thr | gac<br>Asp | aca<br>Thr<br>5 | | | | | | 55 |
| ctc<br>Leu | ctg<br>Leu | cta<br>Leu | tgg<br>Trp | gta<br>Val<br>10 | ctg<br>Leu | ctc<br>Leu | tgg<br>Trp | gtt<br>Val<br>15 | cca<br>Pro | ggt<br>Gly | tcc<br>Ser | act<br>Thr | ggt<br>Gly<br>20 | act<br>Thr | 103 |
| agt<br>Ser | tgc<br>Cys | gga<br>Gly | aat<br>Asn<br>25 | atg<br>Met | ttt<br>Phe | gtg<br>Val | gag<br>Glu | ccg<br>Pro<br>30 | ggc<br>Gly | gag<br>Glu | cag<br>Gln | tgt<br>Cys | gac<br>Asp<br>35 | tgt<br>Cys | ggc<br>Gly | 151 |
| ttc<br>Phe | ctg<br>Leu | gat<br>Asp<br>40 | gac<br>Asp | tgc<br>Cys | gtc<br>Val | gat<br>Asp | ccc<br>Pro<br>45 | tgc<br>Cys | tgt<br>Cys | gat<br>Asp | tct<br>Ser | ttg<br>Leu<br>50 | acc<br>Thr | tgc<br>Cys | cag<br>Gln | 199 |
| ctg<br>Leu | agg<br>Arg<br>55 | cca<br>Pro | ggt<br>Gly | gca<br>Ala | cag<br>Gln | tgt<br>Cys<br>60 | gca<br>Ala | tct<br>Ser | gac<br>Asp | gga<br>Gly | ccc<br>Pro<br>65 | tgt<br>Cys | tgt<br>Cys | caa<br>Gln | aat<br>Asn | 247 |
| tgc<br>Cys<br>70 | cag<br>Gln | ctg<br>Leu | cgc<br>Arg | ccg<br>Pro<br>75 | tct<br>Ser | ggc<br>Gly | tgg<br>Trp | cag<br>Gln | tgt<br>Cys<br>80 | cgt<br>Arg | cct<br>Pro | acc<br>Thr | aga<br>Arg | ggg<br>Gly<br>85 | gat<br>Asp | 295 |
| tgt<br>Cys | gac<br>Asp | ttg<br>Leu | cct<br>Pro | gaa<br>Glu<br>90 | ttc<br>Phe | tgc<br>Cys | cca<br>Pro | gga<br>Gly | gac<br>Asp<br>95 | agc<br>Ser | tcc<br>Ser | cag<br>Gln | tgt<br>Cys | ccc<br>Pro<br>100 | cct<br>Pro | 343 |
| gat<br>Asp | gtc<br>Val | agc<br>Ser | cta<br>Leu<br>105 | ggg<br>Gly | gat<br>Asp | ggc<br>Gly | gag<br>Glu | ccc<br>Pro<br>110 | tgc<br>Cys | gct<br>Ala | ggc<br>Gly | ggg<br>Gly | caa<br>Gln<br>115 | gct<br>Ala | gtg<br>Val | 391 |
| tgc<br>Cys | atg<br>Met | cac<br>His<br>120 | ggg<br>Gly | cgt<br>Arg | tgt<br>Cys | gcc<br>Ala | tcc<br>Ser<br>125 | tat<br>Tyr | gcc<br>Ala | cag<br>Gln | cag<br>Gln | tgc<br>Cys<br>130 | cag<br>Gln | tca<br>Ser | ctt<br>Leu | 439 |
| tgg<br>Trp | gga<br>Gly<br>135 | cct<br>Pro | gga<br>Gly | gcc<br>Ala | cag<br>Gln | ccc<br>Pro<br>140 | gct<br>Ala | gcg<br>Ala | cca<br>Pro | ctt<br>Leu | tgc<br>Cys<br>145 | ctc<br>Leu | cag<br>Gln | aca<br>Thr | gct<br>Ala | 487 |
| aat<br>Asn<br>150 | act<br>Thr | cgg<br>Arg | gga<br>Gly | aat<br>Asn | gct<br>Ala<br>155 | ttt<br>Phe | ggg<br>Gly | agc<br>Ser | tgt<br>Cys | ggg<br>Gly<br>160 | cgc<br>Arg | aac<br>Asn | ccc<br>Pro | agt<br>Ser | ggc<br>Gly<br>165 | 535 |
| agt<br>Ser | tat<br>Tyr | gtg<br>Val | tcc<br>Ser | tgc<br>Cys<br>170 | acc<br>Thr | cct<br>Pro | aga<br>Arg | gat<br>Asp | gcc<br>Ala<br>175 | att<br>Ile | tgt<br>Cys | ggg<br>Gly | cag<br>Gln | ctc<br>Leu<br>180 | cag<br>Gln | 583 |
| tgc<br>Cys | cag<br>Gln | aca<br>Thr | ggt<br>Gly<br>185 | agg<br>Arg | acc<br>Thr | cag<br>Gln | cct<br>Pro | ctg<br>Leu<br>190 | ctg<br>Leu | ggc<br>Gly | tcc<br>Ser | atc<br>Ile | cgg<br>Arg<br>195 | gat<br>Asp | cta<br>Leu | 631 |
| ctc<br>Leu | tgg<br>Trp | gag<br>Glu<br>200 | aca<br>Thr | ata<br>Ile | gat<br>Asp | gtg<br>Val | aat<br>Asn<br>205 | ggg<br>Gly | act<br>Thr | gag<br>Glu | ctg<br>Leu | aac<br>Asn<br>210 | tgc<br>Cys | agc<br>Ser | tgg<br>Trp | 679 |
| gtg<br>Val | cac<br>His<br>215 | ctg<br>Leu | gac<br>Asp | ctg<br>Leu | ggc<br>Gly | agt<br>Ser<br>220 | gat<br>Asp | gtg<br>Val | gcc<br>Ala | cag<br>Gln | ccc<br>Pro<br>225 | ctc<br>Leu | ctg<br>Leu | act<br>Thr | ctg<br>Leu | 727 |
| cct<br>Pro | ggc<br>Gly<br>230 | aca<br>Thr | gcc<br>Ala | tgt<br>Cys | ggc<br>Gly<br>235 | cct<br>Pro | ggc<br>Gly | ctg<br>Leu | gtg<br>Val | tgt<br>Cys<br>240 | ata<br>Ile | gac<br>Asp | cat<br>His | cga<br>Arg | tgc<br>Cys<br>245 | 775 |
| cag<br>Gln | cgt<br>Arg | gtg<br>Val | gat<br>Asp | ctc<br>Leu<br>250 | ctg<br>Leu | ggg<br>Gly | gca<br>Ala | cag<br>Gln | gaa<br>Glu<br>255 | tgt<br>Cys | cga<br>Arg | agc<br>Ser | aaa<br>Lys | tgc<br>Cys<br>260 | cat<br>His | 823 |
| gga<br>Gly | cat<br>His | ggg<br>Gly | gtc<br>Val | tgt<br>Cys | gac<br>Asp | agc<br>Ser | aac<br>Asn | agg<br>Arg | cac<br>His | tgc<br>Cys | tac<br>Tyr | tgt<br>Cys | gag<br>Glu | gag<br>Glu | ggc<br>Gly | 871 |

```
tgg gca ccc cct gac tgc acc act cag ctc aaa gca acc agc tcc aga        919
Trp Ala Pro Pro Asp Cys Thr Thr Gln Leu Lys Ala Thr Ser Ser Arg
        280             285             290 tct tgt gac aaa act cac aca tgc cca ccg tgc cca gca cct gaa gcc        967
Ser Cys Asp Lys Thr His Thr Cys Pro Pro Cys Pro Ala Pro Glu Ala
295             300             305 gag ggc gcg ccg tca gtc ttc ctc ttc ccc cca aaa ccc aag gac acc       1015
Glu Gly Ala Pro Ser Val Phe Leu Phe Pro Pro Lys Pro Lys Asp Thr
310             315             320                 325 ctc atg atc tcc cgg acc cct gag gtc aca tgc gtg gtg gtg gac gtg       1063
Leu Met Ile Ser Arg Thr Pro Glu Val Thr Cys Val Val Val Asp Val
                330             335             340 agc cac gaa gac cct gag gtc aag ttc aac tgg tac gtg gac ggc gtg       1111
Ser His Glu Asp Pro Glu Val Lys Phe Asn Trp Tyr Val Asp Gly Val
            345             350             355 gag gtg cat aat gcc aag aca aag ccg cgg gag gag cag tac aac agc       1159
Glu Val His Asn Ala Lys Thr Lys Pro Arg Glu Glu Gln Tyr Asn Ser
        360             365             370 acg tac cgt gtg gtc agc gtc ctc acc gtc ctg cac cag gac tgg ctg       1207
Thr Tyr Arg Val Val Ser Val Leu Thr Val Leu His Gln Asp Trp Leu
375             380             385 aat ggc aag gag tac aag tgc aag gtc tcc aac aaa gcc ctc cca gcc       1255
Asn Gly Lys Glu Tyr Lys Cys Lys Val Ser Asn Lys Ala Leu Pro Ala
390             395             400             405 ccc atc gag aaa acc atc tcc aaa gcc aaa ggg cag ccc cga gaa cca       1303
Pro Ile Glu Lys Thr Ile Ser Lys Ala Lys Gly Gln Pro Arg Glu Pro
                410             415             420 cag gtg tac acc ctg ccc cca tcc cgg gag gag atg acc aag aac cag       1351
Gln Val Tyr Thr Leu Pro Pro Ser Arg Glu Glu Met Thr Lys Asn Gln
            425             430             435 gtc agc ctg acc tgc ctg gtc aaa ggc ttc tat ccc agc gac atc gcc       1399
Val Ser Leu Thr Cys Leu Val Lys Gly Phe Tyr Pro Ser Asp Ile Ala
        440             445             450 gtg gag tgg gag agc aat ggg cag ccg gag aac aac tac aag acc acg       1447
Val Glu Trp Glu Ser Asn Gly Gln Pro Glu Asn Asn Tyr Lys Thr Thr
455             460             465 cct ccc gtg ctg gac tcc gac ggc tcc ttc ttc ctc tat agc aag ctc       1495
Pro Pro Val Leu Asp Ser Asp Gly Ser Phe Phe Leu Tyr Ser Lys Leu
470             475             480             485 acc gtg gac aag agc agg tgg cag cag ggg aac gtc ttc tca tgc tcc       1543
Thr Val Asp Lys Ser Arg Trp Gln Gln Gly Asn Val Phe Ser Cys Ser
                490             495             500 gtg atg cat gag gct ctg cac aac cac tac acg cag aag agc ctc tcc       1591
Val Met His Glu Ala Leu His Asn His Tyr Thr Gln Lys Ser Leu Ser
            505             510             515 ctg tct ccg ggt aaa tga actagagcgg ccgccaccgc ggtggagct               1638
Leu Ser Pro Gly Lys
        520

<210> SEQ ID NO 8
<211> LENGTH: 522
<212> TYPE: PRT
<213> ORGANISM: Artificial Sequence
<220> FEATURE:
<223> OTHER INFORMATION: Fusion Construct

<400> SEQUENCE: 8

Met Glu Thr Asp Thr Leu Leu Leu Trp Val Leu Leu Leu Trp Val Pro
1               5                   10                  15
```

-continued

```
Gly Ser Thr Gly Thr Ser Cys Gly Asn Met Phe Val Glu Pro Gly Glu
         20                  25                  30

Gln Cys Asp Cys Gly Phe Leu Asp Asp Cys Val Asp Pro Cys Cys Asp
         35                  40                  45

Ser Leu Thr Cys Gln Leu Arg Pro Gly Ala Gln Cys Ala Ser Asp Gly
50                   55                  60

Pro Cys Cys Gln Asn Cys Gln Leu Arg Pro Ser Gly Trp Gln Cys Arg
65                   70                  75                  80

Pro Thr Arg Gly Asp Cys Asp Leu Pro Glu Phe Cys Pro Gly Asp Ser
                 85                  90                  95

Ser Gln Cys Pro Pro Asp Val Ser Leu Gly Asp Gly Glu Pro Cys Ala
             100                 105                 110

Gly Gly Gln Ala Val Cys Met His Gly Arg Cys Ala Ser Tyr Ala Gln
             115                 120                 125

Gln Cys Gln Ser Leu Trp Gly Pro Gly Ala Gln Pro Ala Ala Pro Leu
130                 135                 140

Cys Leu Gln Thr Ala Asn Thr Arg Gly Asn Ala Phe Gly Ser Cys Gly
145                 150                 155                 160

Arg Asn Pro Ser Gly Ser Tyr Val Ser Cys Thr Pro Arg Asp Ala Ile
                 165                 170                 175

Cys Gly Gln Leu Gln Cys Gln Thr Gly Arg Thr Gln Pro Leu Leu Gly
             180                 185                 190

Ser Ile Arg Asp Leu Leu Trp Glu Thr Ile Asp Val Asn Gly Thr Glu
             195                 200                 205

Leu Asn Cys Ser Trp Val His Leu Asp Leu Gly Ser Asp Val Ala Gln
210                 215                 220

Pro Leu Leu Thr Leu Pro Gly Thr Ala Cys Gly Pro Gly Leu Val Cys
225                 230                 235                 240

Ile Asp His Arg Cys Gln Arg Val Asp Leu Leu Gly Ala Gln Glu Cys
                 245                 250                 255

Arg Ser Lys Cys His Gly His Gly Val Cys Asp Ser Asn Arg His Cys
             260                 265                 270

Tyr Cys Glu Glu Gly Trp Ala Pro Pro Asp Cys Thr Thr Gln Leu Lys
             275                 280                 285

Ala Thr Ser Ser Arg Ser Cys Asp Lys Thr His Thr Cys Pro Pro Cys
290                 295                 300

Pro Ala Pro Glu Ala Glu Gly Ala Pro Ser Val Phe Leu Phe Pro Pro
305                 310                 315                 320

Lys Pro Lys Asp Thr Leu Met Ile Ser Arg Thr Pro Glu Val Thr Cys
                 325                 330                 335

Val Val Val Asp Val Ser His Glu Asp Pro Glu Val Lys Phe Asn Trp
             340                 345                 350

Tyr Val Asp Gly Val Glu Val His Asn Ala Lys Thr Lys Pro Arg Glu
             355                 360                 365

Glu Gln Tyr Asn Ser Thr Tyr Arg Val Val Ser Val Leu Thr Val Leu
370                 375                 380

His Gln Asp Trp Leu Asn Gly Lys Glu Tyr Lys Cys Lys Val Ser Asn
385                 390                 395                 400

Lys Ala Leu Pro Ala Pro Ile Glu Lys Thr Ile Ser Lys Ala Lys Gly
                 405                 410                 415

Gln Pro Arg Glu Pro Gln Val Tyr Thr Leu Pro Pro Ser Arg Glu Glu
             420                 425                 430

Met Thr Lys Asn Gln Val Ser Leu Thr Cys Leu Val Lys Gly Phe Tyr
```

```
                          435              440               445
Pro Ser Asp Ile Ala Val Glu Trp Glu Ser Asn Gly Gln Pro Glu Asn
    450                 455                 460

Asn Tyr Lys Thr Thr Pro Pro Val Leu Asp Ser Asp Gly Ser Phe Phe
465                 470                 475                 480

Leu Tyr Ser Lys Leu Thr Val Asp Lys Ser Arg Trp Gln Gln Gly Asn
                485                 490                 495

Val Phe Ser Cys Ser Val Met His Glu Ala Leu His Asn His Tyr Thr
                500                 505                 510

Gln Lys Ser Leu Ser Leu Ser Pro Gly Lys
            515                 520

<210> SEQ ID NO 9
<211> LENGTH: 1386
<212> TYPE: DNA
<213> ORGANISM: Artificial Sequence
<220> FEATURE:
<223> OTHER INFORMATION: Fusion Construct
<221> NAME/KEY: CDS
<222> LOCATION: (25)..(1365)
<223> OTHER INFORMATION:

<400> SEQUENCE: 9
```

```
gtcgacccaa gctggctagc cacc atg gag aca gac aca ctc ctg cta tgg        51
                         Met Glu Thr Asp Thr Leu Leu Leu Trp
                           1               5 gta ctg ctg ctc tgg gtt cca ggt tcc act ggt act agt tgt ggg aac       99
Val Leu Leu Leu Trp Val Pro Gly Ser Thr Gly Thr Ser Cys Gly Asn
 10                  15                  20                  25 tcg agg gtg gat gaa gga gaa gag tgt gat cct ggc atc atg tat ctg      147
Ser Arg Val Asp Glu Gly Glu Glu Cys Asp Pro Gly Ile Met Tyr Leu
                 30                  35                  40 aac aac gac acc tgc tgc aac agc gac tgc acg ttg aag gaa ggt gtc      195
Asn Asn Asp Thr Cys Cys Asn Ser Asp Cys Thr Leu Lys Glu Gly Val
             45                  50                  55 cag tgc agt gac agg aac agt cct tgc tgt aaa aac tgt cag ttt gag      243
Gln Cys Ser Asp Arg Asn Ser Pro Cys Cys Lys Asn Cys Gln Phe Glu
         60                  65                  70 act gcc cag aag aag tgc cag gag gcg att aat gct act tgc aaa ggc      291
Thr Ala Gln Lys Lys Cys Gln Glu Ala Ile Asn Ala Thr Cys Lys Gly
     75                  80                  85 gtg tcc tac tgc aca ggt aat agc agt gag tgc ccg cct cca gga aat      339
Val Ser Tyr Cys Thr Gly Asn Ser Ser Glu Cys Pro Pro Pro Gly Asn
 90                  95                 100                 105 gct gaa gat gac act gtt tgc ttg gat ctt ggc aag tgt aag gat ggg      387
Ala Glu Asp Asp Thr Val Cys Leu Asp Leu Gly Lys Cys Lys Asp Gly
                110                 115                 120 aaa tgc atc cct ttc tgc gag agg gaa cag cag ctg gag tcc tgt gca      435
Lys Cys Ile Pro Phe Cys Glu Arg Glu Gln Gln Leu Glu Ser Cys Ala
            125                 130                 135 tgt aat gaa act gac aac tcc tgc aag gtg tgc tgc agg gac ctt tcc      483
Cys Asn Glu Thr Asp Asn Ser Cys Lys Val Cys Cys Arg Asp Leu Ser
        140                 145                 150 ggc cgc tgt gtg ccc tat gtc gat gct gaa caa aag aac tta ttt ttg      531
Gly Arg Cys Val Pro Tyr Val Asp Ala Glu Gln Lys Asn Leu Phe Leu
    155                 160                 165 agg aaa gga aag ccc tgt aca gta gga ttt tgt gac atg aat ggc aaa      579
Arg Lys Gly Lys Pro Cys Thr Val Gly Phe Cys Asp Met Asn Gly Lys
170                 175                 180                 185 tgt gag aaa cga gta cag gat gta att gaa cga ttt tgg gat ttc att      627
```

|  |  |  |  |  |  |  |  |  |  |  |  |  |  |  |
|---|---|---|---|---|---|---|---|---|---|---|---|---|---|---|
| Cys | Glu | Lys | Arg | Val | Gln | Asp | Val | Ile | Glu | Arg | Phe | Trp | Asp | Phe | Ile |
|  |  |  | 190 |  |  |  | 195 |  |  |  |  | 200 |  |  |  |

```
gac cag ctg agc atc aat act ttt gga aag ttt tta gca gac aac aga      675
Asp Gln Leu Ser Ile Asn Thr Phe Gly Lys Phe Leu Ala Asp Asn Arg
            205                 210                 215 tct tgt gac aaa act cac aca tgc cca ccg tgc cca gca cct gaa gcc      723
Ser Cys Asp Lys Thr His Thr Cys Pro Pro Cys Pro Ala Pro Glu Ala
        220                 225                 230 gag ggc gcg ccg tca gtc ttc ctc ttc ccc cca aaa ccc aag gac acc      771
Glu Gly Ala Pro Ser Val Phe Leu Phe Pro Pro Lys Pro Lys Asp Thr
    235                 240                 245 ctc atg atc tcc cgg acc cct gag gtc aca tgc gtg gtg gtg gac gtg      819
Leu Met Ile Ser Arg Thr Pro Glu Val Thr Cys Val Val Val Asp Val
250                 255                 260                 265 agc cac gaa gac cct gag gtc aag ttc aac tgg tac gtg gac ggc gtg      867
Ser His Glu Asp Pro Glu Val Lys Phe Asn Trp Tyr Val Asp Gly Val
                270                 275                 280 gag gtg cat aat gcc aag aca aag ccg cgg gag gag cag tac aac agc      915
Glu Val His Asn Ala Lys Thr Lys Pro Arg Glu Glu Gln Tyr Asn Ser
            285                 290                 295 acg tac cgg gtg gtc agc gtc ctc acc gtc ctg cac cag gac tgg ctg      963
Thr Tyr Arg Val Val Ser Val Leu Thr Val Leu His Gln Asp Trp Leu
        300                 305                 310 aat ggc aag gag tac aag tgc aag gtc tcc aac aaa gcc ctc cca gcc     1011
Asn Gly Lys Glu Tyr Lys Cys Lys Val Ser Asn Lys Ala Leu Pro Ala
    315                 320                 325 ccc atc gag aaa acc atc tcc aaa gcc aaa ggg cag ccc cga gaa cca     1059
Pro Ile Glu Lys Thr Ile Ser Lys Ala Lys Gly Gln Pro Arg Glu Pro
330                 335                 340                 345 cag gtg tac acc ctg ccc cca tcc cgg gat gag ctg acc aag aac cag     1107
Gln Val Tyr Thr Leu Pro Pro Ser Arg Asp Glu Leu Thr Lys Asn Gln
                350                 355                 360 gtc agc ctg acc tgc ctg gtc aaa ggc ttc tat ccc agc gac atc gcc     1155
Val Ser Leu Thr Cys Leu Val Lys Gly Phe Tyr Pro Ser Asp Ile Ala
            365                 370                 375 gtg gag tgg gag agc aat ggg cag ccg gag aac aac tac aag acc acg     1203
Val Glu Trp Glu Ser Asn Gly Gln Pro Glu Asn Asn Tyr Lys Thr Thr
        380                 385                 390 cct ccc gtg ctg gac tcc gac ggc tcc ttc ttc ctc tac agc aag ctc     1251
Pro Pro Val Leu Asp Ser Asp Gly Ser Phe Phe Leu Tyr Ser Lys Leu
    395                 400                 405 acc gtg gac aag agc agg tgg cag cag ggg aac gtc ttc tca tgc tcc     1299
Thr Val Asp Lys Ser Arg Trp Gln Gln Gly Asn Val Phe Ser Cys Ser
410                 415                 420                 425 gtg atg cat gag gct ctg cac aac cac tac acg cag aag agc ctc tcc     1347
Val Met His Glu Ala Leu His Asn His Tyr Thr Gln Lys Ser Leu Ser
                430                 435                 440 ctg tct ccg ggt aaa tga actagagcgg ccgctacaga t                    1386
Leu Ser Pro Gly Lys
            445
```

<210> SEQ ID NO 10
<211> LENGTH: 446
<212> TYPE: PRT
<213> ORGANISM: Artificial Sequence
<220> FEATURE:
<223> OTHER INFORMATION: Fusion Construct

<400> SEQUENCE: 10

```
Met Glu Thr Asp Thr Leu Leu Leu Trp Val Leu Leu Leu Trp Val Pro
1               5                   10                  15
```

-continued

Gly Ser Thr Gly Thr Ser Cys Gly Asn Ser Arg Val Asp Glu Gly Glu
        20                  25                  30

Glu Cys Asp Pro Gly Ile Met Tyr Leu Asn Asn Asp Thr Cys Cys Asn
        35                  40                  45

Ser Asp Cys Thr Leu Lys Glu Gly Val Gln Cys Ser Asp Arg Asn Ser
    50                  55                  60

Pro Cys Cys Lys Asn Cys Gln Phe Glu Thr Ala Gln Lys Lys Cys Gln
65                  70                  75                  80

Glu Ala Ile Asn Ala Thr Cys Lys Gly Val Ser Tyr Cys Thr Gly Asn
                85                  90                  95

Ser Ser Glu Cys Pro Pro Gly Asn Ala Glu Asp Asp Thr Val Cys
            100                 105                 110

Leu Asp Leu Gly Lys Cys Lys Asp Gly Lys Cys Ile Pro Phe Cys Glu
            115                 120                 125

Arg Glu Gln Gln Leu Glu Ser Cys Ala Cys Asn Glu Thr Asp Asn Ser
        130                 135                 140

Cys Lys Val Cys Arg Asp Leu Ser Gly Arg Cys Val Pro Tyr Val
145                 150                 155                 160

Asp Ala Glu Gln Lys Asn Leu Phe Leu Arg Lys Gly Lys Pro Cys Thr
                165                 170                 175

Val Gly Phe Cys Asp Met Asn Gly Lys Cys Glu Lys Arg Val Gln Asp
            180                 185                 190

Val Ile Glu Arg Phe Trp Asp Phe Ile Asp Gln Leu Ser Ile Asn Thr
        195                 200                 205

Phe Gly Lys Phe Leu Ala Asp Asn Arg Ser Cys Asp Lys Thr His Thr
    210                 215                 220

Cys Pro Pro Cys Pro Ala Pro Glu Ala Glu Gly Ala Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 11
<211> LENGTH: 1653
<212> TYPE: DNA
<213> ORGANISM: Artificial Sequence
<220> FEATURE:
<223> OTHER INFORMATION: Fusion Construct
<221> NAME/KEY: CDS
<222> LOCATION: (25)..(1362)
<223> OTHER INFORMATION:

<400> SEQUENCE: 11

```
gtcgacccaa gctggctagc cacc atg gag aca gac aca ctc ctg cta tgg           51
                         Met Glu Thr Asp Thr Leu Leu Leu Trp
                           1               5 gta ctg ctg ctc tgg gtt cca ggt tcc act ggt act agt tgt ggg aat          99
Val Leu Leu Leu Trp Val Pro Gly Ser Thr Gly Thr Ser Cys Gly Asn
 10              15                  20                  25 cta gtg gtt gaa gaa ggg gag gaa tgt gac tgt gga acc ata cgg cag         147
Leu Val Val Glu Glu Gly Glu Glu Cys Asp Cys Gly Thr Ile Arg Gln
             30                  35                  40 tgt gca aaa gat ccc tgt tgt ctg tta aac tgt act cta cat cct ggg         195
Cys Ala Lys Asp Pro Cys Cys Leu Leu Asn Cys Thr Leu His Pro Gly
         45                  50                  55 gct gct tgt gct ttt gga ata tgt tgc aaa gac tgc aaa ttt ctg cca         243
Ala Ala Cys Ala Phe Gly Ile Cys Cys Lys Asp Cys Lys Phe Leu Pro
     60                  65                  70 tca gga act tta tgt aga caa caa gtt ggt gaa tgt gac ctt cca gag         291
Ser Gly Thr Leu Cys Arg Gln Gln Val Gly Glu Cys Asp Leu Pro Glu
 75                  80                  85 tgg tgc aat ggg aca tcc cat caa tgc cca gat gat gtg tat gtg cag         339
Trp Cys Asn Gly Thr Ser His Gln Cys Pro Asp Asp Val Tyr Val Gln
 90                  95                 100                 105 gac ggg atc tcc tgt aat gtg aat gcc ttc tgc tat gaa aag acg tgt         387
Asp Gly Ile Ser Cys Asn Val Asn Ala Phe Cys Tyr Glu Lys Thr Cys
                110                 115                 120 aat aac cat gat ata caa tgt aaa gag att ttt ggc caa gat gca agg         435
Asn Asn His Asp Ile Gln Cys Lys Glu Ile Phe Gly Gln Asp Ala Arg
            125                 130                 135 agt gca tct cag agt tgc tac caa gaa atc aac acc caa gga aac cgt         483
Ser Ala Ser Gln Ser Cys Tyr Gln Glu Ile Asn Thr Gln Gly Asn Arg
        140                 145                 150 ttc ggt cac tgt ggt att gta ggc aca aca tat gta aaa tgt tgg acc         531
Phe Gly His Cys Gly Ile Val Gly Thr Thr Tyr Val Lys Cys Trp Thr
155                 160                 165 cct gat atc atg tgt ggg agg gtt cag tgt gaa aat gtg gga gta att         579
Pro Asp Ile Met Cys Gly Arg Val Gln Cys Glu Asn Val Gly Val Ile
170                 175                 180                 185 ccc aat ctg ata gag cat tct aca gtg cag cag ttt cac ctc aat gac         627
Pro Asn Leu Ile Glu His Ser Thr Val Gln Gln Phe His Leu Asn Asp
                190                 195                 200 acc act tgc tgg ggc act gat tat cat tta ggg atg gct ata cct gat         675
Thr Thr Cys Trp Gly Thr Asp Tyr His Leu Gly Met Ala Ile Pro Asp
            205                 210                 215 att ggt gag gtg aaa gat ggc aca gta tgt ggt cca gaa aag atc tgc         723
Ile Gly Glu Val Lys Asp Gly Thr Val Cys Gly Pro Glu Lys Ile Cys
        220                 225                 230 atc cgt aag aag tgt gcc agt atg gtt cat ctg tca caa gcc tgt cag         771
Ile Arg Lys Lys Cys Ala Ser Met Val His Leu Ser Gln Ala Cys Gln
    235                 240                 245
```

```
cct aag acc tgc aac atg agg gga atc tgc aac aac aaa caa cac tgt      819
Pro Lys Thr Cys Asn Met Arg Gly Ile Cys Asn Asn Lys Gln His Cys
250                 255                 260                 265 cac tgc aac cat gaa tgg gca ccc cca tac tgc aag gac aaa ggc tat      867
His Cys Asn His Glu Trp Ala Pro Pro Tyr Cys Lys Asp Lys Gly Tyr
                270                 275                 280 gga ggt agt gct gat agt ggc cca cct cct aag aac aac atg gaa gga      915
Gly Gly Ser Ala Asp Ser Gly Pro Pro Pro Lys Asn Asn Met Glu Gly
            285                 290                 295 tta aat gtg atg gga aag ttg cgt gga tct tgt gac aaa act cac aca      963
Leu Asn Val Met Gly Lys Leu Arg Gly Ser Cys Asp Lys Thr His Thr
        300                 305                 310 tgc cca ccg tgc cca gca cct gaa gcc gag ggc gcg ccg tca gtc ttc     1011
Cys Pro Pro Cys Pro Ala Pro Glu Ala Glu Gly Ala Pro Ser Val Phe
    315                 320                 325 ctc ttc ccc cca aaa ccc aag gac acc ctc atg atc tcc cgg acc cct     1059
Leu Phe Pro Pro Lys Pro Lys Asp Thr Leu Met Ile Ser Arg Thr Pro
330                 335                 340                 345 gag gtc aca tgc gtg gtg gtg gac gtg agc cac gaa gac cct gag gtc     1107
Glu Val Thr Cys Val Val Val Asp Val Ser His Glu Asp Pro Glu Val
                350                 355                 360 aag ttc aac tgg tac gtg gac ggc gtg gag gtg cat aat gcc aag aca     1155
Lys Phe Asn Trp Tyr Val Asp Gly Val Glu Val His Asn Ala Lys Thr
            365                 370                 375 aag ccg cgg gag gag cag tac aac agc acg tac cgg gtg gtc agc gtc     1203
Lys Pro Arg Glu Glu Gln Tyr Asn Ser Thr Tyr Arg Val Val Ser Val
        380                 385                 390 ctc acc gtc ctg cac cag gac tgg ctg aat ggc aag gag tac aag tgc     1251
Leu Thr Val Leu His Gln Asp Trp Leu Asn Gly Lys Glu Tyr Lys Cys
    395                 400                 405 aag gtc tcc aac aaa gcc ctc cca gcc ccc atc gag aaa acc atc tcc     1299
Lys Val Ser Asn Lys Ala Leu Pro Ala Pro Ile Glu Lys Thr Ile Ser
410                 415                 420                 425 aaa gcc aaa ggg cag ccc cga gaa cca cag gtg tac acc ctg ccc cca     1347
Lys Ala Lys Gly Gln Pro Arg Glu Pro Gln Val Tyr Thr Leu Pro Pro
                430                 435                 440 tcc cgg gat gag ctg accaagaacc aggtcagcct gacctgcctg gtcaaaggct     1402
Ser Arg Asp Glu Leu
                445 tctatcccag cgacatcgcc gtggagtggg agagcaatgg gcagccggag aacaactaca   1462 agaccacgcc tcccgtgctg gactccgacg gctccttctt cctctacagc aagctcaccg   1522 tggacaagag caggtggcag caggggaacg tcttctcatg ctccgtgatg catgaggctc   1582 tgcacaacca ctacacgcag aagagcctct ccctgtctcc gggtaaatga actagagcgg   1642 ccgctacaga t                                                        1653

<210> SEQ ID NO 12
<211> LENGTH: 446
<212> TYPE: PRT
<213> ORGANISM: Artificial Sequence
<220> FEATURE:
<223> OTHER INFORMATION: Fusion Construct

<400> SEQUENCE: 12

Met Glu Thr Asp Thr Leu Leu Leu Trp Val Leu Leu Leu Trp Val Pro
1               5                   10                  15

Gly Ser Thr Gly Thr Ser Cys Gly Asn Leu Val Val Glu Glu Gly Glu
            20                  25                  30
```

```
Glu Cys Asp Cys Gly Thr Ile Arg Gln Cys Ala Lys Asp Pro Cys Cys
        35                  40                  45
Leu Leu Asn Cys Thr Leu His Pro Gly Ala Ala Cys Ala Phe Gly Ile
        50                  55                  60
Cys Cys Lys Asp Cys Lys Phe Leu Pro Ser Gly Thr Leu Cys Arg Gln
65                  70                  75                  80
Gln Val Gly Glu Cys Asp Leu Pro Glu Trp Cys Asn Gly Thr Ser His
                85                  90                  95
Gln Cys Pro Asp Asp Val Tyr Val Gln Asp Gly Ile Ser Cys Asn Val
                100                 105                 110
Asn Ala Phe Cys Tyr Glu Lys Thr Cys Asn Asn His Asp Ile Gln Cys
            115                 120                 125
Lys Glu Ile Phe Gly Gln Asp Ala Arg Ser Ala Ser Gln Ser Cys Tyr
        130                 135                 140
Gln Glu Ile Asn Thr Gln Gly Asn Arg Phe Gly His Cys Gly Ile Val
145                 150                 155                 160
Gly Thr Thr Tyr Val Lys Cys Trp Thr Pro Asp Ile Met Cys Gly Arg
                165                 170                 175
Val Gln Cys Glu Asn Val Gly Val Ile Pro Asn Leu Ile Glu His Ser
            180                 185                 190
Thr Val Gln Gln Phe His Leu Asn Asp Thr Thr Cys Trp Gly Thr Asp
        195                 200                 205
Tyr His Leu Gly Met Ala Ile Pro Asp Ile Gly Glu Val Lys Asp Gly
        210                 215                 220
Thr Val Cys Gly Pro Glu Lys Ile Cys Ile Arg Lys Lys Cys Ala Ser
225                 230                 235                 240
Met Val His Leu Ser Gln Ala Cys Gln Pro Lys Thr Cys Asn Met Arg
                245                 250                 255
Gly Ile Cys Asn Asn Lys Gln His Cys His Cys Asn His Glu Trp Ala
            260                 265                 270
Pro Pro Tyr Cys Lys Asp Lys Gly Tyr Gly Gly Ser Ala Asp Ser Gly
        275                 280                 285
Pro Pro Lys Asn Asn Met Glu Gly Leu Asn Val Met Gly Lys Leu
        290                 295                 300
Arg Gly Ser Cys Asp Lys Thr His Thr Cys Pro Pro Cys Pro Ala Pro
305                 310                 315                 320
Glu Ala Glu Gly Ala Pro Ser Val Phe Leu Phe Pro Pro Lys Pro Lys
                325                 330                 335
Asp Thr Leu Met Ile Ser Arg Thr Pro Glu Val Thr Cys Val Val Val
            340                 345                 350
Asp Val Ser His Glu Asp Pro Glu Val Lys Phe Asn Trp Tyr Val Asp
        355                 360                 365
Gly Val Glu Val His Asn Ala Lys Thr Lys Pro Arg Glu Glu Gln Tyr
        370                 375                 380
Asn Ser Thr Tyr Arg Val Val Ser Val Leu Thr Val Leu His Gln Asp
385                 390                 395                 400
Trp Leu Asn Gly Lys Glu Tyr Lys Cys Lys Val Ser Asn Lys Ala Leu
                405                 410                 415
Pro Ala Pro Ile Glu Lys Thr Ile Ser Lys Ala Lys Gly Gln Pro Arg
            420                 425                 430
Glu Pro Gln Val Tyr Thr Leu Pro Pro Ser Arg Asp Glu Leu
        435                 440                 445
```

-continued

<210> SEQ ID NO 13
<211> LENGTH: 1617
<212> TYPE: DNA
<213> ORGANISM: Artificial Sequence
<220> FEATURE:
<223> OTHER INFORMATION: Fusion Construct
<221> NAME/KEY: CDS
<222> LOCATION: (25)..(1596)
<223> OTHER INFORMATION:

<400> SEQUENCE: 13

```
gtcgacccaa gctggctagc cacc atg gag aca gac aca ctc ctg cta tgg         51
                          Met Glu Thr Asp Thr Leu Leu Leu Trp
                           1               5 gta ctg ctg ctc tgg gtt cca ggt tcc act ggt act agt tgt ggg aat         99
Val Leu Leu Leu Trp Val Pro Gly Ser Thr Gly Thr Ser Cys Gly Asn
 10              15                  20                  25 ggt gtg gtt gaa aga gaa gag cag tgt gac tgt gga tcc gta cag cag        147
Gly Val Val Glu Arg Glu Glu Gln Cys Asp Cys Gly Ser Val Gln Gln
             30                  35                  40 tgt gaa caa gac gcc tgt tgt ctg ttg aac tgc act cta agg cct ggg        195
Cys Glu Gln Asp Ala Cys Cys Leu Leu Asn Cys Thr Leu Arg Pro Gly
         45                  50                  55 gct gcc tgt gct ttt ggg ctt tgt tgc aaa gac tgc aag ttc atg cca        243
Ala Ala Cys Ala Phe Gly Leu Cys Cys Lys Asp Cys Lys Phe Met Pro
     60                  65                  70 tca ggg gaa ctc tgt aga caa gag gtc aat gaa tgt gac ctt cca gaa        291
Ser Gly Glu Leu Cys Arg Gln Glu Val Asn Glu Cys Asp Leu Pro Glu
 75                  80                  85 tgg tgc aat gga aca tct cat cag tgt cca gaa gat aga tat gtg cag        339
Trp Cys Asn Gly Thr Ser His Gln Cys Pro Glu Asp Arg Tyr Val Gln
 90                  95                 100                 105 gac ggg atc ccc tgt agt gac agt gcc tac tgc tat caa aag agg tgt        387
Asp Gly Ile Pro Cys Ser Asp Ser Ala Tyr Cys Tyr Gln Lys Arg Cys
                110                 115                 120 aat aac cat gac cag cat tgc agg gag att ttt ggt aaa gat gca aaa        435
Asn Asn His Asp Gln His Cys Arg Glu Ile Phe Gly Lys Asp Ala Lys
            125                 130                 135 agt gca tct cag aat tgc tat aaa gaa atc aac tct cag gga aac cgt        483
Ser Ala Ser Gln Asn Cys Tyr Lys Glu Ile Asn Ser Gln Gly Asn Arg
        140                 145                 150 ttt ggt cac tgt ggt ata aat ggc aca aca tac cta aaa tgt cat atc        531
Phe Gly His Cys Gly Ile Asn Gly Thr Thr Tyr Leu Lys Cys His Ile
    155                 160                 165 tct gat gtc ttt tgt ggg aga gtt caa tgt gag aat gtg aga gac att        579
Ser Asp Val Phe Cys Gly Arg Val Gln Cys Glu Asn Val Arg Asp Ile
170                 175                 180                 185 cct ctt ctc caa gat cat ttt act ttg cag cac act cat atc aat ggt        627
Pro Leu Leu Gln Asp His Phe Thr Leu Gln His Thr His Ile Asn Gly
                190                 195                 200 gtc acc tgc tgg ggt att gac tat cat tta agg atg aac ata tct gac        675
Val Thr Cys Trp Gly Ile Asp Tyr His Leu Arg Met Asn Ile Ser Asp
            205                 210                 215 att ggt gaa gtg aaa gat ggt act gtg tgt ggc cca gga aag atc tgc        723
Ile Gly Glu Val Lys Asp Gly Thr Val Cys Gly Pro Gly Lys Ile Cys
        220                 225                 230 atc cat aag aag tgt gtc agt ctg tct gtc ttg tca cat gtc tgc ctt        771
Ile His Lys Lys Cys Val Ser Leu Ser Val Leu Ser His Val Cys Leu
    235                 240                 245 cct gag acc tgc aat atg aag ggg atc tgc aat aac aaa cat cac tgc        819
Pro Glu Thr Cys Asn Met Lys Gly Ile Cys Asn Asn Lys His His Cys
250                 255                 260                 265
```

```
cac tgt ggc tat ggg tgg tcc cca ccc tac tgc cag cac aga ggc tat      867
His Cys Gly Tyr Gly Trp Ser Pro Pro Tyr Cys Gln His Arg Gly Tyr
                270                 275                 280 ggg ggc agt att gac agt ggc cca gca tct gca aag aga tct tgt gac      915
Gly Gly Ser Ile Asp Ser Gly Pro Ala Ser Ala Lys Arg Ser Cys Asp
            285                 290                 295 aaa act cac aca tgc cca ccg tgc cca gca cct gaa gcc gag ggc gcg      963
Lys Thr His Thr Cys Pro Pro Cys Pro Ala Pro Glu Ala Glu Gly Ala
        300                 305                 310 ccg tca gtc ttc ctc ttc ccc cca aaa ccc aag gac acc ctc atg atc     1011
Pro Ser Val Phe Leu Phe Pro Pro Lys Pro Lys Asp Thr Leu Met Ile
315                 320                 325 tcc cgg acc cct gag gtc aca tgc gtg gtg gtg gac gtg agc cac gaa     1059
Ser Arg Thr Pro Glu Val Thr Cys Val Val Val Asp Val Ser His Glu
330                 335                 340                 345 gac cct gag gtc aag ttc aac tgg tac gtg gac ggc gtg gag gtg cat     1107
Asp Pro Glu Val Lys Phe Asn Trp Tyr Val Asp Gly Val Glu Val His
                350                 355                 360 aat gcc aag aca aag ccg cgg gag gag cag tac aac agc acg tac cgg     1155
Asn Ala Lys Thr Lys Pro Arg Glu Glu Gln Tyr Asn Ser Thr Tyr Arg
            365                 370                 375 gtg gtc agc gtc ctc acc gtc ctg cac cag gac tgg ctg aat ggc aag     1203
Val Val Ser Val Leu Thr Val Leu His Gln Asp Trp Leu Asn Gly Lys
        380                 385                 390 gag tac aag tgc aag gtc tcc aac aaa gcc ctc cca gcc ccc atc gag     1251
Glu Tyr Lys Cys Lys Val Ser Asn Lys Ala Leu Pro Ala Pro Ile Glu
395                 400                 405 aaa acc atc tcc aaa gcc aaa ggg cag ccc cga gaa cca cag gtg tac     1299
Lys Thr Ile Ser Lys Ala Lys Gly Gln Pro Arg Glu Pro Gln Val Tyr
410                 415                 420                 425 acc ctg ccc cca tcc cgg gat gag ctg acc aag aac cag gtc agc ctg     1347
Thr Leu Pro Pro Ser Arg Asp Glu Leu Thr Lys Asn Gln Val Ser Leu
                430                 435                 440 acc tgc ctg gtc aaa ggc ttc tat ccc agc gac atc gcc gtg gag tgg     1395
Thr Cys Leu Val Lys Gly Phe Tyr Pro Ser Asp Ile Ala Val Glu Trp
            445                 450                 455 gag agc aat ggg cag ccg gag aac aac tac aag acc acg cct ccc gtg     1443
Glu Ser Asn Gly Gln Pro Glu Asn Asn Tyr Lys Thr Thr Pro Pro Val
        460                 465                 470 ctg gac tcc gac ggc tcc ttc ttc ctc tac agc aag ctc acc gtg gac     1491
Leu Asp Ser Asp Gly Ser Phe Phe Leu Tyr Ser Lys Leu Thr Val Asp
475                 480                 485 aag agc agg tgg cag cag ggg aac gtc ttc tca tgc tcc gtg atg cat     1539
Lys Ser Arg Trp Gln Gln Gly Asn Val Phe Ser Cys Ser Val Met His
490                 495                 500                 505 gag gct ctg cac aac cac tac acg cag aag agc ctc tcc ctg tct ccg     1587
Glu Ala Leu His Asn His Tyr Thr Gln Lys Ser Leu Ser Leu Ser Pro
                510                 515                 520 ggt aaa tga actagagcgg ccgctacaga t                                  1617
Gly Lys
```

<210> SEQ ID NO 14
<211> LENGTH: 523
<212> TYPE: PRT
<213> ORGANISM: Artificial Sequence
<220> FEATURE:
<223> OTHER INFORMATION: Fusion Construct

<400> SEQUENCE: 14

Met Glu Thr Asp Thr Leu Leu Leu Trp Val Leu Leu Leu Trp Val Pro

-continued

```
1               5                   10                  15
Gly Ser Thr Gly Thr Ser Cys Gly Asn Gly Val Glu Arg Glu
                20                  25                  30
Gln Cys Asp Cys Gly Ser Val Gln Gln Cys Glu Gln Asp Ala Cys Cys
                35                  40                  45
Leu Leu Asn Cys Thr Leu Arg Pro Gly Ala Ala Cys Ala Phe Gly Leu
    50                  55                  60
Cys Cys Lys Asp Cys Lys Phe Met Pro Ser Gly Glu Leu Cys Arg Gln
65                  70                  75                  80
Glu Val Asn Glu Cys Asp Leu Pro Glu Trp Cys Asn Gly Thr Ser His
                85                  90                  95
Gln Cys Pro Glu Asp Arg Tyr Val Gln Asp Gly Ile Pro Cys Ser Asp
                100                 105                 110
Ser Ala Tyr Cys Tyr Gln Lys Arg Cys Asn Asn His Asp Gln His Cys
                115                 120                 125
Arg Glu Ile Phe Gly Lys Asp Ala Lys Ser Ala Ser Gln Asn Cys Tyr
                130                 135                 140
Lys Glu Ile Asn Ser Gln Gly Asn Arg Phe Gly His Cys Gly Ile Asn
145                 150                 155                 160
Gly Thr Thr Tyr Leu Lys Cys His Ile Ser Asp Val Phe Cys Gly Arg
                165                 170                 175
Val Gln Cys Glu Asn Val Arg Asp Ile Pro Leu Leu Gln Asp His Phe
                180                 185                 190
Thr Leu Gln His Thr His Ile Asn Gly Val Thr Cys Trp Gly Ile Asp
                195                 200                 205
Tyr His Leu Arg Met Asn Ile Ser Asp Ile Gly Glu Val Lys Asp Gly
                210                 215                 220
Thr Val Cys Gly Pro Gly Lys Ile Cys Ile His Lys Lys Cys Val Ser
225                 230                 235                 240
Leu Ser Val Leu Ser His Val Cys Leu Pro Glu Thr Cys Asn Met Lys
                245                 250                 255
Gly Ile Cys Asn Asn Lys His Ser Cys His Cys Gly Tyr Gly Trp Ser
                260                 265                 270
Pro Pro Tyr Cys Gln His Arg Gly Tyr Gly Gly Ser Ile Asp Ser Gly
                275                 280                 285
Pro Ala Ser Ala Lys Arg Ser Cys Asp Lys Thr His Thr Cys Pro Pro
                290                 295                 300
Cys Pro Ala Pro Glu Ala Glu Gly Ala Pro Ser Val Phe Leu Phe Pro
305                 310                 315                 320
Pro Lys Pro Lys Asp Thr Leu Met Ile Ser Arg Thr Pro Glu Val Thr
                325                 330                 335
Cys Val Val Val Asp Val Ser His Glu Asp Pro Glu Val Lys Phe Asn
                340                 345                 350
Trp Tyr Val Asp Gly Val Glu Val His Asn Ala Lys Thr Lys Pro Arg
                355                 360                 365
Glu Glu Gln Tyr Asn Ser Thr Tyr Arg Val Val Ser Val Leu Thr Val
                370                 375                 380
Leu His Gln Asp Trp Leu Asn Gly Lys Glu Tyr Lys Cys Lys Val Ser
385                 390                 395                 400
Asn Lys Ala Leu Pro Ala Pro Ile Glu Lys Thr Ile Ser Lys Ala Lys
                405                 410                 415
Gly Gln Pro Arg Glu Pro Gln Val Tyr Thr Leu Pro Pro Ser Arg Asp
                420                 425                 430
```

```
Glu Leu Thr Lys Asn Gln Val Ser Leu Thr Cys Leu Val Lys Gly Phe
            435                 440                 445

Tyr Pro Ser Asp Ile Ala Val Glu Trp Glu Ser Asn Gly Gln Pro Glu
        450                 455                 460

Asn Asn Tyr Lys Thr Thr Pro Pro Val Leu Asp Ser Asp Gly Ser Phe
465                 470                 475                 480

Phe Leu Tyr Ser Lys Leu Thr Val Asp Lys Ser Arg Trp Gln Gln Gly
                485                 490                 495

Asn Val Phe Ser Cys Ser Val Met His Glu Ala Leu His Asn His Tyr
            500                 505                 510

Thr Gln Lys Ser Leu Ser Leu Ser Pro Gly Lys
        515                 520

<210> SEQ ID NO 15
<211> LENGTH: 1674
<212> TYPE: DNA
<213> ORGANISM: Artificial Sequence
<220> FEATURE:
<223> OTHER INFORMATION: Fusion Construct
<221> NAME/KEY: CDS
<222> LOCATION: (25)..(1653)
<223> OTHER INFORMATION:

<400> SEQUENCE: 15
gtcgacccaa gctggctagc cacc atg gag aca gac aca ctc ctg cta tgg         51
                         Met Glu Thr Asp Thr Leu Leu Leu Trp
                          1               5 gta ctg ctg ctc tgg gtt cca ggt tcc act ggt act agt tgt ggc aat        99
Val Leu Leu Leu Trp Val Pro Gly Ser Thr Gly Thr Ser Cys Gly Asn
 10              15                  20                  25 ggc ttc att gaa act gga gag gag tgt gat tgt gga acc ccg gcc gaa       147
Gly Phe Ile Glu Thr Gly Glu Glu Cys Asp Cys Gly Thr Pro Ala Glu
                 30                  35                  40 tgt gtc ctt gaa gga gca gag tgt tgt aag aaa tgc acc ttg act caa       195
Cys Val Leu Glu Gly Ala Glu Cys Cys Lys Lys Cys Thr Leu Thr Gln
             45                  50                  55 gac tct caa tgc agt gac ggt ctt tgc tgt aaa aag tgc aag ttt cag       243
Asp Ser Gln Cys Ser Asp Gly Leu Cys Cys Lys Lys Cys Lys Phe Gln
         60                  65                  70 cct atg ggc act gtg tgc cga gaa gca gta aat gat tgt gat att cgt       291
Pro Met Gly Thr Val Cys Arg Glu Ala Val Asn Asp Cys Asp Ile Arg
 75                  80                  85 gaa acg tgc tca gga aat tca agc cag tgt gcc cct aat att cat aaa       339
Glu Thr Cys Ser Gly Asn Ser Ser Gln Cys Ala Pro Asn Ile His Lys
 90                  95                 100                 105 atg gat gga tat tca tgt gat ggt gtt cag gga att tgc ttt gga gga       387
Met Asp Gly Tyr Ser Cys Asp Gly Val Gln Gly Ile Cys Phe Gly Gly
                110                 115                 120 aga tgc aaa acc aga gat aga caa tgc aaa tac att tgg ggg caa aag       435
Arg Cys Lys Thr Arg Asp Arg Gln Cys Lys Tyr Ile Trp Gly Gln Lys
            125                 130                 135 gtg aca gca tca gac aaa tat tgc tat gag aaa ctg aat att gaa ggg       483
Val Thr Ala Ser Asp Lys Tyr Cys Tyr Glu Lys Leu Asn Ile Glu Gly
        140                 145                 150 acg gag aag ggt aac tgt ggg aaa gac aaa gac aca tgg ata cag tgc       531
Thr Glu Lys Gly Asn Cys Gly Lys Asp Lys Asp Thr Trp Ile Gln Cys
    155                 160                 165 aac aaa cgg gat gtg ctt tgt ggt tac ctt ttg tgt acc aat att ggc       579
Asn Lys Arg Asp Val Leu Cys Gly Tyr Leu Leu Cys Thr Asn Ile Gly
170                 175                 180                 185
```

```
aat atc cca agg ctt gga gaa ctc gat ggt gaa atc aca tct act tta      627
Asn Ile Pro Arg Leu Gly Glu Leu Asp Gly Glu Ile Thr Ser Thr Leu
            190                 195                 200 gtt gtg cag caa gga aga aca tta aac tgc agt ggt ggg cat gtt aag      675
Val Val Gln Gln Gly Arg Thr Leu Asn Cys Ser Gly Gly His Val Lys
        205                 210                 215 ctt gaa gaa gat gta gat ctt ggc tat gtg gaa gat ggg aca cct tgt      723
Leu Glu Glu Asp Val Asp Leu Gly Tyr Val Glu Asp Gly Thr Pro Cys
        220                 225                 230 ggt ccc caa atg atg tgc tta gaa cac agg tgt ctt cct gtg gct tct      771
Gly Pro Gln Met Met Cys Leu Glu His Arg Cys Leu Pro Val Ala Ser
235                 240                 245 ttc aac ttt agt act tgc ttg agc agt aaa gaa ggc act att tgc tca      819
Phe Asn Phe Ser Thr Cys Leu Ser Ser Lys Glu Gly Thr Ile Cys Ser
250                 255                 260                 265 gga aat gga gtt tgc agt aat gag ctg aag tgt gtg tgt aac aga cac      867
Gly Asn Gly Val Cys Ser Asn Glu Leu Lys Cys Val Cys Asn Arg His
            270                 275                 280 tgg ata ggt tct gat tgc aac act tac ttc cct cac aat gat gat gca      915
Trp Ile Gly Ser Asp Cys Asn Thr Tyr Phe Pro His Asn Asp Asp Ala
            285                 290                 295 aag act ggt atc act ctg tct ggc aat ggt gtt gct ggc acc aat gga      963
Lys Thr Gly Ile Thr Leu Ser Gly Asn Gly Val Ala Gly Thr Asn Gly
        300                 305                 310 tct tgt gac aaa act cac aca tgc cca ccg tgc cca gca cct gaa gcc     1011
Ser Cys Asp Lys Thr His Thr Cys Pro Pro Cys Pro Ala Pro Glu Ala
        315                 320                 325 gag ggc gcg ccg tca gtc ttc ctc ttc ccc cca aaa ccc aag gac acc     1059
Glu Gly Ala Pro Ser Val Phe Leu Phe Pro Pro Lys Pro Lys Asp Thr
330                 335                 340                 345 ctc atg atc tcc cgg acc cct gag gtc aca tgc gtg gtg gtg gac gtg     1107
Leu Met Ile Ser Arg Thr Pro Glu Val Thr Cys Val Val Val Asp Val
            350                 355                 360 agc cac gaa gac cct gag gtc aag ttc aac tgg tac gtg gac ggc gtg     1155
Ser His Glu Asp Pro Glu Val Lys Phe Asn Trp Tyr Val Asp Gly Val
            365                 370                 375 gag gtg cat aat gcc aag aca aag ccg cgg gag gag cag tac aac agc     1203
Glu Val His Asn Ala Lys Thr Lys Pro Arg Glu Glu Gln Tyr Asn Ser
        380                 385                 390 acg tac cgg gtg gtc agc gtc ctc acc gtc ctg cac cag gac tgg ctg     1251
Thr Tyr Arg Val Val Ser Val Leu Thr Val Leu His Gln Asp Trp Leu
        395                 400                 405 aat ggc aag gag tac aag tgc aag gtc tcc aac aaa gcc ctc cca gcc     1299
Asn Gly Lys Glu Tyr Lys Cys Lys Val Ser Asn Lys Ala Leu Pro Ala
410                 415                 420                 425 ccc atc gag aaa acc atc tcc aaa gcc aaa ggg cag ccc cga gaa cca     1347
Pro Ile Glu Lys Thr Ile Ser Lys Ala Lys Gly Gln Pro Arg Glu Pro
            430                 435                 440 cag gtg tac acc ctg ccc cca tcc cgg gat gag ctg acc aag aac cag     1395
Gln Val Tyr Thr Leu Pro Pro Ser Arg Asp Glu Leu Thr Lys Asn Gln
            445                 450                 455 gtc agc ctg acc tgc ctg gtc aaa ggc ttc tat ccc agc gac atc gcc     1443
Val Ser Leu Thr Cys Leu Val Lys Gly Phe Tyr Pro Ser Asp Ile Ala
        460                 465                 470 gtg gag tgg gag agc aat ggg cag ccg gag aac aac tac aag acc acg     1491
Val Glu Trp Glu Ser Asn Gly Gln Pro Glu Asn Asn Tyr Lys Thr Thr
475                 480                 485 cct ccc gtg ctg gac tcc gac ggc tcc ttc ttc ctc tac agc aag ctc     1539
Pro Pro Val Leu Asp Ser Asp Gly Ser Phe Phe Leu Tyr Ser Lys Leu
```

-continued

```
                490                 495                 500                 505
acc gtg gac aag agc agg tgg cag cag ggg aac gtc ttc tca tgc tcc      1587
Thr Val Asp Lys Ser Arg Trp Gln Gln Gly Asn Val Phe Ser Cys Ser
                510                 515                 520 gtg atg cat gag gct ctg cac aac cac tac acg cag aag agc ctc tcc      1635
Val Met His Glu Ala Leu His Asn His Tyr Thr Gln Lys Ser Leu Ser
            525                 530                 535 ctg tct ccg ggt aaa tga actagagcgg ccgctacaga t                      1674
Leu Ser Pro Gly Lys
        540
```

<210> SEQ ID NO 16
<211> LENGTH: 542
<212> TYPE: PRT
<213> ORGANISM: Artificial Sequence
<220> FEATURE:
<223> OTHER INFORMATION: Fusion Construct

<400> SEQUENCE: 16

Met Glu Thr Asp Thr Leu Leu Leu Trp Val Leu Leu Leu Trp Val Pro
1               5                   10                  15

Gly Ser Thr Gly Thr Ser Cys Gly Asn Gly Phe Ile Glu Thr Gly Glu
            20                  25                  30

Glu Cys Asp Cys Gly Thr Pro Ala Glu Cys Val Leu Glu Gly Ala Glu
        35                  40                  45

Cys Cys Lys Lys Cys Thr Leu Thr Gln Asp Ser Gln Cys Ser Asp Gly
    50                  55                  60

Leu Cys Cys Lys Lys Cys Lys Phe Gln Pro Met Gly Thr Val Cys Arg
65                  70                  75                  80

Glu Ala Val Asn Asp Cys Asp Ile Arg Glu Thr Cys Ser Gly Asn Ser
                85                  90                  95

Ser Gln Cys Ala Pro Asn Ile His Lys Met Asp Gly Tyr Ser Cys Asp
            100                 105                 110

Gly Val Gln Gly Ile Cys Phe Gly Gly Arg Cys Lys Thr Arg Asp Arg
        115                 120                 125

Gln Cys Lys Tyr Ile Trp Gly Gln Lys Val Thr Ala Ser Asp Lys Tyr
    130                 135                 140

Cys Tyr Glu Lys Leu Asn Ile Glu Gly Thr Glu Lys Gly Asn Cys Gly
145                 150                 155                 160

Lys Asp Lys Asp Thr Trp Ile Gln Cys Asn Lys Arg Asp Val Leu Cys
                165                 170                 175

Gly Tyr Leu Leu Cys Thr Asn Ile Gly Asn Ile Pro Arg Leu Gly Glu
            180                 185                 190

Leu Asp Gly Glu Ile Thr Ser Thr Leu Val Val Gln Gln Gly Arg Thr
        195                 200                 205

Leu Asn Cys Ser Gly Gly His Val Lys Leu Glu Glu Asp Val Asp Leu
    210                 215                 220

Gly Tyr Val Glu Asp Gly Thr Pro Cys Gly Pro Gln Met Met Cys Leu
225                 230                 235                 240

Glu His Arg Cys Leu Pro Val Ala Ser Phe Asn Phe Ser Thr Cys Leu
                245                 250                 255

Ser Ser Lys Glu Gly Thr Ile Cys Ser Gly Asn Gly Val Cys Ser Asn
            260                 265                 270

Glu Leu Lys Cys Val Cys Asn Arg His Trp Ile Gly Ser Asp Cys Asn
        275                 280                 285

Thr Tyr Phe Pro His Asn Asp Asp Ala Lys Thr Gly Ile Thr Leu Ser

```
            290                 295                 300
Gly Asn Gly Val Ala Gly Thr Asn Gly Ser Cys Asp Lys Thr His Thr
305                 310                 315                 320

Cys Pro Pro Cys Pro Ala Pro Glu Ala Glu Gly Ala Pro Ser Val Phe
                325                 330                 335

Leu Phe Pro Pro Lys Pro Lys Asp Thr Leu Met Ile Ser Arg Thr Pro
            340                 345                 350

Glu Val Thr Cys Val Val Val Asp Val Ser His Glu Asp Pro Glu Val
        355                 360                 365

Lys Phe Asn Trp Tyr Val Asp Gly Val Glu Val His Asn Ala Lys Thr
370                 375                 380

Lys Pro Arg Glu Glu Gln Tyr Asn Ser Thr Tyr Arg Val Val Ser Val
385                 390                 395                 400

Leu Thr Val Leu His Gln Asp Trp Leu Asn Gly Lys Glu Tyr Lys Cys
                405                 410                 415

Lys Val Ser Asn Lys Ala Leu Pro Ala Pro Ile Glu Lys Thr Ile Ser
            420                 425                 430

Lys Ala Lys Gly Gln Pro Arg Glu Pro Gln Val Tyr Thr Leu Pro Pro
435                 440                 445

Ser Arg Asp Glu Leu Thr Lys Asn Gln Val Ser Leu Thr Cys Leu Val
        450                 455                 460

Lys Gly Phe Tyr Pro Ser Asp Ile Ala Val Glu Trp Glu Ser Asn Gly
465                 470                 475                 480

Gln Pro Glu Asn Asn Tyr Lys Thr Thr Pro Pro Val Leu Asp Ser Asp
                485                 490                 495

Gly Ser Phe Phe Leu Tyr Ser Lys Leu Thr Val Asp Lys Ser Arg Trp
            500                 505                 510

Gln Gln Gly Asn Val Phe Ser Cys Ser Val Met His Glu Ala Leu His
515                 520                 525

Asn His Tyr Thr Gln Lys Ser Leu Ser Leu Ser Pro Gly Lys
        530                 535                 540

<210> SEQ ID NO 17
<211> LENGTH: 1668
<212> TYPE: DNA
<213> ORGANISM: Artificial Sequence
<220> FEATURE:
<223> OTHER INFORMATION: Fusion Construct
<221> NAME/KEY: CDS
<222> LOCATION: (25)..(1647)
<223> OTHER INFORMATION:

<400> SEQUENCE: 17
gtcgacccaa gctggctagc cacc atg gag aca gac aca ctc ctg cta tgg         51
                         Met Glu Thr Asp Thr Leu Leu Leu Trp
                           1               5 gta ctg ctg ctc tgg gtt cca ggt tcc act ggt act agt tgt gga aat        99
Val Leu Leu Leu Trp Val Pro Gly Ser Thr Gly Thr Ser Cys Gly Asn
 10                  15                  20                  25 gga tac gtc gaa gct ggg gag gag tgt gat tgt ggt ttt cat gtg gaa       147
Gly Tyr Val Glu Ala Gly Glu Glu Cys Asp Cys Gly Phe His Val Glu
                 30                  35                  40 tgc tat gga tta tgc tgt aag aaa tgt tcc ctc tcc aac ggg gct cac       195
Cys Tyr Gly Leu Cys Cys Lys Lys Cys Ser Leu Ser Asn Gly Ala His
             45                  50                  55 tgc agc gac ggg ccc tgc tgt aac aat acc tca tgt ctt ttt cag cca       243
Cys Ser Asp Gly Pro Cys Cys Asn Asn Thr Ser Cys Leu Phe Gln Pro
         60                  65                  70
```

|  |  |
|---|---|
| cga ggg tat gaa tgc cgg gat gct gtg aac gag tgt gat att act gaa<br>Arg Gly Tyr Glu Cys Arg Asp Ala Val Asn Glu Cys Asp Ile Thr Glu<br>75                        80                  85 | 291 |
| tat tgt act gga gac tct ggt cag tgc cca cca aat ctt cat aag caa<br>Tyr Cys Thr Gly Asp Ser Gly Gln Cys Pro Pro Asn Leu His Lys Gln<br>90                    95                 100              105 | 339 |
| gac gga tat gca tgc aat caa aat cag ggc cgc tgc tac aat ggc gag<br>Asp Gly Tyr Ala Cys Asn Gln Asn Gln Gly Arg Cys Tyr Asn Gly Glu<br>               110                 115                120 | 387 |
| tgc aag gcc aga gac aac cag tgt cag tac atc tgg gga aca aag gct<br>Cys Lys Ala Arg Asp Asn Gln Cys Gln Tyr Ile Trp Gly Thr Lys Ala<br>         125                    130                135 | 435 |
| gca ggg tct gac aag ttc tgc tat gaa aag ctg aat aca gaa ggc act<br>Ala Gly Ser Asp Lys Phe Cys Tyr Glu Lys Leu Asn Thr Glu Gly Thr<br>140                     145                 150 | 483 |
| gag aag gga aac tgc ggg aag gat gga gac cgg tgg att cag tgc agc<br>Glu Lys Gly Asn Cys Gly Lys Asp Gly Asp Arg Trp Ile Gln Cys Ser<br>          155                    160              165 | 531 |
| aaa cat gat gtg ttc tgt gga ttc tta ctc tgt acc aat ctt act cga<br>Lys His Asp Val Phe Cys Gly Phe Leu Leu Cys Thr Asn Leu Thr Arg<br>170                     175                 180                185 | 579 |
| gct cca cgt att ggt caa ctt cag ggt gag atc att cca act tcc ttc<br>Ala Pro Arg Ile Gly Gln Leu Gln Gly Glu Ile Ile Pro Thr Ser Phe<br>               190                 195                200 | 627 |
| tac cat caa ggc cgg gtg att gac tgc agt ggt gcc cat gta gtt tta<br>Tyr His Gln Gly Arg Val Ile Asp Cys Ser Gly Ala His Val Val Leu<br>         205                    210                215 | 675 |
| gat gat gat acg gat gtg ggc tat gta gaa gat gga acg cca tgt ggc<br>Asp Asp Asp Thr Asp Val Gly Tyr Val Glu Asp Gly Thr Pro Cys Gly<br>220                     225                 230 | 723 |
| ccg tct atg atg tgt tta gat cgg aag tgc cta caa att caa gcc cta<br>Pro Ser Met Met Cys Leu Asp Arg Lys Cys Leu Gln Ile Gln Ala Leu<br>          235                    240                245 | 771 |
| aat atg agc agc tgt cca ctc gat tcc aag ggt aaa gtc tgt tcg ggc<br>Asn Met Ser Ser Cys Pro Leu Asp Ser Lys Gly Lys Val Cys Ser Gly<br>250                     255                 260                265 | 819 |
| cat ggg gtg tgt agt aat gaa gcc acc tgc att tgt gat ttc acc tgg<br>His Gly Val Cys Ser Asn Glu Ala Thr Cys Ile Cys Asp Phe Thr Trp<br>               270                 275                280 | 867 |
| gca ggg aca gat tgc agt atc cgg gat cca gtt agg aac ctt cac ccc<br>Ala Gly Thr Asp Cys Ser Ile Arg Asp Pro Val Arg Asn Leu His Pro<br>         285                    290                295 | 915 |
| ccc aag gat gaa gga ccc aag ggt cct agt gcc acc aat aga tct tgt<br>Pro Lys Asp Glu Gly Pro Lys Gly Pro Ser Ala Thr Asn Arg Ser Cys<br>300                     305                 310 | 963 |
| gac aaa act cac aca tgc cca ccg tgc cca gca cct gaa gcc gag ggc<br>Asp Lys Thr His Thr Cys Pro Pro Cys Pro Ala Pro Glu Ala Glu Gly<br>         315                    320                325 | 1011 |
| gcg ccg tca gtc ttc ctc ttc ccc cca aaa ccc aag gac acc ctc atg<br>Ala Pro Ser Val Phe Leu Phe Pro Pro Lys Pro Lys Asp Thr Leu Met<br>330                     335                 340                345 | 1059 |
| atc tcc cgg acc cct gag gtc aca tgc gtg gtg gtg gac gtg agc cac<br>Ile Ser Arg Thr Pro Glu Val Thr Cys Val Val Val Asp Val Ser His<br>               350                 355                360 | 1107 |
| gaa gac cct gag gtc aag ttc aac tgg tac gtg gac ggc gtg gag gtg<br>Glu Asp Pro Glu Val Lys Phe Asn Trp Tyr Val Asp Gly Val Glu Val<br>         365                    370                375 | 1155 |
| cat aat gcc aag aca aag ccg cgg gag gag cag tac aac agc acg tac<br>His Asn Ala Lys Thr Lys Pro Arg Glu Glu Gln Tyr Asn Ser Thr Tyr | 1203 |

```
                380                 385                 390
cgg gtg gtc agc gtc ctc acc gtc ctg cac cag gac tgg ctg aat ggc      1251
Arg Val Val Ser Val Leu Thr Val Leu His Gln Asp Trp Leu Asn Gly
    395                 400                 405 aag gag tac aag tgc aag gtc tcc aac aaa gcc ctc cca gcc ccc atc      1299
Lys Glu Tyr Lys Cys Lys Val Ser Asn Lys Ala Leu Pro Ala Pro Ile
410                 415                 420                 425 gag aaa acc atc tcc aaa gcc aaa ggg cag ccc cga gaa cca cag gtg      1347
Glu Lys Thr Ile Ser Lys Ala Lys Gly Gln Pro Arg Glu Pro Gln Val
            430                 435                 440 tac acc ctg ccc cca tcc cgg gat gag ctg acc aag aac cag gtc agc      1395
Tyr Thr Leu Pro Pro Ser Arg Asp Glu Leu Thr Lys Asn Gln Val Ser
                445                 450                 455 ctg acc tgc ctg gtc aaa ggc ttc tat ccc agc gac atc gcc gtg gag      1443
Leu Thr Cys Leu Val Lys Gly Phe Tyr Pro Ser Asp Ile Ala Val Glu
                460                 465                 470 tgg gag agc aat ggg cag ccg gag aac aac tac aag acc acg cct ccc      1491
Trp Glu Ser Asn Gly Gln Pro Glu Asn Asn Tyr Lys Thr Thr Pro Pro
475                 480                 485 gtg ctg gac tcc gac ggc tcc ttc ttc ctc tac agc aag ctc acc gtg      1539
Val Leu Asp Ser Asp Gly Ser Phe Phe Leu Tyr Ser Lys Leu Thr Val
490                 495                 500                 505 gac aag agc agg tgg cag cag ggg aac gtc ttc tca tgc tcc gtg atg      1587
Asp Lys Ser Arg Trp Gln Gln Gly Asn Val Phe Ser Cys Ser Val Met
            510                 515                 520 cat gag gct ctg cac aac cac tac acg cag aag agc ctc tcc ctg tct      1635
His Glu Ala Leu His Asn His Tyr Thr Gln Lys Ser Leu Ser Leu Ser
                525                 530                 535 ccg ggt aaa tga actagagcgg ccgctacaga t                              1668
Pro Gly Lys
        540

<210> SEQ ID NO 18
<211> LENGTH: 540
<212> TYPE: PRT
<213> ORGANISM: Artificial Sequence
<220> FEATURE:
<223> OTHER INFORMATION: Fusion Construct

<400> SEQUENCE: 18

Met Glu Thr Asp Thr Leu Leu Leu Trp Val Leu Leu Leu Trp Val Pro
1               5                   10                  15

Gly Ser Thr Gly Thr Ser Cys Gly Asn Gly Tyr Val Glu Ala Gly Glu
            20                  25                  30

Glu Cys Asp Cys Gly Phe His Val Glu Cys Tyr Gly Leu Cys Cys Lys
        35                  40                  45

Lys Cys Ser Leu Ser Asn Gly Ala His Cys Ser Asp Gly Pro Cys Cys
    50                  55                  60

Asn Asn Thr Ser Cys Leu Phe Gln Pro Arg Gly Tyr Glu Cys Arg Asp
65                  70                  75                  80

Ala Val Asn Glu Cys Asp Ile Thr Glu Tyr Cys Thr Gly Asp Ser Gly
                85                  90                  95

Gln Cys Pro Pro Asn Leu His Lys Gln Asp Gly Tyr Ala Cys Asn Gln
            100                 105                 110

Asn Gln Gly Arg Cys Tyr Asn Gly Glu Cys Lys Ala Arg Asp Asn Gln
        115                 120                 125

Cys Gln Tyr Ile Trp Gly Thr Lys Ala Ala Gly Ser Asp Lys Phe Cys
    130                 135                 140
```

```
Tyr Glu Lys Leu Asn Thr Glu Gly Thr Glu Lys Gly Asn Cys Gly Lys
145                 150                 155                 160

Asp Gly Asp Arg Trp Ile Gln Cys Ser Lys His Asp Val Phe Cys Gly
                165                 170                 175

Phe Leu Leu Cys Thr Asn Leu Thr Arg Ala Pro Arg Ile Gly Gln Leu
            180                 185                 190

Gln Gly Glu Ile Ile Pro Thr Ser Phe Tyr His Gln Gly Arg Val Ile
        195                 200                 205

Asp Cys Ser Gly Ala His Val Val Leu Asp Asp Thr Asp Val Gly
    210                 215                 220

Tyr Val Glu Asp Gly Thr Pro Cys Gly Pro Ser Met Met Cys Leu Asp
225                 230                 235                 240

Arg Lys Cys Leu Gln Ile Gln Ala Leu Asn Met Ser Ser Cys Pro Leu
                245                 250                 255

Asp Ser Lys Gly Lys Val Cys Ser Gly His Gly Val Cys Ser Asn Glu
            260                 265                 270

Ala Thr Cys Ile Cys Asp Phe Thr Trp Ala Gly Thr Asp Cys Ser Ile
        275                 280                 285

Arg Asp Pro Val Arg Asn Leu His Pro Lys Asp Glu Gly Pro Lys
290                 295                 300

Gly Pro Ser Ala Thr Asn Arg Ser Cys Asp Lys Thr His Thr Cys Pro
305                 310                 315                 320

Pro Cys Pro Ala Pro Glu Ala Glu Gly Ala Pro Ser Val Phe Leu Phe
                325                 330                 335

Pro Pro Lys Pro Lys Asp Thr Leu Met Ile Ser Arg Thr Pro Glu Val
            340                 345                 350

Thr Cys Val Val Val Asp Val Ser His Glu Asp Pro Glu Val Lys Phe
        355                 360                 365

Asn Trp Tyr Val Asp Gly Val Glu Val His Asn Ala Lys Thr Lys Pro
370                 375                 380

Arg Glu Glu Gln Tyr Asn Ser Thr Tyr Arg Val Val Ser Val Leu Thr
385                 390                 395                 400

Val Leu His Gln Asp Trp Leu Asn Gly Lys Glu Tyr Lys Cys Lys Val
                405                 410                 415

Ser Asn Lys Ala Leu Pro Ala Pro Ile Glu Lys Thr Ile Ser Lys Ala
            420                 425                 430

Lys Gly Gln Pro Arg Glu Pro Gln Val Tyr Thr Leu Pro Pro Ser Arg
        435                 440                 445

Asp Glu Leu Thr Lys Asn Gln Val Ser Leu Thr Cys Leu Val Lys Gly
    450                 455                 460

Phe Tyr Pro Ser Asp Ile Ala Val Glu Trp Glu Ser Asn Gly Gln Pro
465                 470                 475                 480

Glu Asn Asn Tyr Lys Thr Thr Pro Pro Val Leu Asp Ser Asp Gly Ser
                485                 490                 495

Phe Phe Leu Tyr Ser Lys Leu Thr Val Asp Lys Ser Arg Trp Gln Gln
            500                 505                 510

Gly Asn Val Phe Ser Cys Ser Val Met His Glu Ala Leu His Asn His
        515                 520                 525

Tyr Thr Gln Lys Ser Leu Ser Leu Ser Pro Gly Lys
530                 535                 540

<210> SEQ ID NO 19
<211> LENGTH: 3
<212> TYPE: PRT
```

```
<213> ORGANISM: Artificial Sequence
<220> FEATURE:
<223> OTHER INFORMATION: Consensus binding motif

<400> SEQUENCE: 19

Arg Gly Asp
1

<210> SEQ ID NO 20
<211> LENGTH: 67
<212> TYPE: PRT
<213> ORGANISM: Artificial Sequence
<220> FEATURE:
<223> OTHER INFORMATION: Consensus disintegrin domain
<221> NAME/KEY: MISC_FEATURE
<222> LOCATION: (5)..(9)
<223> OTHER INFORMATION: Xaa is 3-5 varying residues in a consensus
      sequence
<221> NAME/KEY: MISC_FEATURE
<222> LOCATION: (11)..(16)
<223> OTHER INFORMATION: Xaa is 3-6 varying residues in a consensus
      sequence
<221> NAME/KEY: MISC_FEATURE
<222> LOCATION: (19)..(22)
<223> OTHER INFORMATION: Xaa is 2-4 varying residues in a consensus
      sequence
<221> NAME/KEY: MISC_FEATURE
<222> LOCATION: (24)..(30)
<223> OTHER INFORMATION: Xaa is 7 varying residues in a consensus
      sequence
<221> NAME/KEY: MISC_FEATURE
<222> LOCATION: (32)..(37)
<223> OTHER INFORMATION: Xaa is 4-6 varying residues in a consensus
      sequence
<221> NAME/KEY: MISC_FEATURE
<222> LOCATION: (40)..(43)
<223> OTHER INFORMATION: Xaa is 2-4 varying residues in a consensus
      sequence
<221> NAME/KEY: MISC_FEATURE
<222> LOCATION: (45)..(52)
<223> OTHER INFORMATION: Xaa is 8 varying residues in a consensus
      sequence
<221> NAME/KEY: MISC_FEATURE
<222> LOCATION: (54)..(60)
<223> OTHER INFORMATION: Xaa is 5-7 varying residues in a consensus
      sequence
<221> NAME/KEY: MISC_FEATURE
<222> LOCATION: (62)..(66)
<223> OTHER INFORMATION: Xaa is 3-5 varying residues in a consensus
      sequence

<400> SEQUENCE: 20

Cys Asp Cys Gly Xaa Xaa Xaa Xaa Xaa Cys Xaa Xaa Xaa Xaa Xaa Xaa
1               5                   10                  15

Cys Cys Xaa Xaa Xaa Xaa Cys Xaa Xaa Xaa Xaa Xaa Xaa Xaa Cys Xaa
            20                  25                  30

Xaa Xaa Xaa Xaa Xaa Cys Cys Xaa Xaa Xaa Xaa Cys Xaa Xaa Xaa Xaa
        35                  40                  45

Xaa Xaa Xaa Xaa Cys Xaa Xaa Xaa Xaa Xaa Xaa Xaa Cys Xaa Xaa Xaa
    50                  55                  60

Xaa Xaa Cys
65

<210> SEQ ID NO 21
<211> LENGTH: 1725
<212> TYPE: DNA
<213> ORGANISM: Artificial Sequence
<220> FEATURE:
<223> OTHER INFORMATION: Fusion Construct
<221> NAME/KEY: CDS
<222> LOCATION: (118)..(1704)
```

<223> OTHER INFORMATION:

<400> SEQUENCE: 21

```
gggttttccc agtcacgacg ttgtaaaacg acggccagtg aattgtaata cgactcacta      60
tagggcgaat tgggtaccgg ccccccctc gaggtcgacc caagctggct agccacc         117
```

| | | | | | | | | | | | | | | | | |
|---|---|---|---|---|---|---|---|---|---|---|---|---|---|---|---|---|
| atg | gag | aca | gac | aca | ctc | ctg | cta | tgg | gta | ctg | ctg | ctc | tgg | gtt | cca | 165 |
| Met | Glu | Thr | Asp | Thr | Leu | Leu | Leu | Trp | Val | Leu | Leu | Leu | Trp | Val | Pro | |
| 1 | | | | 5 | | | | | 10 | | | | | 15 | | |
| ggt | tcc | act | ggt | act | agt | tgt | ggg | aat | ggt | gtg | gtt | gaa | gaa | gga | gaa | 213 |
| Gly | Ser | Thr | Gly | Thr | Ser | Cys | Gly | Asn | Gly | Val | Val | Glu | Glu | Gly | Glu | |
| | | | 20 | | | | | 25 | | | | | 30 | | | |
| gag | tgt | gac | tgt | gga | cct | tta | aag | cat | tgt | gca | aaa | gat | ccc | tgc | tgt | 261 |
| Glu | Cys | Asp | Cys | Gly | Pro | Leu | Lys | His | Cys | Ala | Lys | Asp | Pro | Cys | Cys | |
| | | 35 | | | | | 40 | | | | | 45 | | | | |
| ctg | tca | aat | tgc | act | ctg | act | gat | ggt | tct | act | tgt | gct | ttt | ggg | ctt | 309 |
| Leu | Ser | Asn | Cys | Thr | Leu | Thr | Asp | Gly | Ser | Thr | Cys | Ala | Phe | Gly | Leu | |
| | 50 | | | | | 55 | | | | | 60 | | | | | |
| tgt | tgc | aaa | gac | tgc | aag | ttc | cta | cca | tca | ggg | aaa | gtg | tgt | aga | aag | 357 |
| Cys | Cys | Lys | Asp | Cys | Lys | Phe | Leu | Pro | Ser | Gly | Lys | Val | Cys | Arg | Lys | |
| 65 | | | | | 70 | | | | | 75 | | | | | 80 | |
| gag | gtc | aat | gaa | tgt | gat | ctt | cca | gag | tgg | tgc | aat | ggt | act | tcc | cat | 405 |
| Glu | Val | Asn | Glu | Cys | Asp | Leu | Pro | Glu | Trp | Cys | Asn | Gly | Thr | Ser | His | |
| | | | | 85 | | | | | 90 | | | | | 95 | | |
| aag | tgc | cca | gat | gac | ttt | tat | gtg | gaa | gat | gga | att | ccc | tgt | aag | gag | 453 |
| Lys | Cys | Pro | Asp | Asp | Phe | Tyr | Val | Glu | Asp | Gly | Ile | Pro | Cys | Lys | Glu | |
| | | | 100 | | | | | 105 | | | | | 110 | | | |
| agg | ggc | tac | tgc | tat | gaa | aag | agc | tgt | cat | gac | cgc | aat | gaa | cag | tgt | 501 |
| Arg | Gly | Tyr | Cys | Tyr | Glu | Lys | Ser | Cys | His | Asp | Arg | Asn | Glu | Gln | Cys | |
| | | 115 | | | | | 120 | | | | | 125 | | | | |
| agg | agg | att | ttt | ggt | gca | ggc | gca | aat | act | gca | agt | gag | act | tgc | tac | 549 |
| Arg | Arg | Ile | Phe | Gly | Ala | Gly | Ala | Asn | Thr | Ala | Ser | Glu | Thr | Cys | Tyr | |
| | 130 | | | | | 135 | | | | | 140 | | | | | |
| aaa | gaa | ttg | aac | acc | tta | ggt | gac | cgt | gtt | ggt | cac | tgt | ggt | atc | aaa | 597 |
| Lys | Glu | Leu | Asn | Thr | Leu | Gly | Asp | Arg | Val | Gly | His | Cys | Gly | Ile | Lys | |
| 145 | | | | | 150 | | | | | 155 | | | | | 160 | |
| aat | gct | aca | tat | ata | aag | tgt | aat | atc | tca | gat | gtc | cag | tgt | gga | aga | 645 |
| Asn | Ala | Thr | Tyr | Ile | Lys | Cys | Asn | Ile | Ser | Asp | Val | Gln | Cys | Gly | Arg | |
| | | | | 165 | | | | | 170 | | | | | 175 | | |
| att | cag | tgt | gag | aat | gtg | aca | gaa | att | ccc | aat | atg | agt | gat | cat | act | 693 |
| Ile | Gln | Cys | Glu | Asn | Val | Thr | Glu | Ile | Pro | Asn | Met | Ser | Asp | His | Thr | |
| | | | 180 | | | | | 185 | | | | | 190 | | | |
| act | gtg | cat | tgg | gct | cgc | ttc | aat | gac | ata | atg | tgc | tgg | agt | act | gat | 741 |
| Thr | Val | His | Trp | Ala | Arg | Phe | Asn | Asp | Ile | Met | Cys | Trp | Ser | Thr | Asp | |
| | | 195 | | | | | 200 | | | | | 205 | | | | |
| tac | cat | ttg | ggg | atg | aag | gga | cct | gat | att | ggt | gaa | gtg | aaa | gat | gga | 789 |
| Tyr | His | Leu | Gly | Met | Lys | Gly | Pro | Asp | Ile | Gly | Glu | Val | Lys | Asp | Gly | |
| | 210 | | | | | 215 | | | | | 220 | | | | | |
| aca | gag | tgt | ggg | ata | gat | cat | ata | tgc | atc | cac | agg | cac | tgt | gtc | cat | 837 |
| Thr | Glu | Cys | Gly | Ile | Asp | His | Ile | Cys | Ile | His | Arg | His | Cys | Val | His | |
| 225 | | | | | 230 | | | | | 235 | | | | | 240 | |
| ata | acc | atc | ttg | aat | agt | aat | tgc | tca | cct | gca | ttt | tgt | aac | aag | agg | 885 |
| Ile | Thr | Ile | Leu | Asn | Ser | Asn | Cys | Ser | Pro | Ala | Phe | Cys | Asn | Lys | Arg | |
| | | | | 245 | | | | | 250 | | | | | 255 | | |
| ggc | atc | tgc | aac | aat | aaa | cat | cac | tgc | cat | tgc | aat | tat | ctg | tgg | gac | 933 |
| Gly | Ile | Cys | Asn | Asn | Lys | His | His | Cys | His | Cys | Asn | Tyr | Leu | Trp | Asp | |
| | | | 260 | | | | | 265 | | | | | 270 | | | |
| cct | ccc | aac | tgc | ctg | ata | aaa | ggc | tat | gga | ggt | agt | gtt | gac | agt | ggc | 981 |
| Pro | Pro | Asn | Cys | Leu | Ile | Lys | Gly | Tyr | Gly | Gly | Ser | Val | Asp | Ser | Gly | |
| | | 275 | | | | | 280 | | | | | 285 | | | | |

```
cca ccc cct aag aga aag aag aaa aag aag aga tct tgt gac aaa act      1029
Pro Pro Pro Lys Arg Lys Lys Lys Lys Lys Arg Ser Cys Asp Lys Thr
290                 295                 300 cac aca tgc cca ccg tgc cca gca cct gaa gcc gag ggc gcg ccg tca      1077
His Thr Cys Pro Pro Cys Pro Ala Pro Glu Ala Glu Gly Ala Pro Ser
305                 310                 315                 320 gtc ttc ctc ttc ccc cca aaa ccc aag gac acc ctc atg atc tcc cgg      1125
Val Phe Leu Phe Pro Pro Lys Pro Lys Asp Thr Leu Met Ile Ser Arg
            325                 330                 335 acc cct gag gtc aca tgc gtg gtg gtg gac gtg agc cac gaa gac cct      1173
Thr Pro Glu Val Thr Cys Val Val Val Asp Val Ser His Glu Asp Pro
        340                 345                 350 gag gtc aag ttc aac tgg tac gtg gac ggc gtg gag gtg cat aat gcc      1221
Glu Val Lys Phe Asn Trp Tyr Val Asp Gly Val Glu Val His Asn Ala
    355                 360                 365 aag aca aag ccg cgg gag gag cag tac aac agc acg tac cgg gtg gtc      1269
Lys Thr Lys Pro Arg Glu Glu Gln Tyr Asn Ser Thr Tyr Arg Val Val
370                 375                 380 agc gtc ctc acc gtc ctg cac cag gac tgg ctg aat ggc aag gag tac      1317
Ser Val Leu Thr Val Leu His Gln Asp Trp Leu Asn Gly Lys Glu Tyr
385                 390                 395                 400 aag tgc aag gtc tcc aac aaa gcc ctc cca gcc ccc atc gag aaa acc      1365
Lys Cys Lys Val Ser Asn Lys Ala Leu Pro Ala Pro Ile Glu Lys Thr
            405                 410                 415 atc tcc aaa gcc aaa ggg cag ccc cga gaa cca cag gtg tac acc ctg      1413
Ile Ser Lys Ala Lys Gly Gln Pro Arg Glu Pro Gln Val Tyr Thr Leu
        420                 425                 430 ccc cca tcc cgg gat gag ctg acc aag aac cag gtc agc ctg acc tgc      1461
Pro Pro Ser Arg Asp Glu Leu Thr Lys Asn Gln Val Ser Leu Thr Cys
    435                 440                 445 ctg gtc aaa ggc ttc tat ccc agc gac atc gcc gtg gag tgg gag agc      1509
Leu Val Lys Gly Phe Tyr Pro Ser Asp Ile Ala Val Glu Trp Glu Ser
450                 455                 460 aat ggg cag ccg gag aac aac tac aag acc acg cct ccc gtg ctg gac      1557
Asn Gly Gln Pro Glu Asn Asn Tyr Lys Thr Thr Pro Pro Val Leu Asp
465                 470                 475                 480 tcc gac ggc tcc ttc ttc ctc tac agc aag ctc acc gtg gac aag agc      1605
Ser Asp Gly Ser Phe Phe Leu Tyr Ser Lys Leu Thr Val Asp Lys Ser
            485                 490                 495 agg tgg cag cag ggg aac gtc ttc tca tgc tcc gtg atg cat gag gct      1653
Arg Trp Gln Gln Gly Asn Val Phe Ser Cys Ser Val Met His Glu Ala
        500                 505                 510 ctg cac aac cac tac acg cag aag agc ctc tcc ctg tct ccg ggt aaa      1701
Leu His Asn His Tyr Thr Gln Lys Ser Leu Ser Leu Ser Pro Gly Lys
    515                 520                 525 tga actagagcgg ccgctacaga t                                          1725

<210> SEQ ID NO 22
<211> LENGTH: 528
<212> TYPE: PRT
<213> ORGANISM: Artificial Sequence
<220> FEATURE:
<223> OTHER INFORMATION: Fusion Construct

<400> SEQUENCE: 22

Met Glu Thr Asp Thr Leu Leu Leu Trp Val Leu Leu Leu Trp Val Pro
1               5                   10                  15

Gly Ser Thr Gly Thr Ser Cys Gly Asn Gly Val Val Glu Glu Gly Glu
            20                  25                  30
```

```
Glu Cys Asp Cys Gly Pro Leu Lys His Cys Ala Lys Asp Pro Cys Cys
         35                  40                  45

Leu Ser Asn Cys Thr Leu Thr Asp Gly Ser Thr Cys Ala Phe Gly Leu
         50                  55                  60

Cys Cys Lys Asp Cys Lys Phe Leu Pro Ser Gly Lys Val Cys Arg Lys
 65              70                  75                      80

Glu Val Asn Glu Cys Asp Leu Pro Glu Trp Cys Asn Gly Thr Ser His
                 85                  90                  95

Lys Cys Pro Asp Asp Phe Tyr Val Glu Asp Gly Ile Pro Cys Lys Glu
            100                 105                 110

Arg Gly Tyr Cys Tyr Glu Lys Ser Cys His Asp Arg Asn Glu Gln Cys
            115                 120                 125

Arg Arg Ile Phe Gly Ala Gly Ala Asn Thr Ala Ser Glu Thr Cys Tyr
    130                 135                 140

Lys Glu Leu Asn Thr Leu Gly Asp Arg Val Gly His Cys Gly Ile Lys
145                 150                 155                 160

Asn Ala Thr Tyr Ile Lys Cys Asn Ile Ser Asp Val Gln Cys Gly Arg
                165                 170                 175

Ile Gln Cys Glu Asn Val Thr Glu Ile Pro Asn Met Ser Asp His Thr
            180                 185                 190

Thr Val His Trp Ala Arg Phe Asn Asp Ile Met Cys Trp Ser Thr Asp
        195                 200                 205

Tyr His Leu Gly Met Lys Gly Pro Asp Ile Gly Glu Val Lys Asp Gly
    210                 215                 220

Thr Glu Cys Gly Ile Asp His Ile Cys Ile His Arg His Cys Val His
225                 230                 235                 240

Ile Thr Ile Leu Asn Ser Asn Cys Ser Pro Ala Phe Cys Asn Lys Arg
                245                 250                 255

Gly Ile Cys Asn Asn Lys His His Cys His Cys Asn Tyr Leu Trp Asp
            260                 265                 270

Pro Pro Asn Cys Leu Ile Lys Gly Tyr Gly Gly Ser Val Asp Ser Gly
        275                 280                 285

Pro Pro Lys Arg Lys Lys Lys Lys Arg Ser Cys Asp Lys Thr
    290                 295                 300

His Thr Cys Pro Pro Cys Pro Ala Pro Glu Ala Glu Gly Ala Pro Ser
305                 310                 315                 320

Val Phe Leu Phe Pro Pro Lys Pro Lys Asp Thr Leu Met Ile Ser Arg
                325                 330                 335

Thr Pro Glu Val Thr Cys Val Val Val Asp Val Ser His Glu Asp Pro
            340                 345                 350

Glu Val Lys Phe Asn Trp Tyr Val Asp Gly Val Glu Val His Asn Ala
        355                 360                 365

Lys Thr Lys Pro Arg Glu Glu Gln Tyr Asn Ser Thr Tyr Arg Val Val
    370                 375                 380

Ser Val Leu Thr Val Leu His Gln Asp Trp Leu Asn Gly Lys Glu Tyr
385                 390                 395                 400

Lys Cys Lys Val Ser Asn Lys Ala Leu Pro Ala Pro Ile Glu Lys Thr
                405                 410                 415

Ile Ser Lys Ala Lys Gly Gln Pro Arg Glu Pro Gln Val Tyr Thr Leu
            420                 425                 430

Pro Pro Ser Arg Asp Glu Leu Thr Lys Asn Gln Val Ser Leu Thr Cys
        435                 440                 445

Leu Val Lys Gly Phe Tyr Pro Ser Asp Ile Ala Val Glu Trp Glu Ser
```

```
                    450             455             460
Asn Gly Gln Pro Glu Asn Asn Tyr Lys Thr Thr Pro Pro Val Leu Asp
465                 470             475                     480

Ser Asp Gly Ser Phe Phe Leu Tyr Ser Lys Leu Thr Val Asp Lys Ser
                485             490                 495

Arg Trp Gln Gln Gly Asn Val Phe Ser Cys Ser Val Met His Glu Ala
            500             505                 510

Leu His Asn His Tyr Thr Gln Lys Ser Leu Ser Leu Ser Pro Gly Lys
        515             520             525
```